United States Patent
Wang et al.

(10) Patent No.: US 7,828,732 B2
(45) Date of Patent: *Nov. 9, 2010

(54) BREAST CANCER SCREENING WITH ADJUNCTIVE ULTRASOUND MAMMOGRAPHY

(75) Inventors: Shih-Ping Wang, Los Altos, CA (US);
Donald Chin, Palo Alto, CA (US);
Fangyi Rao, San Jose, CA (US)

(73) Assignee: U-Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/479,468

(22) Filed: Jun. 5, 2009

(65) Prior Publication Data

US 2009/0240150 A1 Sep. 24, 2009

Related U.S. Application Data

(63) Continuation of application No. 10/160,836, filed on May 31, 2002, now Pat. No. 7,556,602, which is a continuation-in-part of application No. PCT/US01/43237, filed on Nov. 19, 2001.

(60) Provisional application No. 60/252,946, filed on Nov. 24, 2000, provisional application No. 60/326,715, filed on Oct. 3, 2001.

(51) Int. Cl.
*A61B 8/00* (2006.01)
(52) U.S. Cl. .................. 600/437; 600/443; 600/444; 600/461; 382/128
(58) Field of Classification Search ............ 382/128, 382/132, 284, 294; 600/337–461
See application file for complete search history.

(56) References Cited

U.S. PATENT DOCUMENTS 3,556,081 A 1/1971 Jones (Continued)

FOREIGN PATENT DOCUMENTS

DE 19753571 A1 6/1999

(Continued)

OTHER PUBLICATIONS

Bassett, L., "Automated and Hand-Held Breast US: Effect on Patient Management", Radiology 165, pp. 103-108 (1987).

(Continued)

*Primary Examiner*—Long V Le
*Assistant Examiner*—Sanjay Cattungal
(74) *Attorney, Agent, or Firm*—Cooper and Dunham, LLP

(57) ABSTRACT

An adjunctive ultrasound mammography system and associated methods are described, comprising a scanning apparatus for facilitating standardized, repeatable breast ultrasound scans, and further comprising an adjunctive ultrasound display apparatus configured for fast, intuitive viewing of adjunctive ultrasound data concurrently with x-ray mammogram information. In one preferred embodiment, thick-slice ultrasound images are displayed near an x-ray mammogram such that a screening radiologist can quickly view the thick-slice images for assistance in interpreting the x-ray mammogram. Methods for concurrently acquiring and displaying vibrational resonance image (VDI) data are described. Computer-aided diagnosis (CAD) algorithms that incorporate acoustically-based feature vectors are described, the feature vectors including lateral shadow metrics, vertical shadow metrics, posterior enhancement metrics, and VDI-based metrics. Algorithms are also described that combine x-ray mammogram CAD results with adjunctive ultrasound CAD results without requiring complex image registrations therebetween. Many of the practical, economic, and political barriers to acceptance and integration of ultrasound mammography into existing mass breast cancer screening environments are mitigated.

37 Claims, 41 Drawing Sheets

U.S. PATENT DOCUMENTS

| | | | |
|---|---|---|---|
| 3,765,403 A | 10/1973 | Brenden | |
| 4,167,180 A | 9/1979 | Kossoff | |
| 4,282,880 A | 8/1981 | Gardineer et al. | |
| 4,298,009 A | 11/1981 | Mezrich et al. | |
| 4,478,084 A | 10/1984 | Hassler et al. | |
| 4,485,819 A | 12/1984 | Igl | |
| 4,722,345 A | 2/1988 | Ueno et al. | |
| 4,729,019 A | 3/1988 | Rouvrais | |
| 4,796,632 A | 1/1989 | Boyd et al. | |
| 4,930,143 A | 5/1990 | Lundgren et al. | |
| 5,078,142 A | 1/1992 | Siczek et al. | |
| 5,079,698 A | 1/1992 | Grenier et al. | |
| 5,099,848 A | 3/1992 | Parker et al. | |
| 5,133,020 A | 7/1992 | Giger et al. | |
| 5,346,057 A | 9/1994 | Fisher et al. | |
| 5,379,769 A | 1/1995 | Ito et al. | |
| 5,396,890 A | 3/1995 | Weng | |
| 5,413,211 A | 5/1995 | Faulkner | |
| 5,433,202 A | 7/1995 | Mitchell et al. | |
| 5,479,927 A | 1/1996 | Shmulewitz | |
| 5,488,952 A | 2/1996 | Schoolman | |
| 5,491,627 A | 2/1996 | Zhang et al. | |
| 5,503,152 A | 4/1996 | Oakley et al. | |
| 5,511,026 A | 4/1996 | Cleveland et al. | |
| 5,603,326 A | 2/1997 | Richter | |
| 5,640,956 A | 6/1997 | Getzinger et al. | |
| 5,660,185 A | 8/1997 | Shmulewitz et al. | |
| 5,662,109 A | 9/1997 | Hutson | |
| 5,664,573 A | 9/1997 | Shmulewitz | |
| 5,671,294 A | 9/1997 | Rogers et al. | |
| 5,673,332 A | 9/1997 | Nishikawa et al. | |
| 5,709,206 A | 1/1998 | Teboul | |
| 5,729,620 A | 3/1998 | Wang | |
| 5,734,384 A | 3/1998 | Yanof et al. | |
| 5,776,062 A | 7/1998 | Nields | |
| 5,779,641 A | 7/1998 | Hatfield et al. | |
| 5,790,690 A | 8/1998 | Doi et al. | |
| 5,803,082 A | 9/1998 | Stapleton et al. | |
| 5,815,591 A | 9/1998 | Roehrig et al. | |
| 5,820,552 A | 10/1998 | Crosby et al. | |
| 5,828,774 A | 10/1998 | Wang | |
| 5,833,627 A | 11/1998 | Shmulewitz et al. | |
| 5,840,032 A | 11/1998 | Hatfield et al. | |
| 5,851,180 A | 12/1998 | Crosby et al. | |
| 5,865,750 A | 2/1999 | Hatfield et al. | |
| 5,899,863 A | 5/1999 | Hatfield et al. | |
| 5,904,653 A | 5/1999 | Hatfield et al. | |
| 5,917,929 A | 6/1999 | Marshall et al. | |
| 5,919,139 A | 7/1999 | Lin | |
| 5,934,288 A | 8/1999 | Avila et al. | |
| 5,935,071 A | 8/1999 | Schneider et al. | |
| 5,938,613 A | 8/1999 | Shmulewitz et al. | |
| 5,954,650 A | 9/1999 | Saito et al. | |
| 5,964,707 A | 10/1999 | Fenster et al. | |
| 5,983,123 A | 11/1999 | Shmulewitz | |
| 5,984,870 A | 11/1999 | Giger et al. | |
| 5,997,477 A | 12/1999 | Sehgal | |
| 6,027,457 A | 2/2000 | Shmulewitz et al. | |
| 6,029,797 A | 2/2000 | Olsson | |
| 6,035,056 A | 3/2000 | Karssemeijer | |
| 6,059,727 A | 5/2000 | Fowlkes et al. | |
| 6,068,597 A | 5/2000 | Lin | |
| 6,075,879 A | 6/2000 | Roehrig et al. | |
| 6,091,841 A | 7/2000 | Rogers et al. | |
| 6,102,861 A | 8/2000 | Avila et al. | |
| 6,102,866 A | 8/2000 | Nields et al. | |
| 6,117,080 A | 9/2000 | Schwartz | |
| 6,123,733 A | 9/2000 | Dalton | |
| 6,155,978 A | 12/2000 | Cline et al. | |
| 6,157,697 A | 12/2000 | Mertelmeier et al. | |
| 6,178,224 B1 | 1/2001 | Policher et al. | |
| 6,181,769 B1 | 1/2001 | Hoheisel et al. | |
| 6,190,334 B1 | 2/2001 | Lasky et al. | |
| 6,198,838 B1 | 3/2001 | Roehrig et al. | |
| 6,237,750 B1 | 5/2001 | Damkjaer et al. | |
| 6,246,782 B1 | 6/2001 | Shapiro et al. | |
| 6,254,538 B1 | 7/2001 | Downey et al. | |
| 6,263,092 B1 | 7/2001 | Roehrig et al. | |
| 6,266,435 B1 | 7/2001 | Wang | |
| 6,269,565 B1 | 8/2001 | Inbar et al. | |
| 6,277,074 B1 | 8/2001 | Chaturvedi et al. | |
| 6,278,793 B1 | 8/2001 | Gur et al. | |
| 6,282,305 B1 | 8/2001 | Huo et al. | |
| 6,301,378 B1 | 10/2001 | Karssemeijer et al. | |
| 6,311,419 B1 | 11/2001 | Inbar | |
| 6,317,617 B1 | 11/2001 | Gilhuijs et al. | |
| 6,334,847 B1 | 1/2002 | Fenster et al. | |
| 6,377,838 B1 | 4/2002 | Iwanczyk et al. | |
| 6,385,474 B1 | 5/2002 | Rather et al. | |
| 6,396,940 B1 | 5/2002 | Carrott et al. | |
| 6,413,219 B1 | 7/2002 | Avila et al. | |
| 6,450,962 B1 | 9/2002 | Brandl et al. | |
| 6,459,925 B1 | 10/2002 | Nields et al. | |
| 6,461,298 B1 | 10/2002 | Fenster et al. | |
| 6,524,246 B1 | 2/2003 | Kelly et al. | |
| 6,530,885 B1 | 3/2003 | Entrekin et al. | |
| 6,574,499 B1 | 6/2003 | Dines et al. | |
| 6,628,815 B2 | 9/2003 | Wang | |
| 6,630,937 B2 | 10/2003 | Kallergi et al. | |
| 6,636,584 B2 | 10/2003 | Johnson et al. | |
| 6,682,484 B1 | 1/2004 | Entrekin et al. | |
| 6,876,879 B2 | 4/2005 | Dines et al. | |
| 6,909,792 B1 | 6/2005 | Carrott et al. | |
| 7,103,205 B2 | 9/2006 | Wang et al. | |
| 7,313,260 B2 | 12/2007 | Wang et al. | |
| 2002/0173722 A1 | 11/2002 | Hoctor et al. | |
| 2003/0000810 A1 | 1/2003 | Hansen et al. | |
| 2003/0007598 A1 | 1/2003 | Wang et al. | |
| 2003/0015406 A1 | 1/2003 | Guldenfels et al. | |
| 2003/0181801 A1 | 9/2003 | Lasser et al. | |
| 2003/0194121 A1 | 10/2003 | Eberhard et al. | |
| 2003/0212327 A1 | 11/2003 | Wang et al. | |
| 2004/0015080 A1 | 1/2004 | Kelly et al. | |
| 2004/0181152 A1 | 9/2004 | Zhang | |
| 2004/0254464 A1 | 12/2004 | Stribling | |
| 2005/0113683 A1 | 5/2005 | Lokhandwalla et al. | |
| 2005/0171430 A1 | 8/2005 | Zhang et al. | |

FOREIGN PATENT DOCUMENTS

| | | |
|---|---|---|
| DE | 19902521 A1 | 7/2000 |
| EP | 0882426 | 12/1998 |
| EP | 0730431 | 3/2000 |
| JP | 2003-310614 | 11/2003 |
| WO | WO83/02053 A1 | 6/1983 |
| WO | WO94/21189 | 9/1994 |
| WO | WO02/17792 | 3/2002 |
| WO | WO03/103500 A1 | 12/2003 |
| WO | WO2004/064644 A1 | 8/2004 |

OTHER PUBLICATIONS

Buchberger, W., et al., "Incidental Findings on Sonography of the Breast: Clinical Significance and Diagnostic Workup", American Journal of Radiology (AJR) 173, pp. 921-927 Oct. 1999.

Carson, P. et al., "Lesion Detectability in Ultrasonic Computed Tomography of Symptomatic Breast Patients", Investigative Radiology, vol. 23, No. 6, pp. 421-427, Jun. 1998.

Chen et al., "Computer-aided Diagnosis Applied to US of Solid Breast Nodules by Using Neural Networks", Radiology, pp. 407-412, Nov. 1999.

Cheng et al., "Automated Detection of Breast Tumors in Ultrasonic Images Using Fuzzy Reasoning", Proceedings of the IEEE Computer Society International Conference on Image Processing vol. III, pp. 420-423, Oct. 26-29, 1997.

Dawant, Benoit M. et al., "Image Segmentation", Handbook of Medical Imaging, vol. 2; Medical Image Processing and Analysis, Sonka and Fitzpatrick, eds., Chapter 2, pp. 98-101, SPIE Press, 2000.

Giger et al., "Computer-Aided Diagnosis in Mammography", Handbook of Medical Imaging, vol. 2: Medical Image Processing and Analysis, Sonka and Fitzpatrick, Chapter 15, pp. 915-1004, SPIE Press 2000.

Heywang-Kobrunner, Dershaw and Schreer, Diagnostic Breast Imaging, pp. 87-102, Thieme Publishers 2001.

Jackson, Valerie P., "Controversies in Ultrasound Screening", Society of Breast Imaging 5th Postgraduate Course, May 16-19, 2001, Sheraton Harbor Island, San Diego, CA, pp. 93-95, May 16, 2001.

Jalali, "Sound Combination: Ultrasound Paired With Mammography Can Improve Cancer Detection for Dense-Breasted Women", Advance for Administrators In Radiology and Radiation Oncology, pp. 68-70, Mar. 1999.

Kopans, D. et al., "Whole-Breast US Imaging: Four Year Follow-Up", Radiology 157: 505-507, 1985.

Kopans, "Breast Cancer Screening With Ultrasonography", Lancet, vol. 354, pp. 2096-2097, Dec. 18/25, 1999.

LABSONICS, Inc., "LABSONICS Ultrasound Breast Scanner: Accurate, High-Performance Investigation of the Breast for Confident Diagnosis", 8-page product brochure from LABSONICS, Inc., Mooresville, Indiana, 1983.

Lehman et al., "Effect of Age and Breast Density on Screening Mammograms with False-Positive Findings", American Journal of Radiology (AJR) 173: 1651-1655, Dec. 1999.

LORAD, a Hologic Company, "Fully Automatic Self-Adjusting Tilt Compression Plate", 3-page product description downloaded and printed on May 22, 2002 from www.loradmedical.com/p225.html.

Lowers, J., "Experimental Modes Abound for Detecting Breast Cancer: Vibrational Resonance Technique Among the Contenders", Women's Health Supplement to Diagnostic Imaging, pp. 15-17, Apr. 2001.

McKnoulty, L., "Ultrasound has Unique Strengths In Breast Imaging", 3-page printout from www.auntminnie.com one Mar. 1, 2002, Jan. 2002.

McSweeney, M. et al., "Whole Breast Snongraphy," Radiologic Clinics of North America, vol. 23, No. 1, pp. 157-167, Mar. 1985.

Mendelson, Ellen B., "Current Status of Breast US", RSNA Cat-egorical Course In Breast Imaging, pp. 295-309, 1999.

Qayyum, A. et al., "MR Imaging Features of Infiltrating Lobular Carcinoma of the Breast: Histopathologic Correlation", American Journal of Radiology (AJR) 178: 1227-1232, May 2002.

Rahbar, G. et al., "Benign Versus Malignant Solid Breast Masses: US Differentiation", Radiology 213:889-894, 1999.

Rapp, Cynthia L., "Breast Ultrasound", Lecture Notes for EDA AHP 230-0406, Health & Sciences Television Network, Primedia Healthcare, Carrolton TX, Mar. 2000.

Richter, K. et al., "Quantitative Parameters Measured by a New Sonographic Method for Differentiation of Benign and Malignant Breast Disease", Investigative Radiology, vol. 30, No. 7, pp. 401-411, Jul. 1995.

Richter, K. et al., "Detection of Diffuse Breast Cancers with a New Sonographic Method", J. Clinical Ultrasound 24: pp. 157-168, May 1996.

Richter, K. et al., "Differentiation of Breast Lesions by Measurements Under Craniocaudal and Lateromedial Compression Using a New Sonographic Method", Investigative Radiology, vol. 31, No. 7, pp. 401-414, Jul. 1996.

Richter, K. et al., "Description and First Clinical Use of a New System for Combined Mammography and Automated Clinical Amplitude/Velocity Reconstructive Imaging Breast Sonography", Investigative Radiology, vol. 32, No. 1, pp. 19-28, Jan. 1997.

Richter, K. et al., "Detection of Malignant and Benign Breast Lesions with an Automated US System: Results in 120 Cases", Radiology 205: pp. 823-830, Dec. 1997.

Russ, "The Image Processing Handbook, 3rd Edition", CRC Press/IEEE Press, p. 264, 1998.

Schreiman, J. et al., "Ultrasound Transmission Computed Tomography of the Breast", Radiology 150; pp. 523-530, 1984.

Singh, S. and Al-Mansoori, R., "Identification of Regions of Interest in Digital Mammograms", J. Intelligent Systems10:2, 2000.

Smith, D., "Breast Ultrasound", Radiologic Clinics of North America, vol. 39, No. 3, pp. 485-497, May 2001.

"Ultrasound RSNA Preview: Productivity and Ease of Use Dominate New Ultrasound Productss", Medical Imaging, pp. 55-56, Nov. 1999.

Zonderland, H. et al., "Diagnosis of Breast Cancer: Contribution of US as an Adjunct of Mammography", Radiology 213: 413-422, 1999.

Medison Image Gallery, five (5) selected pages from www.medison.com, printed Oct. 10, 2001.

Foster, F.S. et al., "The Ultrasound Macroscope: Initial Studies of Breast Tissue", Ultrasonic Imaging USA, vol. 6, No. 3, Jul. 1984, pp. 243-261.

European Search Report dated Jan. 29, 2007 in connection with counterpart European patent application No. 03 73 4336.

Dec. 28, 2005 International Search Report and Written Opinion in connection with International Application No. PCT/US05/19604.

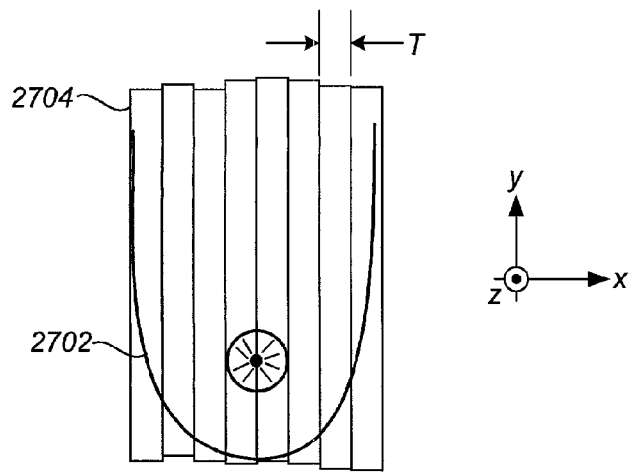
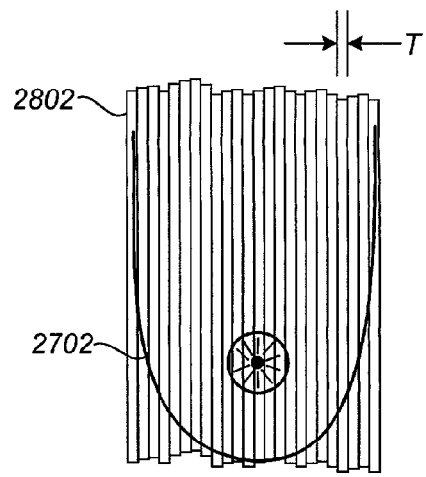
FIG. 27
FIG. 28
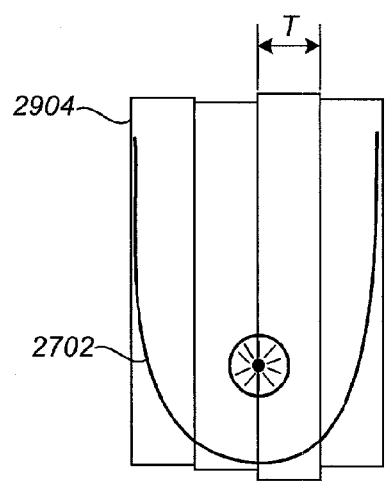
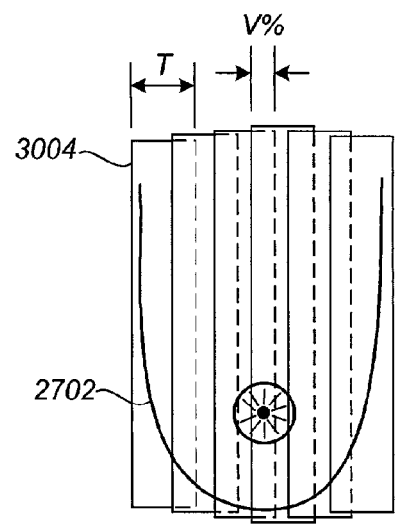
FIG. 29
FIG. 30

BREAST CANCER SCREENING WITH ADJUNCTIVE ULTRASOUND MAMMOGRAPHY

CROSS-REFERENCE TO RELATED APPLICATIONS

This application is a Rule 1.53(b) continuation of Ser. No. 10/160,836, filed May 31, 2002 now U.S. Pat. No. 7,556,602, which is a continuation-in-part of International Application No. PCT/US01/43237, filed Nov. 19, 2001, which claims the benefit of U.S. Provisional No. 60/252,946, filed Nov. 24, 2000. U.S. application Ser. No. 10/160,836 also claims the benefit of U.S. Provisional No. 60/326,715, filed Oct. 3, 2001. The present application is also related to U.S. application Ser. No. 10/305,936 filed Nov. 27, 2002 (which is a continuation-in-part of Ser. No. 10/160,836), U.S. application Ser. No. 10/997,293 filed Nov. 23, 2004 (which is a continuation-in-part of Ser. No. 10/305,936), U.S. application Ser. No. 10/305,661, filed Nov. 27, 2002, now U.S. Pat. No. 7,103,205 (which is a continuation-in-part of Ser. No. 10/160,836 filed May 31, 2002), and U.S. application Ser. No. 11/489,371 filed Jul. 28, 2006, now U.S. Pat. No. 7,313,260 (which is a continuation of Ser. No. 10/305,661).

FIELD

This patent specification relates to medical imaging systems and processes. In particular, it relates to the acquisition and display of breast ultrasound information in a manner that complements traditional x-ray mammogram-based breast cancer screening methods.

BACKGROUND

Breast cancer is the most common cancer among women other than skin cancer, and is the second leading cause of cancer death in women after lung cancer. The American Cancer Society currently estimates that there are about 203,500 new invasive cases of breast cancer per year among women in the United States and 39,600 deaths per year from the disease. Prevention and early diagnosis of breast cancer are of foremost importance. Because early breast cancer does not produce symptoms, the American Cancer Society recommends a screening mammogram and a clinical breast examination every year for women over the age of 40. See articles A-I cited at the end of the disclosure, and material cited in the body of the disclosure herein.

X-ray mammography is currently the imaging method for mass screening of breast cancer. In health maintenance organizations (HMO's) and other medical organizations, specialized x-ray mammography clinics designed for high patient throughput are being increasingly used to screen as many women as possible in a time and cost efficient manner. Numerous studies have shown that early detection saves lives and increases treatment options. Recent declines in breast cancer mortality rates (e.g., 39,600 deaths in 2002 versus 41,200 in 2000) have been attributed, in large part, to the regular use of screening x-ray mammography.

Screening x-ray mammography practice in the United States has become largely standardized. For each x-ray mammogram screening of a patient, two standard x-ray mammogram views of each breast are commonly taken: a top (head-to-toe) view ordinarily called the craniocaudal view ("CC"), and a lateral view ordinarily called the mediolateral oblique view ("MLO"). Several efficiencies arise by virtue of this standardization. Importantly, the examinations can be conducted by an x-ray technician instead of a radiologist, with the radiologist later analyzing x-ray mammograms en masse for a large number of patients. An experienced radiologist can achieve a high throughput, e.g., on the order of 2 minutes per patient. This is a key advantage in today's cost-conscious health care environments, because additional radiologist time per patient means additional cost per patient. The efficacy of radiological procedures is today measured by the cost in dollars per quality adjusted life year (QALY), with procedures costing more than $100,000 per QALY being neither encouraged nor prescribed.

Other advantages of x-ray mammogram standardization include: the ability to compare and statistically track large numbers of x-ray mammograms taken from different facilities; the ability to track changes in a single patient over time even if the x-ray mammograms are taken at different facilities; the ability of radiologists to gain recursive expertise in analyzing the standard x-ray mammogram views; and the repeatability of results. The standardization of x-ray mammograms also yields benefits in the public health care area, including the ability for the U.S. government to provide a fixed and predictable per-mammogram reimbursement for Medicare patients. Additionally, health maintenance organizations (HMOs) and other medical insurers are provided with predictable outlays for breast cancer screening of their member patients using x-ray mammography.

A well-known shortcoming of x-ray mammography practice, however, is found in the case of dense-breasted women including patients with high content of fibroglandular tissues in their breasts. Because fibroglandular tissues have higher x-ray absorption than the surrounding fatty tissues, portions of breasts with high fibroglandular tissue content are not well penetrated by x-rays and thus the resulting mammograms would contain little or no information in areas where fibroglandular tissues reside. A study by Lehman et. al., entitled "Effect of Age and Breast Density on Screening Mammograms with False-Positive Findings," on 46,340 patients, published in the December 1999 issue of the American Journal of Reoentgenology (AJR), reports that the proportion of dense breasts (summing those with "heterogeneously dense" and "extremely dense" breasts) account for about 52% of women with age range of 35-39, 47% of age range 40-49, 32% of age range 50-59, 24% of age range 60-69, 23% of age range 70 or older, and 36% for all ages. For the estimated 36% of the female population who have dense breasts, this means that at least a portion of the breast area on the x-ray mammogram cannot be scrutinized well for lesions by x-ray mammography alone. As a result, lesions camouflaged by dense breast tissue may go undetected.

Indeed, a study by Kolb et. al. on 18,005 consecutive patients, as reported by Jalali, entitled "Sound Combination: Ultrasound Paired With a Mammography Can Improve Cancer Detection for Dense-Breasted Women," published in the March 1999 issue of ADVANCE for Administrators In Radiology and Radiation Oncology, pages 68-70, states that x-ray mammography alone was able to detect only 70 percent of the cancers (56 of the 80 cancers) in 7,202 patients with dense breasts. Kopans, in a paper entitled "Breast cancer screening with ultrasonography," published in Lancet, Volume 357 (1999), pages 2096-2097, estimates that only 68% of the breast cancers of the screening population would be detected by x-ray mammography alone.

The study by Kolb, supra, revealed that by performing ultrasound examination, in the hand-held fashion by a physician and in real-time at a rate of 4 to 20 minutes per patient, on the 7,202 women with dense breasts, an additional 24 percent (19 of the 80 cancers) were detected. X-ray mammography alone detected 70 percent (56 of the 80 cancers), while combining x-ray mammography with ultrasound examination 94 percent of the cancers (75 of the 80 cancers) in dense breasts were detected.

Several other studies showing improved early breast cancer detection using independent ultrasound examination are reported in Jackson, "Controversies in Ultrasound Screening," Society of Breast Imaging 5$^{th}$ Postgraduate Course, San Diego, Calif., pp. 93-95 (May 2001).

A study by Richter et. al. evaluated an "automated ultrasound system" that generated two automatically reconstructed survey images of the breast based on an acquired set of three-dimensional B-mode scans, and was reported in Richter, K. et. al., "Detection of Malignant and Benign Breast Lesions with an Automated US System: Results in 120 Cases," Radiology 205:823-830 (December 1997). An experimental compression system compressed the breast as in mammography while a motor-driven transducer scanned the breast through an upper compression plate. The two survey images that were constructed from these three-dimensional B-mode scans were (i) a maximum intensity projection (MIP) image mapped from the three-dimensional B-mode scans onto a two-dimensional plane parallel to a lower compression plate, and (ii) a velocity map representing an average acoustic velocity in a direction perpendicular to the lower compression plate. For each patient among a set of patients having known malignant lesions, known benign lesions, or neither, four "blinded" radiologists not involved in the examination of the patients separately examined (i) the two survey images derived from the B-mode scans, with optional access to any of the original B-mode images, and (ii) a corresponding set of conventional x-ray mammograms. It was found that the rate of detection for malignant lesions was 100% (39 of 39 lesions) for combined mammography and ultrasound for all of the radiologists, with the condition that each lesion was identified on at least one of the medical images. The authors stated, "For both benign and malignant lesions, our results show that mammography and ultrasound are complementary modalities; as expected, this does not hold for those lesions that were objectively depicted by means of only one of the two modalities." Richter, supra at 830.

Despite strong evidence that use of independent ultrasound examination would improve early breast cancer detection and therefore save lives, substantial resistance against such use currently exists in the medical industry and among policymakers. Jackson, for example, in a paper entitled "The current role of ultrasonography in breast imaging," published in Radiologic Clinics of North America, Volume 33 (1995), pages 1161-1170, states, "The use of ultrasound for breast screening may, however, be harmful to patients." A standard textbook for breast imaging by Heywang-Kobrunner, Dershaw and Schreer, entitled: "Diagnostic Breast Imaging", published in 2001 by Thieme, states on page 88:

"Only anecdotal evidence suggests that sonographic screening added to mammography may allow detection of additional carcinomas. However, the existing results suggest that the false positive rate (recommendation for biopsy for lesions that are benign) may be unacceptably high with sonography. The examination is also very operator dependent and time consuming. Feasibility of a quality assurance (technique and reporting), which, however, would be indispensable for any type of ultrasound screening, is not established."

Moreover, the Standards of the American College of Radiology specifically recommend against sonography for breast cancer screening. Heywang-Kobrunner et. al., supra at p. 88. The following interrelated factors are often cited against widespread use of ultrasound in breast cancer screening: (i) the false negative (missing) rate of independent ultrasound examination is unknown, (ii) the false positive rate of independent ultrasound examination is known to be very high, leading to an increase in unneeded patient callbacks and biopsies, (iii) lack of image acquisition standardization, leading to variability among different operators and radiologists, (iv) the additional time and equipment required to conduct the ultrasound examination, leading to an increase in cost, and (v) most if not all the breast physicians and radiologists are not trained to read screening ultrasound images, which contain features not found in current breast imaging textbooks or taught in current medical school courses, leading to a potential increase in false negative (missing) rate and in the additional radiologist time required to analyze the ultrasound images, and additional training and clinical experience required for the radiologist to properly analyze the ultrasound images.

Current ad hoc techniques for screening ultrasound examination, as reported by Kolb and others, indeed may not be amenable to large-scale integration into the current breast cancer screening environment. For example, in the studies cited supra in support of breast screening ultrasound, many of the doctors simply performed the entire screening process themselves, scanning the breast with a hand-held ultrasound probe and viewing the ultrasound display monitor in real-time. Because this usually takes 4 to 20 minutes, such real-time analysis would be cost-prohibitive in today's mass screening environment. The ultrasound viewings are conducted independently on the monitor of the ultrasound machine in real-time without referring to any x-ray mammogram information that may exist for the patient. More importantly, if one pictures the breast as a book, the x-ray mammogram is a picture of the whole book with all the pages of the book superimposed on each another, while the ultrasound images each page independently. The ultrasound image contains many detailed features not observable in an x-ray mammogram, and is very different from a x-ray mammogram in appearance. In addition, the x-ray mammogram is fixed in orientation, either in CC or in MLO views, whereas, as reported by Kolb and others, for example when each breast is scanned in the radial and/or anti-radial fashion around the nipple, each ultrasound image has a different orientation and plane. Thus, even if one wants to view the ultrasound image with an x-ray mammogram, very little can be gained from such practice.

The problem of radiologist skill and training is a particularly important problem to overcome for any breast screening ultrasound scheme to gain acceptance. It has been estimated that only a small portion of today's radiologists would have the ability to effectively use today's ad hoc ultrasound techniques in a mass-screening environment without unacceptable increases in false positives or false negatives.

Vibrational Doppler imaging (VDI) and vibrational resonance techniques, such as those discussed in U.S. Pat. Nos. 5,919,139 and 6,068,597 have been proposed for analyzing suspect tumors. As discussed in Lowers, J., "Experimental Modes Abound For Detecting Breast Cancer: Vibrational Resonance Technique Among the Contenders," Women's Health Supplement to Diagnostic Imaging (April 2001) at pp. 15-17, an audio speaker is attached to the ultrasound probe to introduce audio-range vibrational tones (e.g., 69-247 Hz) into the patient during the acquisition of power Doppler ultrasound frames. Different tissue types often vibrate by different amounts responsive to the acoustic signals, and the different vibrations result in different power Doppler readings. Generally speaking, many types of suspect lesions tend to vibrate less than the surrounding breast tissue. It has been found that the absence of vibrations as compared to surrounding tissue can help to clearly differentiate suspect lesions, even those that appear isoechoic (i.e., less noticeable) with surrounding tissue on B-scan ultrasound frames. In some clinical practice, the patient is asked to produce her own acoustic vibration by humming at audio frequencies. This practice is called "fremitus." Unless otherwise specified herein, VDI refers generally to color or power Doppler images derived from a breast as it is vibrated at one or more audio frequencies, while vibrational resonance refers to VDI data taken at one or more particular sets of audio frequencies.

In view of the above discussions, it would be desirable to provide an adjunctive ultrasound mammography system that integrates ultrasound mammography into current breast cancer screening methodologies.

It would be further desirable to provide an adjunctive ultrasound mammography system in which the benefits of the many years of professional expertise developed in relation to current x-ray mammography, either the analog or the digital, methods are maintained.

It would be further desirable to provide an adjunctive ultrasound mammography system that takes little or no special familiarization or training from the radiologist in order to effectively view ultrasound information in combination with the x-ray mammogram information.

It would be further desirable to provide an adjunctive ultrasound mammography system in which technicians or assistants may perform the ultrasound scans for later en masse analysis by a physician, the physician's presence not being required during the scanning procedure.

It would be even further desirable to provide an adjunctive ultrasound mammography system in which per-patient image analysis time is not substantially increased as compared to x-ray mammogram analysis alone, or which may even reduce per-patient image analysis time.

It would be still further desirable to provide an adjunctive ultrasound mammography image acquisition system that assures standardization of techniques and minimizes operator variability.

It would be even further desirable to provide an adjunctive ultrasound mammography system that is easy to use, comfortable to the patient, and provides standardized and repeatable ultrasonic scans.

It would be still further desirable to provide an adjunctive ultrasound mammography system that is amenable to two and three dimensional computer-assisted diagnosis (CAD) techniques and to provide several such CAD techniques.

It would be still further desirable to provide an adjunctive ultrasound mammography system that is amenable to combined CAD analysis of ultrasound information with x-ray mammogram information for an enhanced CAD system and to provide several such CAD techniques.

It would be even further desirable to provide an adjunctive ultrasound mammography system for which, upon acquisition of the system, any increase in breast cancer screening costs is offset by savings brought about by an increased early breast cancer detection rate, whereby cost per patient QALY is ultimately reduced.

SUMMARY

An adjunctive ultrasound mammography system and associated methods are provided, comprising a scanning apparatus for facilitating standardized, repeatable breast ultrasound scans, and further comprising an adjunctive ultrasound display apparatus configured for fast, intuitive viewing of ultrasound information concurrently with x-ray mammogram information. Many of the practical barriers to widespread integration of ultrasound mammography into existing mass breast cancer screening environments are mitigated. Additionally, many of the medical community acceptance barriers, economic barriers, and other political barriers to widespread integration of ultrasound mammography into existing mass breast cancer screening environments are mitigated.

The scanning apparatus of the preferred adjunctive ultrasound mammography system is configured to yield ultrasound slices from successive planes in a breast volume substantially parallel to a plane of a predetermined x-ray mammogram view of the breast. The scanning apparatus supports and maintains the breast during the ultrasound scan in a manner that promotes volumetric thoroughness of the scan, with the resulting ultrasound slices extending substantially all the way to the chest wall. The scanning apparatus is capable of partially flattening the breast according to a desired x-ray mammogram view plane while also maintaining patient comfort. Efficient patient throughput is facilitated, while at the same time the risk of inter-patient contamination and fomite propagation is minimized.

In one preferred embodiment, the scanning apparatus comprises a reservoir containing an acoustically conductive fluid for immersion of the breast therein, the scanning apparatus further comprising an ultrasound probe immersed within or positioned under the reservoir such that gap-free acoustic communication with the breast is established. A mechanical translation mechanism moves the ultrasound probe across the breast as ultrasound scans are taken, yielding a set of raw ultrasound slices. Preferably, the scanning apparatus further comprises two compression plates positioned on opposite sides of the breast, the compression plates being oriented parallel to a standard x-ray mammogram view plane such that information obtained from the raw ultrasound slices corresponds more closely to a standard x-ray mammogram view.

Preferably, the compression plates of the scanning apparatus are coupled to audio frequency transducers for accommodating a vibrational Doppler imaging (VDI) modality. As the ultrasound probe is moved across the breast, successive B-mode ultrasound slices are acquired at spatial intervals corresponding to a desired resolution, the audio frequency transducers being silent during these B-mode scans. However, at regular spatial intervals, acquisition of B-mode slices is temporarily suspended, the audio frequency transducers are activated, and VDI imaging information is obtained.

According to another preferred embodiment, the scanning apparatus comprises first and second compressive members that sandwich the breast along a plane that is near a standard x-ray mammogram view plane. The first compressive member is movable with respect to the second compressive member to allow entry of the breast therebetween, and preferably comprises a conformable sheet of acoustically transparent material in a taut state. An inner surface of the first compressive member compresses the breast while an outer surface accommodates an ultrasound probe that scans the compressed breast. Preferably, the first compressive member forms a first shallow angle with respect to the standard x-ray mammogram view plane such that interrogating ultrasonic waves from the ultrasound probe can penetrate through to the chest wall. This enhances image quality near the chest wall while still providing an overall mammogram-like view of the breast. Preferably, a nipple support element is provided on the second compressive member that urges the nipple into acoustic communication with the first compressive member. This enhances ultrasonic imaging of the breast nipple, which is a meaningful reference point in comparing the ultrasound mammography results to the x-ray mammography results. The second compressive member may comprise a substantially rigid surface and/or may comprise an air bag, a fluid bag, or a preformed sponge-like material designed to promote patient comfort while also providing a sufficient degree of breast compression.

According to a preferred embodiment, the adjunctive ultrasound display apparatus provides an array of thick-slice thumbnail images, each thick-slice thumbnail image comprising information integrated from a plurality of adjacent ultrasound slices and representing a thick-slice or slab-like portion of the breast volume substantially parallel to the standard x-ray mammogram view. The adjunctive ultrasound display apparatus comprises one or more adjunct display monitors positioned near a conventional x-ray mammogram display such that a screening radiologist can quickly turn their attention to the thick-slice thumbnail images to clarify questionable portions of the x-ray mammogram. In one preferred embodiment, each thick-slice thumbnail image is positioned not more than twenty inches from its corresponding x-ray mammogram view. Whereas the x-ray mammogram only shows the overall sum of breast tissue densities, the ultrasound thick-slice thumbnail images permit a quick view of individual thick-slice portions of the breast tissue. This allows the radiologist, for example, to quickly investigate whether a suspicious-looking mass in the x-ray mammogram is truly a tumor or is simply a coincidental confluence of patterns from different breast planes.

According to a preferred embodiment, an intuitive, interactive user interface is provided that allows the radiologist to easily manipulate and examine the adjunctive ultrasound data in a manner that facilitates rapid screening. In one preferred embodiment, upon selection of a given thick-slice thumbnail image, a corresponding thick-slice image is expanded to a full-scale representation on the display that is comparable in size to the x-ray mammogram being viewed. In another preferred embodiment, the radiologist may examine each individual ultrasound slice used to form the thick-slice image. In another preferred embodiment, the radiologist may quickly jog through the individual ultrasound slices or may view a cine-loop presentation of them. In another preferred embodiment, side-by-side views of the individual ultrasound slices that form the thick-slice image are displayed. Advantageously, the individual ultrasound slices are of immediate and familiar significance to the radiologist because they correspond in orientation to standard x-ray mammogram views. In another preferred embodiment, the radiologist may directly view the raw, unprocessed ultrasound data from the ultrasound scans.

By way of analogy, the patient's breast may be thought of as a "book." An x-ray mammogram is a picture of the book with all of its pages clumped together. In contrast, each ultrasound slice is a picture of one page of the book. On the one hand, the x-ray mammogram alone often does not contain enough information, but on the other hand, separately screening each ultrasound slice would be both time-prohibitive and cost-prohibitive in today's mass screening environment. According to a preferred embodiment, if the x-ray mammogram alone is not sufficient, the radiologist may quickly glance at a simple array of thick-slice thumbnail images, which are analogous to "chapters" of the book. The radiologist only examines an individual page of the book if it lies within an interesting chapter. In this manner, the thoroughness afforded by volumetric ultrasound scans can be enjoyed in today's mass breast cancer screening environments without being time-prohibitive or cost-prohibitive.

According to another preferred embodiment, each thick-slice image is derived from B-mode ultrasound data, and vibrational Doppler imaging (VDI) data corresponding to each thick-slice image is superimposed thereon. The VDI data is superimposed only for those locations having at least a threshold amount of induced vibration resulting from the injected audio-frequency energy. For each such location, the B-mode data is displayed in ordinary fashion such as black-and-white, while the VDI data is superimposed thereon according to a color map that maps different amounts of induced vibration into different colors, lower amounts displayed in red, for example, up through higher amounts displayed in violet. In another preferred embodiment, the VDI data is displayed alone or in a separate image alongside the B-mode image. In another preferred embodiment, the radiologist may toggle among B-mode only, VDI only, superimposed B-mode/VDI, and side-by-side B-mode/VDI displays. For each of these options, the image may be expanded to a full-scale view comparable in size to the x-ray mammogram image, and may be jogged-through and/or cine-looped according to the desires of the radiologist.

According to a preferred embodiment, a method for mass breast cancer screening of a plurality of patients using adjunctive ultrasound mammography is provided comprising the steps of acquiring an x-ray mammogram for each of said plurality of patients, acquiring raw breast ultrasound scans for each of said plurality of patients, processing the raw breast ultrasound scans into adjunctive ultrasound data including viewable thick-slice images, and storing the adjunctive ultrasound data on an adjunctive ultrasound server. In one preferred embodiment in which the raw ultrasound slices are acquired in planes parallel or nearly parallel to the desired standard x-ray mammogram view plane, the thick-slice images are directly computed from an integration of the raw ultrasound slices. In another preferred embodiment in which the raw ultrasound slices are acquired in planes perpendicular or substantially non-parallel to the desired standard x-ray mammogram view plane, the thick-slice images are indirectly computed by construction of a three-dimensional volumetric representation of the breast and extraction of the thick-slice images therefrom.

The method further comprises the steps of, for each patient, associating the adjunctive ultrasound data with the corresponding x-ray mammogram for that patient. In one preferred embodiment, an alphanumeric identifier (e.g., bar code) of the x-ray mammogram is directly assigned to the adjunctive ultrasound data. The method further comprises the steps of performing en masse screening of the x-ray mammograms for the plurality of patients. For each x-ray mammogram presented to the radiologist, the alphanumeric identifier thereof is used to retrieve the associated adjunctive ultrasound data from the adjunctive ultrasound server to facilitate screening of that x-ray mammogram. According to another preferred embodiment, the adjunctive ultrasound data is assigned a fixed patient ID for that patient and a date stamp. During en masse screening, a patient ID from the x-ray mammogram is used to query the adjunctive ultrasound server, which returns the most recent set of adjunctive ultrasound data for that patient ID.

Advantageously, because they generally exhibit improved signal-to-noise ratios as compared to their component individual ultrasound slices, the thick-slice images are more conducive to the use of two-dimensional computer-assisted diagnosis (CAD) algorithms to assist the radiologist. According to a preferred embodiment, two-dimensional CAD algorithms are applied to the thick-slice images similar to a manner in which conventional two-dimensional CAD algorithms are applied to digitized x-ray mammograms. Results from the two-dimensional CAD algorithms are superimposed on the thick-slice image display in a manner that highlights the location of possible tumors and their degree of suspiciousness. The preferred two-dimensional CAD algorithm comprises the steps of (i) determining region-of-interest (ROI) locations in the thick-slice image according to a two-dimensional ROI detection algorithm, (ii) segmenting the borders of candidate lesions at each ROI location, (iii) for each candidate lesion, extracting a first set of two-dimensional features, the first set of two-dimensional features being selected from known x-ray CAD methods, and (iv) applying a classifier algorithm to the first set of two-dimensional features to determine one or more metrics of suspiciousness therefrom. Examples of such known two-dimensional features include spiculation metrics, density metrics, eccentricity metrics, and sphericity metrics. In one preferred embodiment, a single scalar metric of suspiciousness, termed a score, is generated for each candidate lesion.

According to another preferred embodiment, for each candidate lesion a second set of two-dimensional features is extracted in addition to the first set of two-dimensional features, the second set of two-dimensional features being directly associated with acoustical characteristics of the breast. The second set of two-dimensional features may include any combination of (i) a lateral shadow metric, (ii) a VDI metric, (iii) a vertical shadow metric, and (iv) a posterior enhancement metric. For a given candidate lesion on a given thick-slice image, the lateral shadow metric relates to an amount of acoustic shadow cast by that lesion across that thick-slice image, and becomes relevant where the interrogating ultrasound beam is substantially parallel to that particular thick-slice portion of the breast volume. The vertical shadow metric relates to an amount of acoustic shadow cast by that lesion across other thick-slice images, and becomes relevant where the ultrasound probe is substantially non-parallel to the thick slices. In one preferred embodiment, the VDI metric is simply an average magnitude of measured velocity in a neighborhood of the lesion, wherein a lesser VDI metric indicates higher suspiciousness. The classifier algorithm then operates on both the first set and second set of two-dimensional features to determine a score, or other metric of lesion suspiciousness, for that candidate lesion.

According to another preferred embodiment, in conjunction with the determination of two-dimensional features from the thick-slice images, three-dimensional features are extracted from a three-dimensional thick-slice volume corresponding to each thick-slice image. In one preferred embodiment, the three-dimensional features are determined by (i) determining region-of-interest (ROI) locations in the thick-slice volume, (ii) segmenting the borders of candidate lesions at each ROI location, and (iii) extracting a set of three-dimensional features for each candidate lesion. Preferably, the ROI location step takes advantage of the known two-dimensional ROI locations computed for the thick-slice images, for example, by using them as starting points in locating the three-dimensional ROI locations within the thick-slice volume. This can save computing time by reducing the ROI search to a one-dimensional search for each known two-dimensional ROI location. In an alternative preferred embodiment, a purely three-dimensional ROI location algorithm is used to locate the ROIs in the thick-slice volume. In one preferred embodiment, the three-dimensional features comprise a surface roughness metric for the candidate lesions, such as a surface area-to-volume ratio. The classifier algorithm then operates on the set of three-dimensional features, together with the first and second sets of two-dimensional features, to determine a score, or other metric of lesion suspiciousness, for each candidate lesion. The classifier algorithm may incorporate any of a variety of classification algorithms known in the art, including linear classifier algorithms, quadratic classifier algorithms, K-nearest-neighbor classifier algorithms, decision tree classifier algorithms, or neural network classifier algorithms.

According to another preferred embodiment, three-dimensional CAD algorithms are performed on a volumetric representation of the breast without regard to thick-slice boundaries, including the steps of the steps of (i) determining ROI locations in the breast volume according to a three-dimensional ROI detection algorithm, (ii) segmenting the borders of candidate lesions at each ROI location, (iii) for each candidate lesion, extracting three-dimensional features, and (iv) applying a classifier algorithm to the three-dimensional features to determine one or more metrics of suspiciousness therefrom. The locations of lesions found to require user attention are mapped from the breast volume into their corresponding thick-slice image, and a marker is placed on the two-dimensional thick-slice image on the user display. The marker may also be placed on the relevant individual ultrasound slices on the user display. The three-dimensional features may include three-dimensional spiculation metrics, three-dimensional density metrics, sphericity metrics, VDI metrics, shadow metrics, surface area-to-volume metrics, and other three-dimensional metrics.

According to another preferred embodiment, a computer-assisted microcalcification-highlighting algorithm is provided for assisting viewer perception of microcalcifications on the thick-slice images and/or individual ultrasound slices. The image is first thresholded on a pixel-by-pixel basis using a predetermined threshold value selected to separate the microcalcifications from the dense breast tissue and other breast tissue in a statistically reliable manner. For those pixels lying above the predetermined threshold, simple region-growing algorithms are performed in which neighboring above-threshold pixels are clustered together. An overlay display comprising those clusters having an average diameter less than a predetermined size, such as about 1 mm, are overlaid in a bright color on the otherwise black-and-white ultrasound image.

According to another preferred embodiment, a breast cancer screening CAD system is provided that performs a first set of CAD algorithms on a digitized x-ray mammogram view of the breast, performs a second set of CAD algorithms on a corresponding set of adjunctive ultrasound views, correlates regions of interest (ROIs) between the x-ray mammogram view and the adjunctive ultrasound views, and performs joint classification of the ROI using both the x-ray CAD results and the ultrasound CAD results. During the ROI correlation process, ROIs in the x-ray mammogram are matched to corresponding ROIs in the adjunctive ultrasound views in a manner that obviates the need for complex registration computations. Rather, a simplified but statistically reliable lesion-centric correlation process using nipple distance information, or using a combination of nipple distance information and nipple angle information, is used to match corresponding ROIs in the x-ray mammogram view and the adjunctive ultrasound views. In another preferred embodiment, the correlation process also uses lesion size as a factor in matching corresponding regions of interest in the x-ray mammogram view and the adjunctive ultrasound views. In still another preferred embodiment, the correlation process uses lesion distance from the chest wall as a factor in matching corresponding regions of interest in the x-ray mammogram view and the adjunctive ultrasound views. In one preferred embodiment, the joint classification algorithm comprises a direct addition of scalar suspiciousness metrics taken from the x-ray CAD results and the ultrasound CAD results.

BRIEF DESCRIPTION OF THE DRAWINGS

FIGS. 27-31 illustrate conceptual diagrams of thick-slice regions as superimposed onto a front view of a breast;

DETAILED DESCRIPTION

Figure 1:
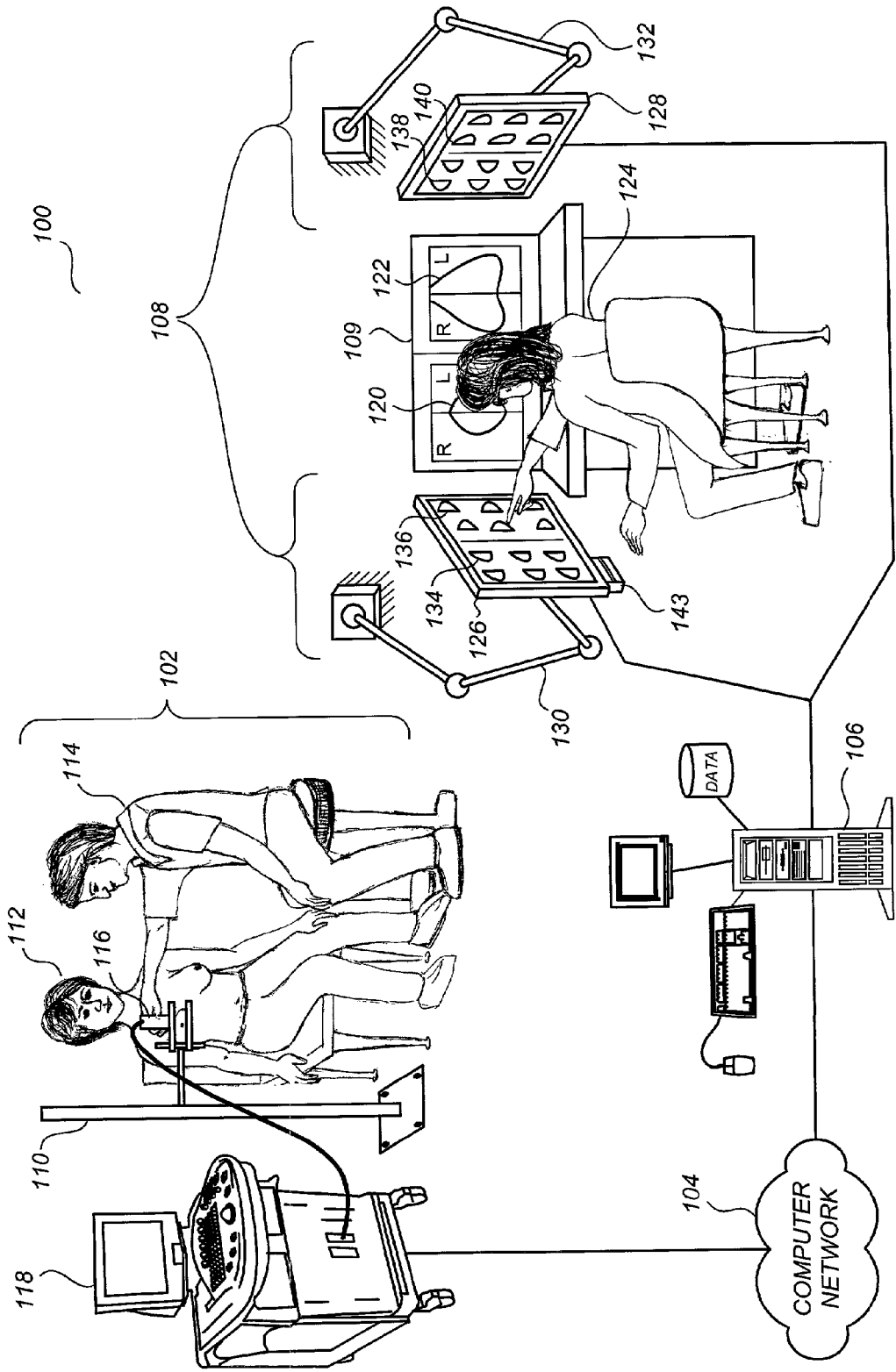
FIG. 1 illustrates a conceptual diagram of a system and method for breast cancer screening using adjunctive ultrasound mammography according to a preferred embodiment.

FIG. 1 illustrates a conceptual diagram of a system 100 and associated methods for breast cancer screening using adjunctive ultrasound mammography according to a preferred embodiment. Adjunctive ultrasound mammography refers to the acquisition and display of breast ultrasound information during the breast cancer screening process in a manner that supplements x-ray mammogram information. System 100 comprises an ultrasound scanning station 102, a computer network 104, an adjunctive ultrasound server 106, and an adjunctive ultrasound screening station 108. Ultrasound scanning station 102 comprises an ultrasound scanning apparatus 110 for facilitating breast ultrasound scans of the patient 112 by an ultrasound technician 114. An ultrasound probe 116 is used to scan a breast of the patient 112, with reflected acoustic interrogation signals being processed by an ultrasound machine 118.

The ultrasound scanning apparatus 110 supports and maintains the breast during the ultrasound scanning process. According to a preferred embodiment, the ultrasound scanning apparatus 110 also flattens the breast along a plane parallel to a standard x-ray mammogram view plane such that resulting ultrasound images can match more closely standard x-ray mammogram images. In the example of FIG. 1, the standard x-ray mammogram view is the craniocaudal (CC) view. While described herein with respect to the CC view for simplicity and clarity of explanation, it is to be appreciated that the preferred embodiments are readily applied to the mediolateral oblique (MLO) view or to standard or custom x-ray mammogram views.

Although not shown in FIG. 1, the patient 112 also undergoes a standard x-ray mammography procedure in addition to the ultrasound mammography procedure. The x-ray mammogram is usually taken during the same office visit as the ultrasonic mammography scans, although the scope of the preferred embodiments is not so limited. The ultrasound technician 114 may be the same person or a different person as the x-ray technician who performs the x-ray mammography procedure.

If the ultrasound probe 116 is manipulated by hand, as in the embodiment of FIG. 1, a position sensing system (not shown) is used to track the probe position such that the acquired ultrasound frames may be processed into a three-dimensional volumetric representation of the breast. It is generally preferable, however, that the ultrasound probe 116 be machine-manipulated and controlled so as to provide reliable, consistent ultrasound scans. The ultrasound scans should be of sufficient resolution and taken at small enough intervals such that the three-dimensional volumetric representation has sufficient resolution to enable computer-aided diagnosis (CAD) algorithms to perform effectively, and such that both individual ultrasound slices and thick-slice images are of sufficient resolution to enable meaningful screening assistance to the radiologist.

As will be described further infra, the raw ultrasound scans may be taken directly in the standard x-ray mammogram view plane, or may alternatively be taken from a different orientation. When the raw ultrasound scans are taken directly in the standard x-ray mammogram view plane, each individual ultrasound slice is computed directly from an acquired two-dimensional ultrasound image or ultrasound frame. When the raw ultrasound scans are taken from a different orientation, each individual ultrasound slice corresponds to a plane of voxels (volume elements) in a three-dimensional volumetric representation of the breast, the plane of voxels being oriented in a direction parallel to the standard x-ray mammogram view plane. Most commonly, the three-dimensional volumetric representation of the breast is computed from the raw ultrasound scans, and then the individual ultrasound slice is extracted therefrom. However, in other preferred embodiments such as those described in Ser. No. 60/326,715, supra, it is not always necessary to reconstruct the entire three-dimensional volumetric representation to compute the individual ultrasound slices. Stated more generally, if the raw ultrasound scans are taken in planes directly parallel to a plane of interest (CC, MLO, or a different "custom" plane of importance), each individual ultrasound slice is computed directly from an acquired two-dimensional ultrasound image or ultrasound frame, whereas if the raw ultrasound scans are taken from directions different than the plane of interest, each individual ultrasound slice corresponds to a plane of voxels in a three-dimensional volumetric representation of the breast in a direction parallel to the plane of interest.

Ultrasound machine 118 may generally comprise any commercially available ultrasound machine having sufficient resolution, speed, and network connectivity to achieve the functionalities described herein. In one preferred embodiment, ultrasound machine 118 comprises a system available from U-Systems, Inc. of San Jose, Calif. Preferably, ultrasound probe 116 is of sufficient width (e.g., 15 cm) to scan the entire flattened breast surface in a single sweep. If a smaller probe (e.g., 7.5 cm) is used for cost-containment reasons or other practical reasons, the ultrasound probe 116 is swept across two or more times until the entire breast surface is scanned.

During or after the ultrasound scanning process, the raw ultrasound data is provided across the computer network 104 to the adjunctive ultrasound server 106, where the raw ultrasound data is processed into adjunctive ultrasound data that will be made available to the screening radiologist, the adjunctive ultrasound data including ultrasound slices, thick-slice images, vibrational Doppler imaging (VDI) images, CAD outputs, and other useful information. It is to be appreciated that the processing of the raw ultrasound data into the adjunctive ultrasound data may be performed by any of a variety of different computing devices coupled to the computer network 104 and then transferred to the adjunctive ultrasound server 106.

In current mass breast cancer screening environments based on x-ray mammography, a typically screening radiologist 124 examines x-ray mammograms for many patients en masse in a single session using an x-ray viewing station 109. The x-ray viewing station 109 may range from a simple light box, as in FIG. 1, to more complex x-ray CAD workstations that automatically move the x-ray mammograms past the radiologist 124 on a conveyor belt as a nearby CAD display highlights suspicious areas of the mammogram. Almost universally, left and right CC x-ray views 120 are positioned on one side of the x-ray viewing station 109, and left and right MLO x-ray views 122 are positioned on the other side. The radiologist 124 quickly examines the x-ray mammograms. For some x-ray mammograms the radiologist needs only a few seconds, while for other x-ray mammograms the radiologist needs a few minutes, e.g. up to five minutes, with an average being about two minutes per mammogram.

According to a preferred embodiment, this existing arrangements remains substantially as currently used, but is augmented with equipment and data that facilitates fast and thorough x-ray mammogram screening by giving the radiologist a quick ultrasonic "second look" at the internal breast structure. Adjunctive ultrasound screening station 108 comprises an adjunct display 126 conveniently positioned near the x-ray viewing station 109 such that the radiologist 124 can easily look back and forth between the adjunct display 126 and the x-ray mammograms 120 and 122. Thumbnail representations 134 and 136 of thick-slice images are displayed. Generally speaking, a thick-slice image results from combining, e.g. by integration, a plurality of substantially parallel individual ultrasound slices used to represent a slab-like or thick-slice volume of the breast. The thickness of the slab-like or thick-slice volume may lie, for example, in the range of 2 mm to 20 mm, although the scope of the preferred embodiments is not so limited. Techniques for integrating the component ultrasound slices into thick-slice images according to the preferred embodiments include arithmetic averaging, geometric averaging, reciprocal averaging, exponential averaging, and other averaging methods, in each case including both weighted and unweighted averaging techniques. Other suitable integration methods may be based on statistical properties of the population of component ultrasound slices at common locations, such as maximum value, minimum value, mean, variance, or other statistical algorithms.

Preferably, the thick-slice images correspond to slab-like or thick-slice volumes of the breast having a thickness related to the size of the lesions to be detected. A larger thickness of 20 mm, for example, may be used if it is desirable to overlook most of the breast details and direct the user's attention to larger features on the order 10 mm in size. A smaller thickness of 3 mm, for example, may be used if it is desirable to view small, low-contrast lesions on the order of 2 mm in size. Thicknesses in the range of 7 mm-12 mm are likely to be suitable for most breast cancer screening purposes.

For even quicker reference, a second adjunct display 128 is provided to form an adjunct display pair, each side corresponding to the nearest mammogram view being displayed at x-ray viewing station 109. A bar code reader 143 reads a bar code of the x-ray mammogram, wherein the associated adjunctive ultrasound data for that breast is automatically retrieved from the ultrasound server 106 and displayed on the adjunct displays 126 and 128.

By way of example and not by way of limitation, where the x-ray mammogram 120 represents the craniocaudal (CC) x-ray view for right and left breasts, respectively, the thumbnail thick-slice images 134 and 136 represent thick-slice portions of the right and left breast volumes, respectively, preferably oriented parallel to the CC view plane. Where the x-ray mammogram 122 represents the mediolateral oblique (MLO) x-ray view for right and left breasts, respectively, thumbnail thick-slice images 138 and 140 displayed on adjunct display 128 represent thick-slice portions of the right and left breast volumes, respectively, preferably oriented parallel to the MLO view plane.

Each thick-slice image usually represents between 0.5 cm to 1.0 cm of breast thickness. It has been found that this thickness range yields good results in assisting in the recognition of tumors that are of concern in the breast cancer screening process, which are about 0.5 cm or greater in diameter with an average diameter of about 1.2 cm. Also, because the flattened breast is usually somewhere between 4 cm and 6 cm thick, it has been found that the preferred 0.5 cm-1.0 cm thickness dimension facilitates an easy "single-glance" view of the entire breast, with a simple display of six to eight thick-slice images covering the entire breast volume. This is clearly advantageous over ultrasonic screening methods that examine one ultrasound slice at a time, in which case it would take up to 500 ultrasound slices or more to cover the entire breast volume. Although a 0.5-1.0 cm slab thickness and a 6-8 image layout has been found to yield good results, it is to be appreciated that the scope of the preferred embodiments is not so limited, and that a wide range of slab thicknesses and images-per-layout are within the scope of the preferred embodiments.

Each adjunct display 126 and 128 is flexibly mounted using adjustable mountings 130 and 132 such that the radiologist 124 may freely move them into different positions near the x-ray mammogram views to facilitate optimal back-and-forth viewing. It has been found that ideal back and forth viewing is facilitated where each thick-slice image is not more than about 20 inches from its corresponding x-ray mammogram image.

Preferably, the adjunct displays 126 and 128 comprise touchscreen monitors. When the radiologist 124 presses one of the thumbnail thick-slice images, a larger thick-slice image is displayed. In one preferred embodiment, the larger thick-slice image has a size identical or close to that of the x-ray mammogram image for further facilitating back-and-forth image comparisons. A control panel (not shown in FIG. 1 but described further infra) is positioned near or integrated with each adjunct display 126 and 128 that provides a user interface for the radiologist 124. In conjunction with the touchscreen display, the control panel permits quick manipulation and examination of the thick-slice images in a manner that facilitates rapid screening. By way of example, the radiologist 124 is permitted to examine each individual component slice, or subset of slices, of any thick-slice image, jogging through the individual ultrasound slices or subsets or viewing a cine-loop representation. Also, as will be described further infra, the radiologist may flexibly overlay useful information onto the displayed thick-slice or other images such as vibrational Doppler image (VDI) outputs and computer-aided diagnosis (CAD) outputs.

Thus, an adjunctive ultrasound system according to the preferred embodiments does not supplant existing x-ray mammogram screening methods. Indeed, reference to the adjunctive ultrasound data is optional depending on the contents of the x-ray mammogram image, and for many patients it may not even be used at all. Rather, the adjunctive ultrasound system is there to assist the radiologist in performing their pre-existing professional duties with respect to "difficult" or "marginal" mammograms. As such, a medical establishment faces little risk of failure in acquiring an adjunctive ultrasound system according to the preferred embodiments. In a worst-case scenario, the adjunctive ultrasound system would be met with indifference by the entrenched "x-ray-only" believers, because it would not require them to alter their pre-existing routines. However, the adjunctive ultrasound system will be there standing by to assist in the "difficult" cases, and it is expected that even the "x-ray-only" believers will eventually find the system useful and will increasingly rely on it to increase their sensitivity and specificity performance.

Figure 2:
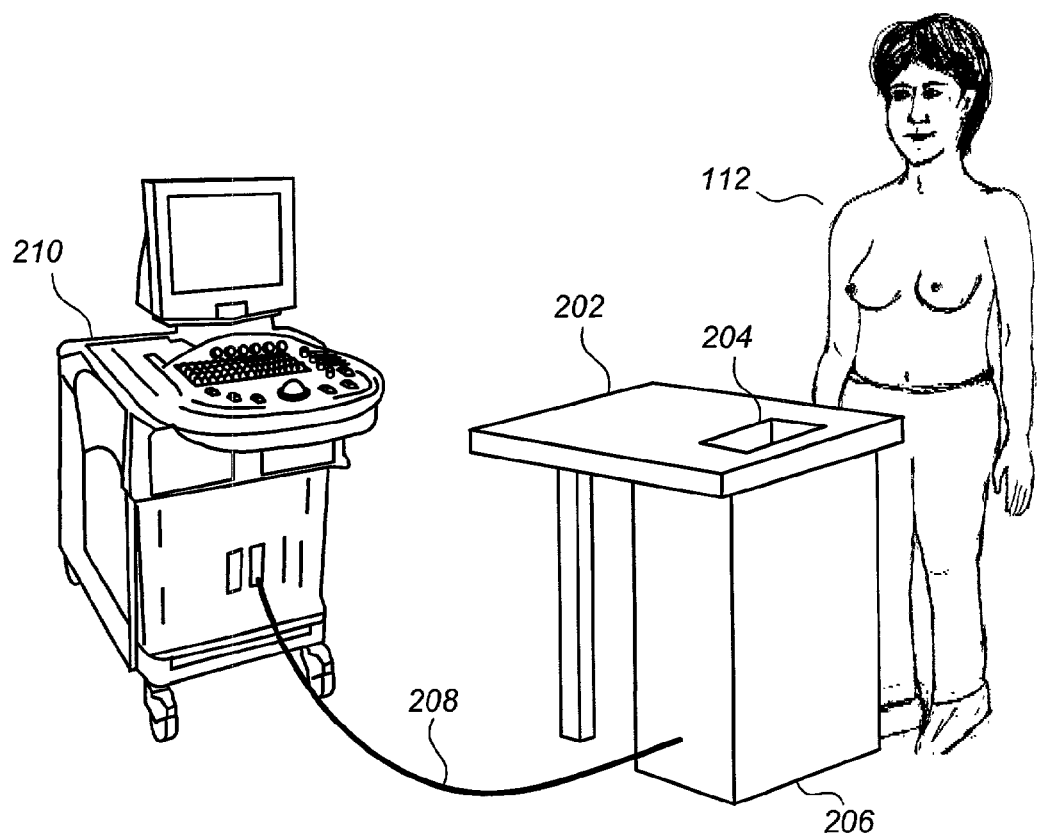
FIG. 2 illustrates a perspective view of an ultrasound scanning apparatus according to a preferred embodiment.
Figure 2:
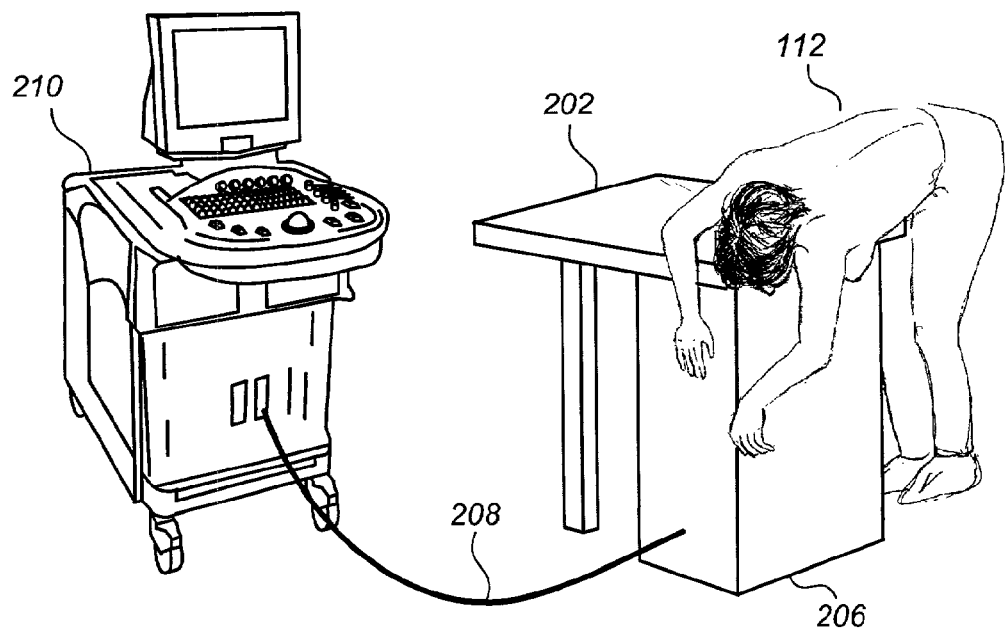

FIG. 2 illustrates an ultrasound scanning apparatus 202 according to a preferred embodiment, comprising a chamber 204 contained in a housing 206. The chamber 204 is configured to receive a breast at an open end, and further contains an acoustically conductive liquid such as water or an ultrasonic gel for facilitating acoustic coupling between an ultrasound probe (not shown) contained in the housing 206 and the breast. The ultrasound probe is connected by a lead 208 through housing 206 to an ultrasound system 210. A mechanical apparatus within housing 206, which is described further with respect to FIG. 3 below, translates the ultrasound probe during the scanning process. As shown in FIG. 2, the chamber 204 is positioned at approximately the waist level of the patient 112, who bends over to position the breast therein.

Figure 3:
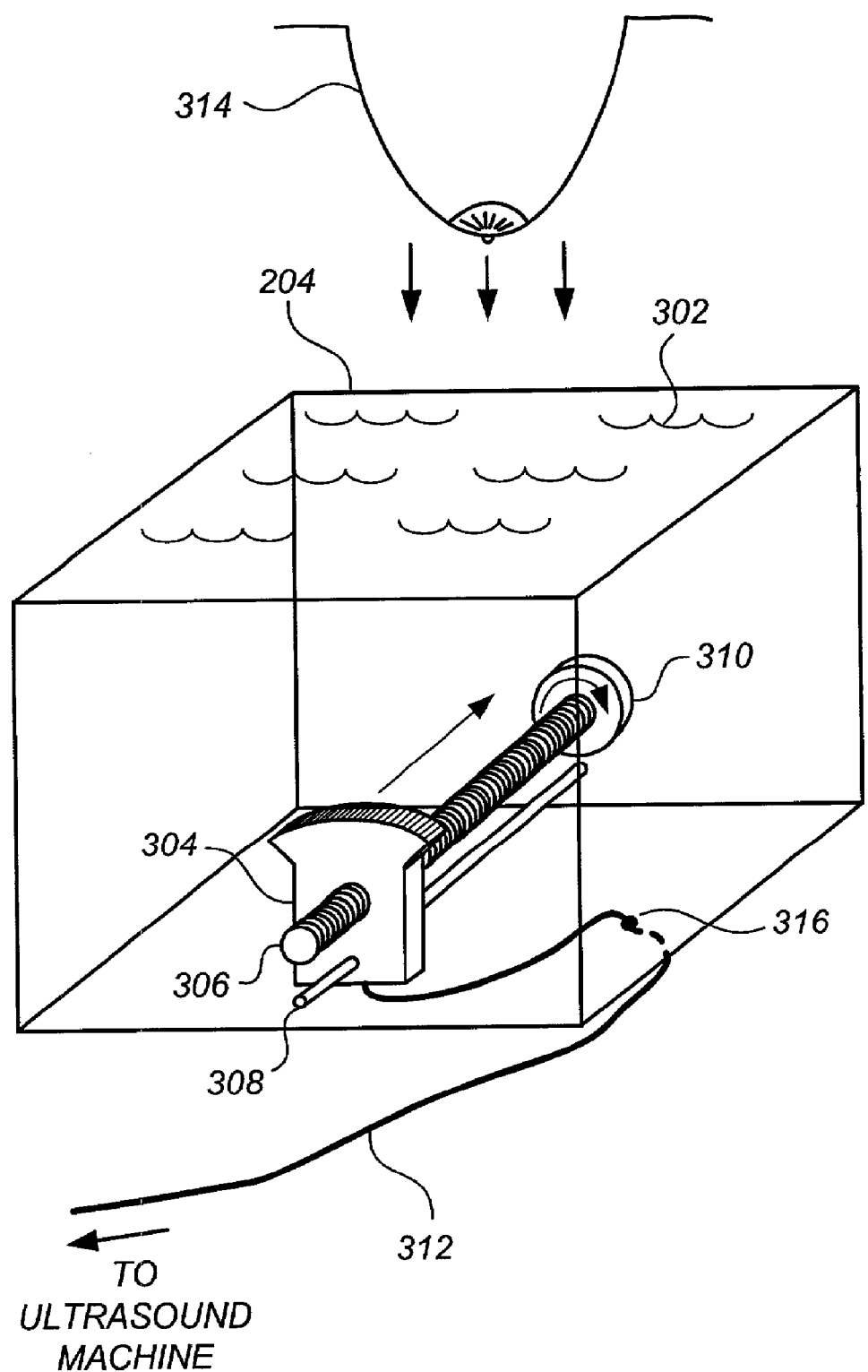
FIG. 3 illustrates a conceptual perspective view of a reservoir portion of an ultrasound scanning apparatus according to a preferred embodiment.

FIG. 3 illustrates a conceptual perspective view of the chamber 204 of FIG. 2. An ultrasound probe 304 is submerged beneath the surface of a liquid 302 and scans a breast 314 after the breast is immersed. A worm gear 306 is driven by a motor 310 to increment the position of the probe 304 as the ultrasound scans are taken. A probe lead 312 connects the ultrasound probe 304 to an ultrasound machine through a sealed hole 316. If the patient is in a first relative orientation with respect to the chamber 204 that yields a CC view, the relative orientation is simply shifted by roughly 45-80 degrees (e.g., by shifting the patient and/or the chamber) to obtain the MLO view, and vice-versa. To obtain another standardized x-ray mammogram view termed the lateral (LAT) view the relative orientation is shifted by about 90 degrees. The use of chamber 204 provides an advantage that the raw ultrasound slices are inherently parallel to a standard x-ray mammogram view, which obviates the need for three-dimensional volumetric reconstruction in generating the thick-slice images. Although less processing is needed, this "direct" approach requires a substantial penetration depth to penetrate from the front of the breast to the chest wall, and so a lower frequency probe (e.g., 3.5 MHz or less) is required. The raw ultrasound slices therefore have less spatial resolution as compared to a scenario in which higher frequency probes are used.

By way of example and not by way of limitation, B-mode ultrasound frames may be acquired at a rate of about 10 frames per second (fps) as the ultrasound probe is translated at a constant rate of about 1.5 mm/sec across the breast. For an uncompressed breast, the ultrasound probe 304 may require a translation distance of about 7 cm-9 cm in order to capture the entire breast volume, which takes between 45-60 seconds. This yields from 450 to 600 raw ultrasound slices which, when processed into 1.0 cm thick-slice portions, results in 7-9 thick-slice images for display.

According to another preferred embodiment, the scanning apparatus 202 is similar to one or more scanning apparatuses described in the following references, each of which is hereby incorporated by reference: U.S. Pat. No. 4,167,180; U.S. Pat. No. 4,298,009; U.S. Pat. No. 4,485,819; and WO02/17792A1. Between patients, the fluid 302 should be drained and replaced to prevent inter-patient contamination and fomite propagation. In one preferred embodiment, the fluid drainage and replacement system is similar to that described in U.S. Pat. No. 4,282,880, which is incorporated by reference herein.

Figure 4:
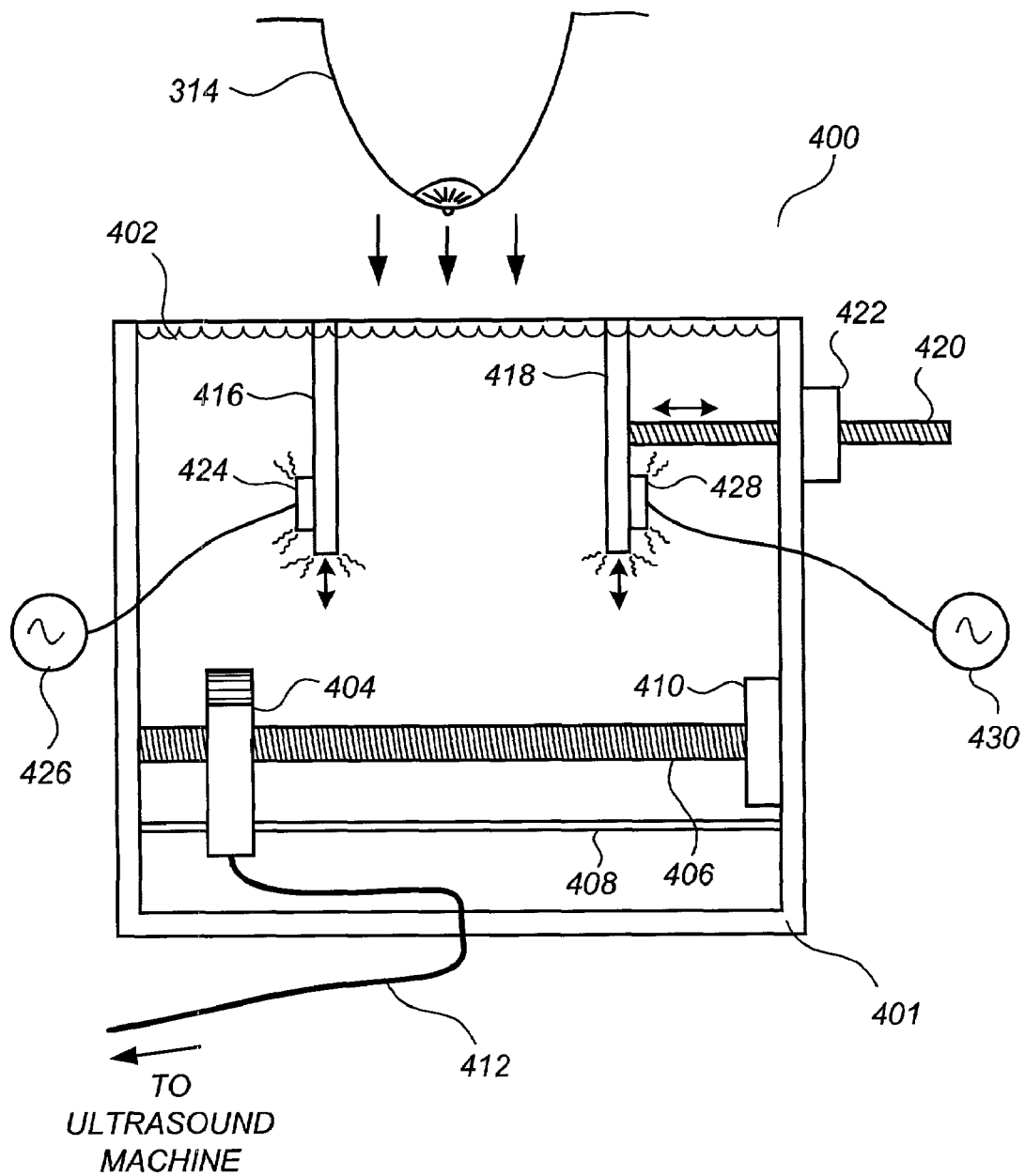
FIG. 4 illustrates a conceptual side view of a reservoir portion of an ultrasound scanning apparatus according to a preferred embodiment.

FIG. 4 illustrates a conceptual perspective view of a chamber 400 of an ultrasound scanning apparatus in accordance with a preferred embodiment. The chamber 400 may be incorporated into the ultrasound scanning apparatus of FIG. 2 in place of the chamber 204. Generally speaking, the chamber 400 is similar to the chamber 204 but has (i) the additional ability to compress the breast along an x-ray mammogram view plane, and (ii) the additional ability to facilitate vibrational Doppler imaging (VDI).

Chamber 400 comprises a sealed inner housing 401 that contains a fluid 402, an ultrasound probe 404, a worm gear 406, a stabilizer bar 408, a motor 410, and probe lead 412 similar to elements 302-310 of FIG. 3, respectively. Additionally, however, chamber 400 comprises a fixed plate 416 and a movable plate 418 that compress the breast along an x-ray mammogram view plane. If the patient is in a first orientation with respect to the compression plates 416 and 418 that yields CC compression, the relative orientation can be changed by 45-80 degrees to achieve MLO compression, and vice-versa. This can be done by rotating the patient, rotating the chamber 400, or both. Movable plate 418 is actuated by a motor 422 via a worm gear 420. It is to be appreciated that the diagram of FIG. 4 is conceptual only, and that many different mechanical configurations to achieve such breast compression functionality may be used.

Chamber 400 further comprises audio frequency transducers 424 and 428 affixed to the compression plates 416 and 418, respectively. The audio frequency transducers 424 and 428 are shown as being separately driven by audio frequency sources 426 and 430, but may alternatively be driven by a common audio frequency source. In operation, the audio frequency transducers 424 and 428 cause the compression plates 416 and 418 to vibrate at one or more audio frequencies consistent with vibrational Doppler imaging (VDI) methods. Generally speaking, the audio frequencies of interest are in the range of 100 Hz to 1000 Hz, although other frequencies may be used. To obtain the VDI data, the ultrasound system is switched into power Doppler mode as the breast volume is being vibrated. In one preferred embodiment, the breast is vibrated simultaneously at audio frequencies of 100 Hz, 200 Hz, 300 Hz, and 400 Hz. A plurality of power Doppler frames are taken sufficient to compute an average magnitude of reflector velocity. Generally speaking, this average magnitude will be lower for hard, tumor-like tissue and higher for liquid or soft tissue.

Several different sequencing techniques for acquiring B-mode frames and VDI frames are within the scope of the preferred embodiments. In one preferred embodiment, a separate-sweep method is used in which the ultrasound probe acquires B-mode data during a first sweep of the breast, and acquires VDI data during a separate second sweep across the breast. Again by way of example and not by way of limitation, the B-mode frames may be acquired at a rate of about 10 fps as the ultrasound probe is translated at 1.5 mm/sec across the breast. For a compressed breast, the required translation distance is, e.g., about 4-6 cm to capture the entire breast volume, which takes between 25-40 seconds. This yields from 250 to 400 raw ultrasound slices which, when processed into 0.5-1.0 cm thick-slice portions, results in 8-12 thick-slice images. The audio frequency vibrations are turned off during the B-mode sweep and are turned on for the VDI sweep. For the VDI sweep, the ultrasound probe is preferably moved across the breast in a start-stop fashion in fixed increments of distance. It has been found that only a few VDI frames are needed per thick-slice image to meaningfully complement the B-mode scans, and so these fixed increments may be up to about 3 mm apart. At each increment, the probe is stopped, e.g., for about one second to capture a plurality of power Doppler frames sufficient to measure an average reflector velocity magnitude. The probe may be quickly moved between increments, e.g., at a rate of about 6 mm per second or faster, because there are no measurements being taken during this interval. The net translation rate of the probe is in this example therefore about 2 mm/sec, and so the VDI sweep takes on the order of 20-30 seconds to cover the breast volume. Accordingly, a combined time of between 45-70 seconds is required for the combined B-mode and the VDI sweeps. This calculation, of course, assumes that a wide probe (15 cm) is used. The required time interval is doubled if a narrower (7.5 cm) probe is used. If a conventional 4 cm probe is used, four sweeps would be required, and so on.

It is to be appreciated that the above numerical examples are presented by way of example only and not by way of limitation. For example, the raw B-mode ultrasound scans correspond to planes that are about 0.15 mm apart in the above example, and there are about 33 individual ultrasound slices per 0.5 cm thick-slice volume that are integrated into a single thick-slice image, or about 66 individual ultrasound slices per 1.0 cm thick-slice volume. The above example presumes that the raw B-mode ultrasound scans are taken parallel to the desired x-ray mammogram view plane, and therefore correspond directly to the individual component ultrasound slices used to generate the thick-slice images. In a more general scenario, the raw B-mode ultrasound scans are taken along planes different than the desired x-ray mammogram view plane, in which case it is necessary to construct a three-dimensional volumetric representation of the breast and to extract the individual component ultrasound slices therefrom. In the above example, the 0.15 mm spacing of the raw ultrasound scans corresponds generally to both the axial and lateral resolution of commercially available ultrasound probes/systems, which are commonly around 0.17 mm. In this exemplary preferred embodiment, the voxels of a three-dimensional volumetric representation of the breast derived from the raw ultrasound scans will have roughly the same resolution in all three directions. Accordingly, an individual ultrasound slice extracted from the three-dimensional volumetric representation will have roughly this same resolution in both directions. However, the scope of the preferred embodiments is not so limited, and the voxels of the three-dimensional volumetric representation can generally have different resolutions in different directions. In another example, the raw B-mode ultrasound scans correspond to planes that are about 0.75 mm apart (e.g., by translating the probe at 7.5 mm/sec for 10 fps B-mode acquisition). In this case, the voxels of the three-dimensional volumetric representation of the breast will have a larger resolution in one direction than the other, and accordingly the individual ultrasound slices will have different resolutions in different directions depending on their angle relative to the scan angle, ranging in this example from a maximum of about 0.17 mm/pixel and about 30 individual ultrasound slices per 0.5 cm thick-slice volume to a minimum of 0.75 mm/pixel and about 7 individual ultrasound slices per 0.5 cm thick-slice volume. These variations are readily compensated prior to display using any of a variety of known methods. In still another preferred embodiment, when the distance between scan planes is larger than the axial/lateral resolution limitations of the ultrasound system, the operating parameters of the ultrasound system are adjusted such that these axial/lateral resolutions correspond to the distance between scan planes, in which case the voxels of the derived from the raw ultrasound scans will again have roughly the same resolution in all three directions.

According to another preferred embodiment, an interlaced single-sweep method is used in which the B-mode frames and the VDI frames are taken in a single sweep of the probe across the breast, and in which the audio frequency vibrations are turned on at all times. The B-mode scans are taken as the ultrasound probe is moved between the discrete VDI scanning locations. By way of example, the B-mode frames may be acquired at a rate of about 10 fps as the ultrasound probe is translated at 1.5 mm/sec between VDI sampling increments that are about 3 mm apart, the probe being stopped for about one second to capture the Doppler data. This yields a net probe translation rate of about 1 mm/sec, and therefore the total required time for the scan is about 40-60 seconds, which is doubled if a narrow probe is used.

According to still another preferred embodiment, an interlaced single-sweep method is used in which the audio frequency vibrations are applied in a start-stop fashion, such that these vibrations are turned off during the B-mode frames and are turned on during the VDI frames. This technique is used where a single-sweep method is desired that avoids audio vibrations during B-scans, which may be necessary if excessive tissue movement occurs during the audio vibrations. In this preferred embodiment, sufficient time is needed at each VDI scanning location to (i) turn on the audio-frequency transducers, (ii) allow about 0.5 seconds for the tissues to begin vibrating, (ii) take the power Doppler measurements, (iv) turn off the audio-frequency transducers, and (v) allow about 0.5 seconds for the tissues to stop vibrating before resuming B-mode scans. Using a 1.5 mm/sec translation speed for the B-mode portions, this results in a net velocity of (3 mm)/(2+2 sec)=0.75 mm/sec. For a 4-6 cm translation distance, this results in an overall scanning time between 53-80 seconds, which is doubled if a narrow probe is used.

In the above the non-limiting example, each thick-slice image is associated with a plurality of corresponding VDI frames of data. These VDI frames may be arithmetically averaged together or otherwise integrated into a single thick-slice VDI frame for subsequent optional superposition onto the thick-slice images as described infra.

Figure 5:
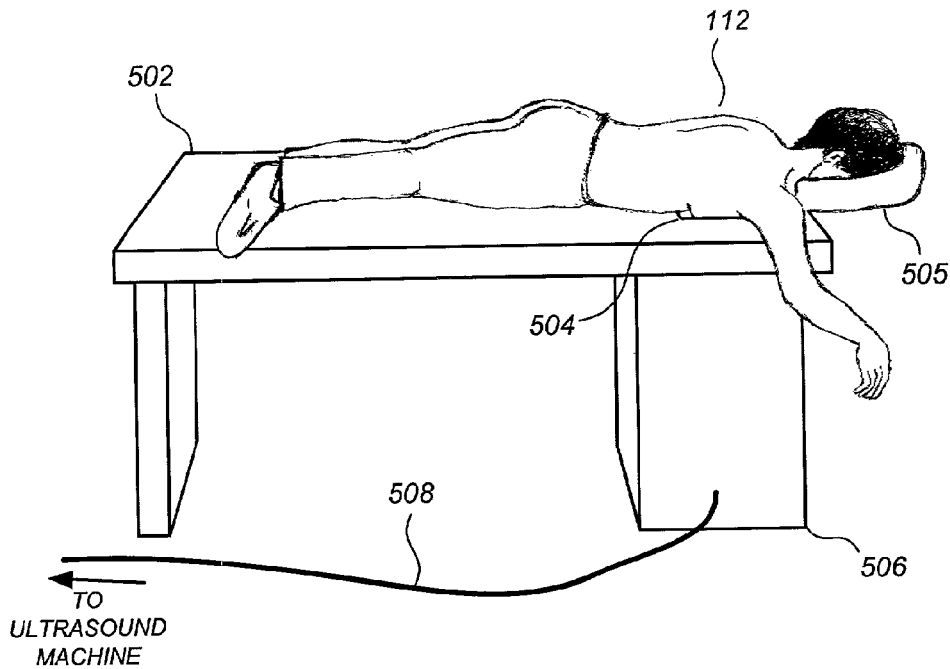
FIG. 5 illustrates a perspective view of an ultrasound scanning apparatus according to a preferred embodiment.

FIG. 5 illustrates a perspective view of an ultrasound scanning apparatus 502 according to another preferred embodiment. Ultrasound scanning apparatus 502 comprises a chamber 504 similar to the chamber 204 of FIG. 2 or the chamber 400 of FIG. 4, a chamber housing 506, and a probe lead 508 for coupling to an ultrasound machine. However, a table-like structure is provided that allows the patient 112 to lie face down during the procedure, their head resting comfortably in a headrest 505 similar to a headrest provided on a conventional massage table. Using means within housing 506 not shown in FIG. 5, the reservoir 504 is preferably rotatable around a central vertical axis such that compression along different standard x-ray mammogram view planes (CC/MLO) is allowed. A patient table for immersing a breast in liquid for x-ray CT examination is illustrated in U.S. Pat. Nos. 4,063,097, 4,015,836, and 3,973,126 hereby incorporated by reference.

Figure 6:
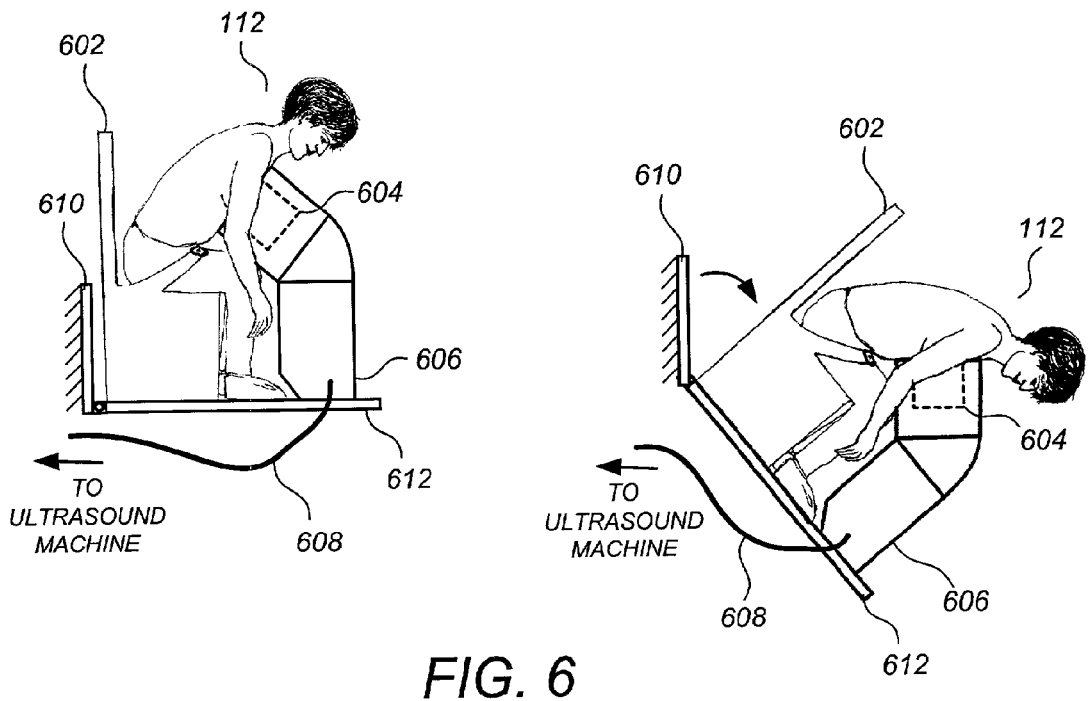
FIG. 6 illustrates side views of an ultrasound scanning apparatus according to a preferred embodiment in different patient positions.

FIG. 6 illustrates a perspective view of an ultrasound scanning apparatus 602 according to another preferred embodiment. Ultrasound scanning apparatus 602 comprises a chamber 604 similar to the chamber 204 of FIG. 2 or the chamber 400 of FIG. 4, a chamber housing 606, and a probe lead 608 for coupling to an ultrasound machine. However, a chair-based structure is provided that is mounted upon a forward-tiltable surface 612 that tilts forward respect to a base 610. In operation, the patient 112 is seated in the scanning apparatus 602 while the chamber 604 is devoid of fluid, and the patient gently leans against the housing 606. The entire scanning apparatus 602 is then tilted forward until the patient's chest wall is substantially horizontal and the breast is hanging down into the chamber 604. The chamber 604 is then filled with fluid, the breast is compressed by compression plates (see FIG. 4), and the scanning operation is initiated. After the scanning operation is complete, the chamber 604 is emptied of fluid and the scanning apparatus 602 is returned to its initial horizontal position.

Figure 7:
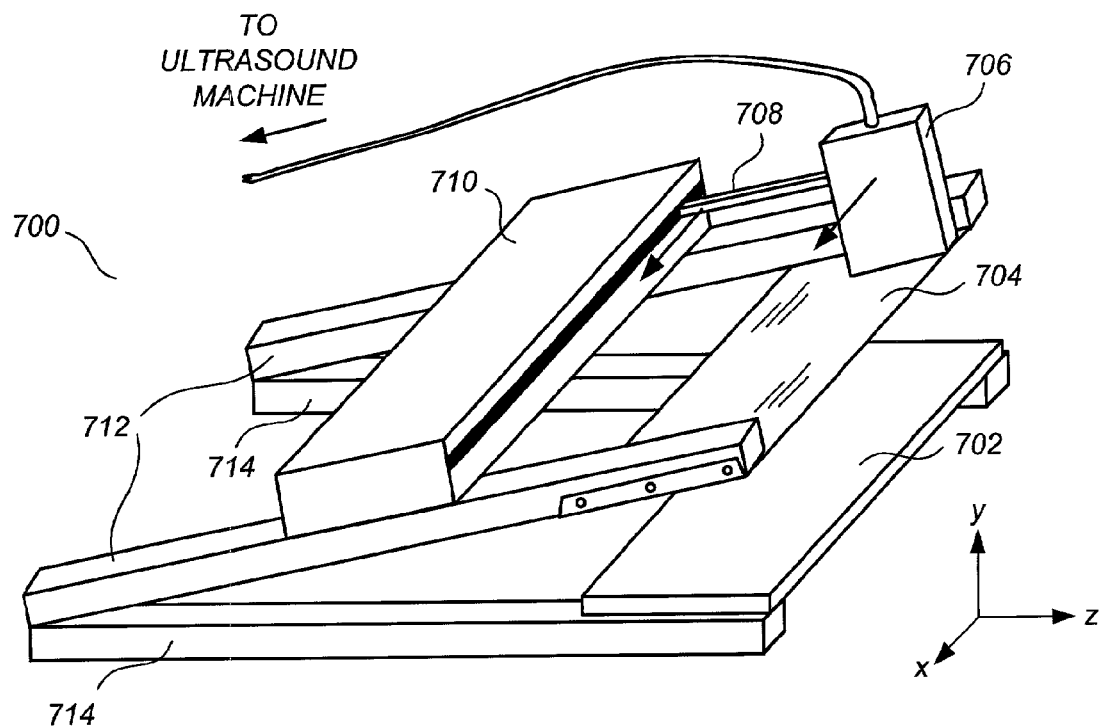
FIG. 7 illustrates a simplified perspective view of an ultrasound scanning apparatus according to a preferred embodiment.

FIG. 7 illustrates a perspective view of an ultrasound scanning apparatus 700 according to another preferred embodiment. Scanning apparatus 700 comprises an upper support frame 712 that is movable toward a lower support frame 714. It is not required that the upper and lower support frames be hingeably connected to each other, as implied in the configuration of FIG. 7, provided that they can ultimately be brought together to so as to compress the breast. A lower compressive member 702, comprising for example a stiff Buna-N rubber material, is supported by the lower support frame 714. An upper compressive member 704 comprising a taut, partially conformable sheet of acoustically transparent material such as Mylar® polyester film is stretched across, and supported by, the upper support frame 712. An ultrasound probe 706 coupled to an ultrasound machine is positioned over the polyester film 704 and is affixed to a rigid member 708, which is in turn coupled to an actuator 710 as shown. Preferably, the polyester film 704 is optically transparent so that the medical technical can see the breast from above as it is being compressed. Preferably, as is detailed further with respect to FIG. 8A below, ultrasound scanning apparatus 700 is configured and dimensioned such that lower compressive member 702 is at a shallow angle of about 10 degrees with respect to the horizontal. Also, the polyester film 704 preferably forms about a 5 degree angle with respect to the lower compressive member 702 when lowered to a distance of about 6 cm therefrom. While being shown between two lateral frame members in the embodiment of FIG. 7, the polyester film 704 can be framed on all sides in an alternative preferred embodiment.

The lower compressive member 702 is preferably positioned and maintained at a height that allows a standing patient to lay their breast thereon without crouching and such that their chest wall is substantially vertical. In operation, the polyester film 704 is generously coated on both sides with an ultrasonic gel, mineral oil, and/or water and lowered onto the breast. Although the polyester film 704 deforms by a small amount, a substantially horizontal surface is still provided for mechanical translation of the ultrasound probe 706 across the top surface thereof. Preferably, an overall compressive force similar to that applied during x-ray mammography, e.g. about 20-25 pounds, is applied by the polyester film 704. Between patients, the polyester film 704 is replaced and the lower compressive member 702 is sterilized or replaced to prevent inter-patient contamination and fomite propagation. As is common in the field, a small metallic object such as a small ball bearing or BB can be taped to the breast at a location corresponding to the nipple so that the nipple location is detectable in the acquired ultrasound images.

According to another preferred embodiment, the ultrasound probe 706 actually comprises two mechanically affixed side-by-side ultrasound probe heads, including a lower-frequency probe head and a higher-frequency probe head. Each probe head is connected to a different probe input of the ultrasound machine, which is capable of being controlled by the ultrasound technician so as to selected one probe head or the other. According to a preferred embodiment, the lower-frequency probe is used for patients with large breasts, while the higher-frequency probe is used for patients with medium or small breasts. The lower-frequency probe operates at lower frequencies, e.g. 5-7 MHz, for enabling deeper scans for the larger breast, e.g. as deep as 10 cm, albeit at a somewhat reduced resolution. The higher-frequency probe operates at higher frequencies, e.g. 8-12 MHz, which penetrates only to the shallower depths of 4-6 cm, but which provides higher resolution than the lower-frequency probe. In an alternative preferred embodiment, large breasts are scanned in a two-sweep process, the first sweep being high-frequency and the second sweep being low-frequency, and the near field portions of the images resulting from the first sweep are stitched to the far field portions of the images resulting from the second sweep.

In still another alternative embodiment, the lower compressive member 702 is replaced by a lower film/probe/actuator assembly ("lower assembly") that mirrors the upper film/probe/actuator assembly 704/706/708/710 ("upper assembly"). The lower assembly is similar to the upper assembly, and both are equipped with higher-frequency ultrasound probes. When small or medium breasts are presented, only the upper assembly actively scans the breast, and the lower assembly remains dormant, that is, it serves the function of a lower compressive member but does not actively scan the breast. However, when a large breast is presented, a first sweep of the upper assembly and a second sweep of the lower assembly are executed. The near-field portions of the images resulting from the first and second sweeps, which collectively scan the entire large breast volume, are then stitched together.

According to another preferred embodiment, the ultrasound probe 706 actually comprises two mechanically affixed end-to-end ultrasound probe heads, each having a shorter length individually (e.g., 7.5 cm) but, when placed end-to-end, forming a larger effective probe head (e.g., 15 cm). In one preferred embodiment, the first probe head is operative on a first sweep across the breast, while the second probe is operative on a second sweep. An A-B switch is provided in the ultrasound machine for automatically switching between the probe heads. In another preferred embodiment in which only a single sweep is required, the probe heads operate sequentially at non-overlapping time intervals for each ultrasound slice during the sweep. The resulting separate ultrasound frames are stitched together using known methods. Generally speaking, acquiring two shorter end-to-end probe heads is less expensive than acquiring a single long probe head. This can be appreciated with respect to transducer element yields during probe manufacture. Other factors being equal, if a single 7.5 cm transducer can be made with a 90% element yield, a 15 cm transducer may only have a 90%×90% or 81% element yield, with associated higher manufacturing costs.

In still another preferred embodiment, an irrigation mechanism (not shown) is provided that maintains a stream of nonviscous, acoustically transparent fluid such as water at an interface between the thin film 704 and the ultrasound probe 706 during the ultrasound scans, thereby enhancing the acoustic coupling between said ultrasound probe 706 and the breast. In still another preferred embodiment, one or more audio frequency transducers (not shown) are affixed to one or more of the lower compressive member 702 and the thin film 704 for inducing audio frequency vibrations in the breast during the ultrasound scans according to a vibrational Doppler imaging (VDI) modality.

In yet another preferred embodiment, the upper support frame 712 is springably and hingeably mounted with respect to the lower support frame 714 such that the polyester film 704 may adaptably tilt forward or backward in the anterior/posterior direction relative to the patient as it compresses the breast to obtain a best compression angle. Visualized with respect to FIG. 7, the springable, hingeable tilting would take place around an axis parallel to the "x" axis, and that axis of rotation would itself be movable in the "y" direction and, to a lesser extent, in the "z" direction. Such a device would provide enhanced compression for a wider variety of breasts that have differing profiles in the y-z plane of FIG. 7. In one preferred embodiment, the device is similar to a commercially available conforming compression device used for x-ray mammography, termed the FAST Paddle (Fully Automatic Self-adjusting Tilt Compression Paddle), available from LORAD, a Hologic Company, of Danbury, Conn., and described on their public web site.

In still another preferred embodiment, a gap-filling gel bag or other flexible bag containing an acoustically transparent fluid such as water, gel, mineral oil, or the like is positioned above the breast prior to compression by the polyester film 704. This enhances imaging of those breast portions corresponding to upper skin locations that may not come directly into contact with the polyester film 704 during compression. The gap-filling bag surface may comprise latex, Nitrile, Saran Wrap, cellophane, or other suitable material. Alternatively, the gap filling material may be a highly conformable cross-linked polymer gel (or a "slime" material often used in children's toys) having appreciable acoustic transmissivity but requiring an outer bag.

In yet another preferred embodiment, the polyester film 704 is replaced by a stiffer plastic material such as PETG. The stiffer plastic material does not require taut placement across frame members, but rather is vacuum-formed into a structure having a flat bottom surrounded by elevated outer ridges. The elevated outer ridges are affixed to the frame members. When the structure is pressed down onto the breast, a lower surface of the flat bottom compresses the breast, and the ultrasound probe is swept across an upper surface of the flat bottom. Substantial force is applied to the breast by virtue of the stiffness of the flat bottom material as strengthened by the elevated outer ridges, and the flat bottom only deforms by a small amount.

Figure 8A:
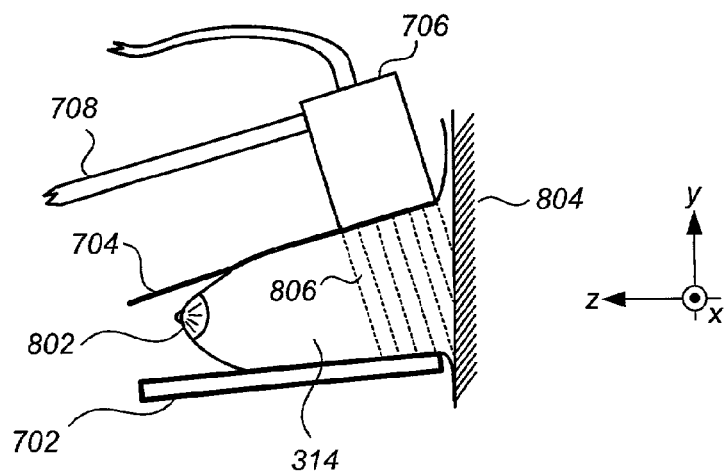
FIG. 8A illustrates a side view of a breast compressed within the ultrasound scanning apparatus of FIG. 7.

FIG. 8A illustrates a side cutaway view of a breast 314 as it is being compressed and scanned by the ultrasonic scanning apparatus 700. One advantage of the ultrasound scanning apparatus 700 is illustrated in FIG. 8A, which depicts a conceptual view of the substantially vertical chest wall 804 of the patient. Because the angle of the polyester film 704 is less than 90 degrees (preferably about 75 degrees) with respect to the chest wall 804, the acoustic interrogation field 806 can penetrate all the way to the chest wall 804 for most of the breast volume. This penetration can be achieved even where a high frequency ultrasound probe (e.g., 7.5 MHz or greater), which has a greater resolution but a lesser acoustic penetration depth, is used. This feature is especially important in light of the fact that a substantial percentage of breast cancers are formed within 2 cm of the chest wall. Yet another advantage of the ultrasound scanning apparatus 700 is its physical profile as a "stand-up" apparatus that takes up minimal floor space, which is a valuable and scarce resource at many medical clinics.

Figure 8B:
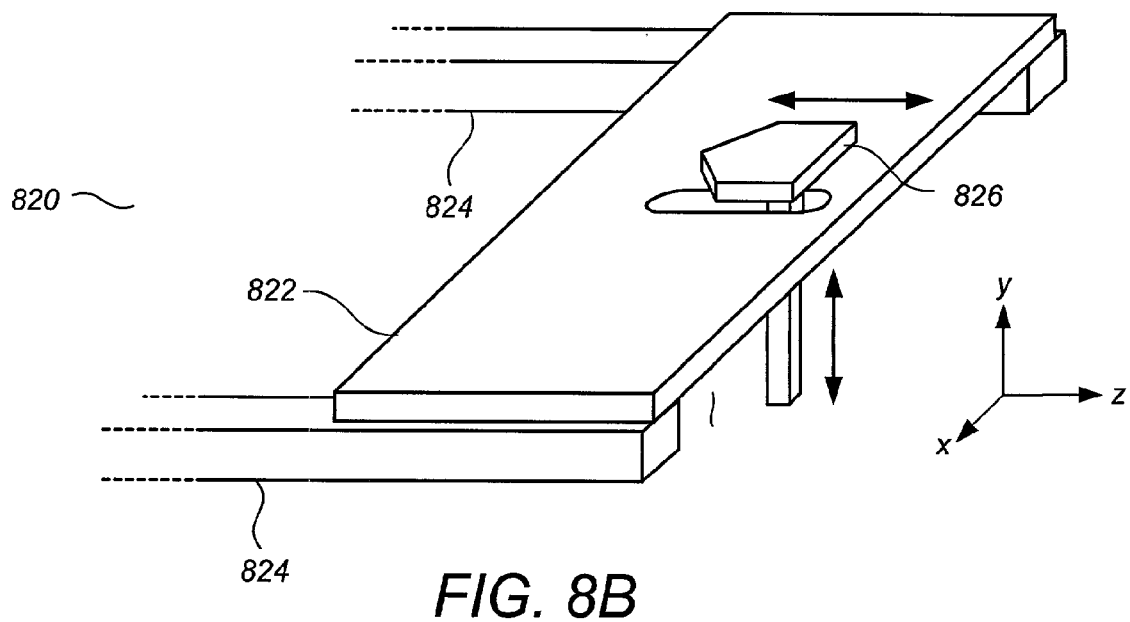
FIG. 8B illustrates a simplified perspective view of a portion of an ultrasound scanning apparatus according to a preferred embodiment.

FIG. 8B illustrates a lower portion 820 of an ultrasound scanning apparatus according to another preferred embodiment in which nipple imaging is enhanced. The ultrasound scanning apparatus is similar to that of FIG. 7, but only an area around the lower compressive member is drawn for clarity of description. A lower compressive member 822 is positioned on a lower support member 824 as in the embodiment of FIG. 7. Slidably coupled to the lower compressive member is a nipple support platform 826 for urging the breast nipple upward toward the polyester film. The nipple support platform 826 comprises a rigid frame that is covered by a soft, pliable silicone material such as a rubber sheet. The nipple support platform 826 is adjustable in two directions as indicated in FIG. 8B in order to be operative on a variety of different breast types. A locking mechanism (not shown) locks the nipple support platform 826 into place after being adjusted to a particular breast. The nipple support platform 826 allows the area of the breast near the nipple, as well as the nipple itself, to appear more completely in the acquired adjunctive ultrasound data.

Figure 8C:
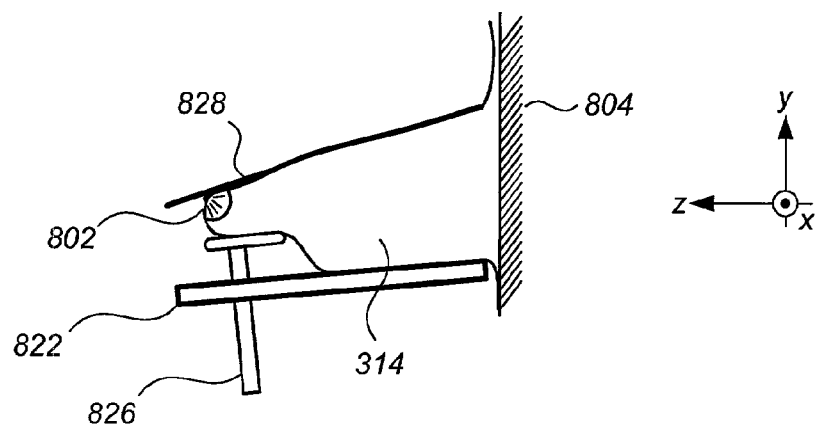
FIG. 8C illustrates a side view of a breast compressed within the ultrasound scanning apparatus of FIG. 8B.

FIG. 8C illustrates a side view of the breast 314 as it is being compressed and scanned by the ultrasonic scanning apparatus of FIG. 8B. The nipple support platform 826 gently urges the nipple 802 against the polyester film 828 such that it makes sound acoustic contact therewith. This enhances imaging of the nipple 802, which is a useful reference point for the radiologist in comparing the ultrasonic images to the x-ray mammogram images. By acoustic contact, it is meant that the nipple 802 either directly touches the polyester film 828 or is close enough to it such that any gaps between the nipple 802 and the polyester film 828 are occupied by ultrasonic gel or other acoustically conductive material.

Figure 8D:
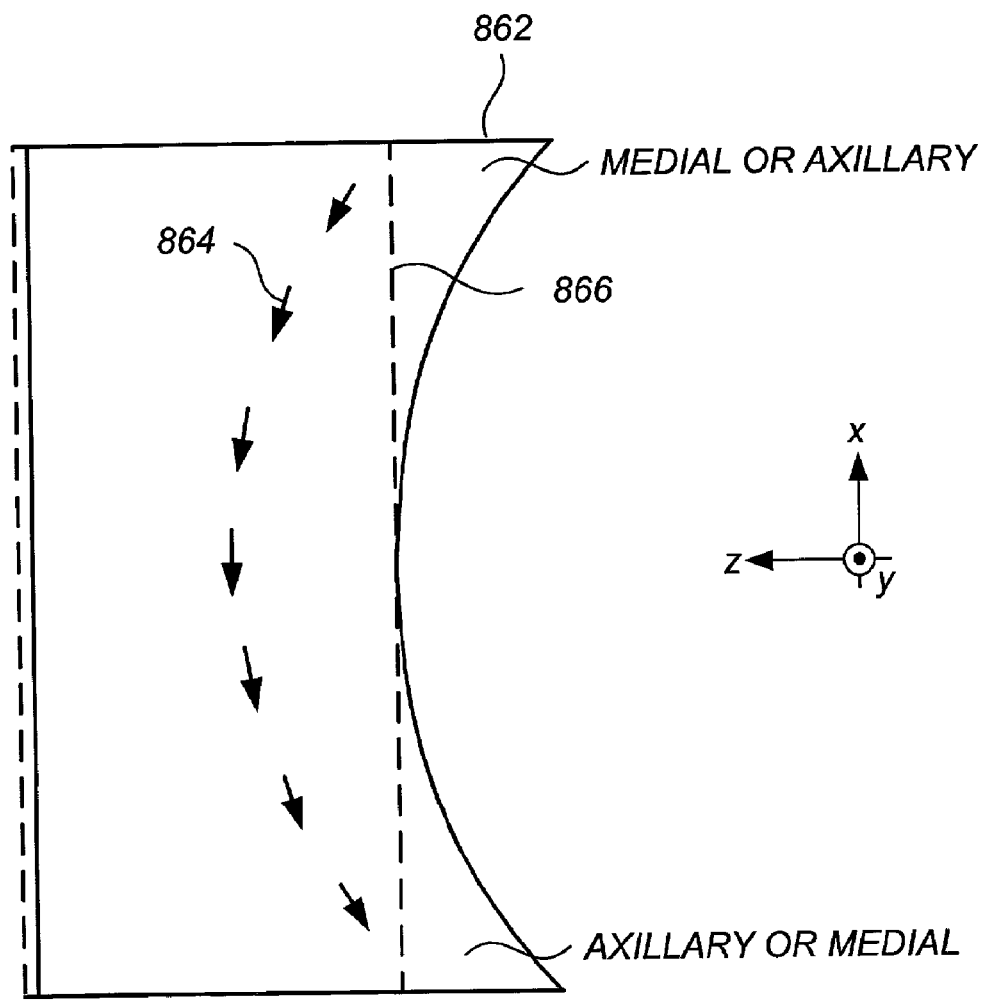
FIG. 8D illustrates a conceptual top view of an ultrasound scanning apparatus according to a preferred embodiment that facilitates an arcuate scanning trajectory.

FIG. 8D illustrates a simplified top view of a lower portion of an ultrasound scanning apparatus according to another preferred embodiment in which a more thorough scan of the breast is provided toward the medial and axillary regions of the breast near the chest wall. A lower compressive member 862 is curved so as to be conformal with the chest wall all the way from the center-facing side of the breast to the axillary side of the breast. It has been found that a radius of curvature of about 9 inches provides improved chest wall and axillary imaging of the breast for a broad range of breast sizes. Optionally, different lower compressive members with different shapes and/or radii of curvature are used for different patients, e.g., different lower compressive members for small, medium, and large breasts. During the scanning process, the ultrasound probe is moved in a curved or arcuate trajectory by an actuator mechanism, for example, by adapting the actuator 710 of FIG. 7 to have an inward/outward motion along with its side-to-side motion. The increased-area region 864 is shown in FIG. 8D for comparison with a rectangular-area scan area 866. Preferably, the associated x-ray mammograms are taken using a similarly-conformal x-ray detector mechanism, such as that described in U.S. Pat. No. 6,181,769, which is incorporated by reference herein. This allows meaningful comparison of the increased-area adjunctive ultrasound data with corresponding increased-area x-ray mammogram data.

Figure 9A:
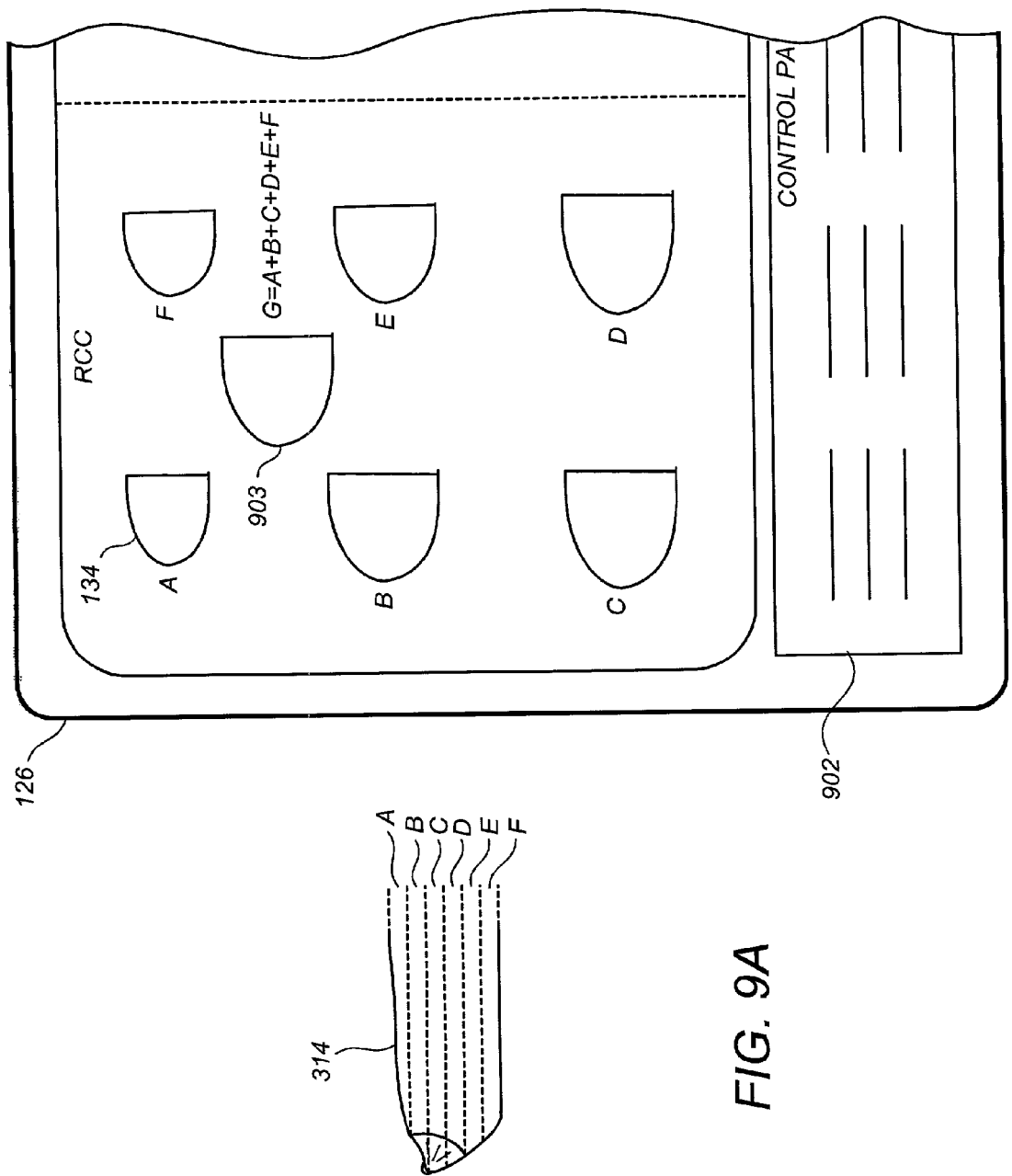
FIG. 9A illustrates a conceptual view of thick-slice portions of a breast as mapped upon the breast itself and as appears on an adjunct ultrasound display according to a preferred embodiment.

FIG. 9A illustrates a view of thick-slice portions A-F of a breast 314 as presented to the radiologist by the adjunct display 126 according to a preferred embodiment. It is to be appreciated that while the examples herein are presented in terms the right CC view ("RCC"), they are readily extended to other views and combinations of views. Adjunct display 126 comprises a control panel 902 (described further infra) for use by the radiologist in causing the thumbnail thick-slice images 134 to be displayed as shown. According to one preferred embodiment, the thumbnail thick-slice images 134 represent 10:1 subsamplings of the full-scale thick-slice images. However, it is to be appreciated that the thumbnail thick-slice images 134 can vary in size from very small to very large, even full-scale or bigger, depending on the number of thick-slice regions in the breast and the available space on the adjunct display 126. Thus, the term thumbnail image is used primarily to denote their information summarizing and linkage functionalities, and is not to be construed as limiting their size. As indicated in FIG. 9A, the thick-slice thumbnail images 134 are preferably displayed in a quasi-counterclockwise manner ("A" downward to "C" on the left side, "D" upward to "F" on the right side) to approximate a visual "migration" for the radiologist's eye from the top layer to the bottom layer of the breast 314. In an alternative preferred embodiment, the sequence can be quasi-clockwise.

According to another preferred embodiment, as illustrated in FIG. 9A, an image 903 showing a composite view G is also displayed to the user. The composite view G represents an integration of all of the thick-slice images (A+B+C+D+E+F) and/or their component slices such that it represents information from the entire breast volume. Preferably, the composite view G of the breast has its gray-scale polarity toggled and/or remapped such that it is reminiscent of an x-ray mammogram taken from the standardized x-ray mammogram direction. In another preferred embodiment, each of the thick-slice thumbnail images 134 has its gray-scale polarity toggled and/or remapped such that it is reminiscent of an x-ray mammogram.

Figure 9B:
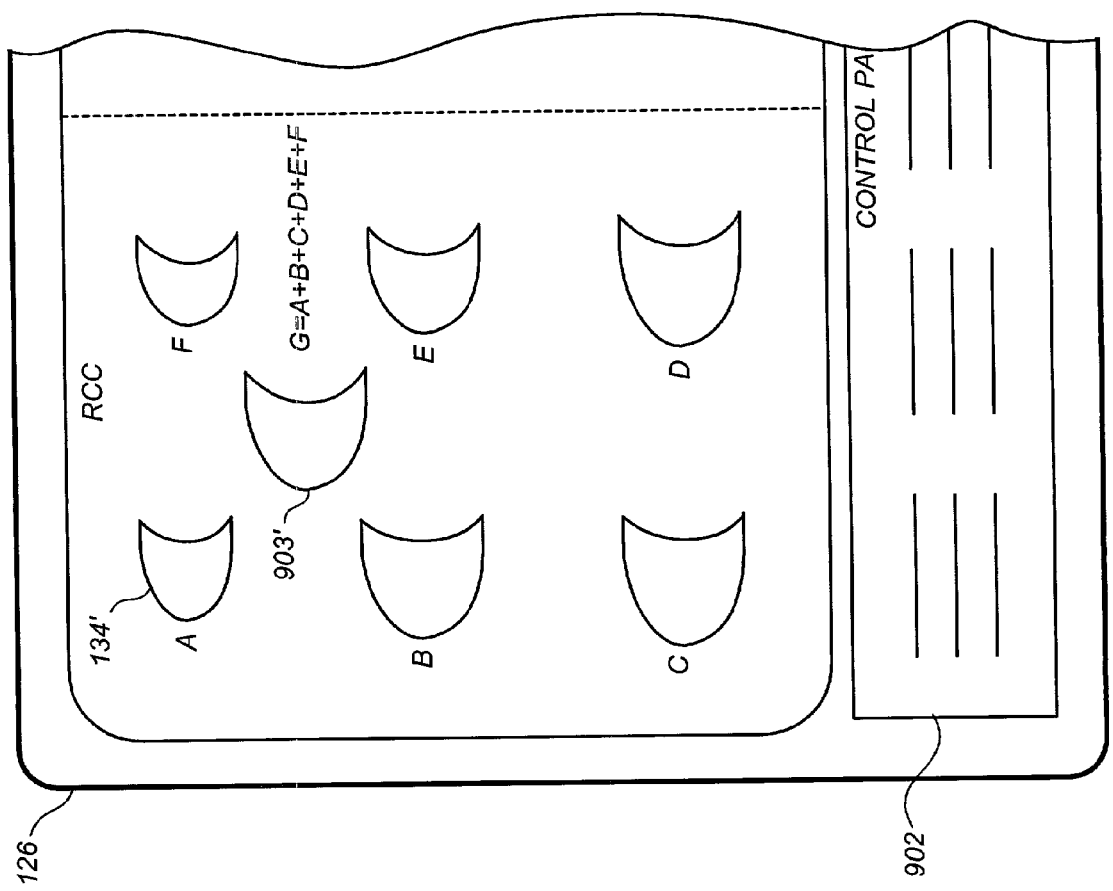
FIG. 9B illustrates an adjunct ultrasound display according to a preferred embodiment corresponding to an arcuate ultrasound scanning trajectory.

FIG. 9B illustrates an adjunct ultrasound display according to a preferred embodiment that is similar to FIG. 9A, except that the arcuate-trajectory scanning apparatus of FIG. 8D was used. As indicated in FIG. 9B, increased information near the medial and axillary regions of the breast is provided in the images 134' and 903'.

Figure 10A:
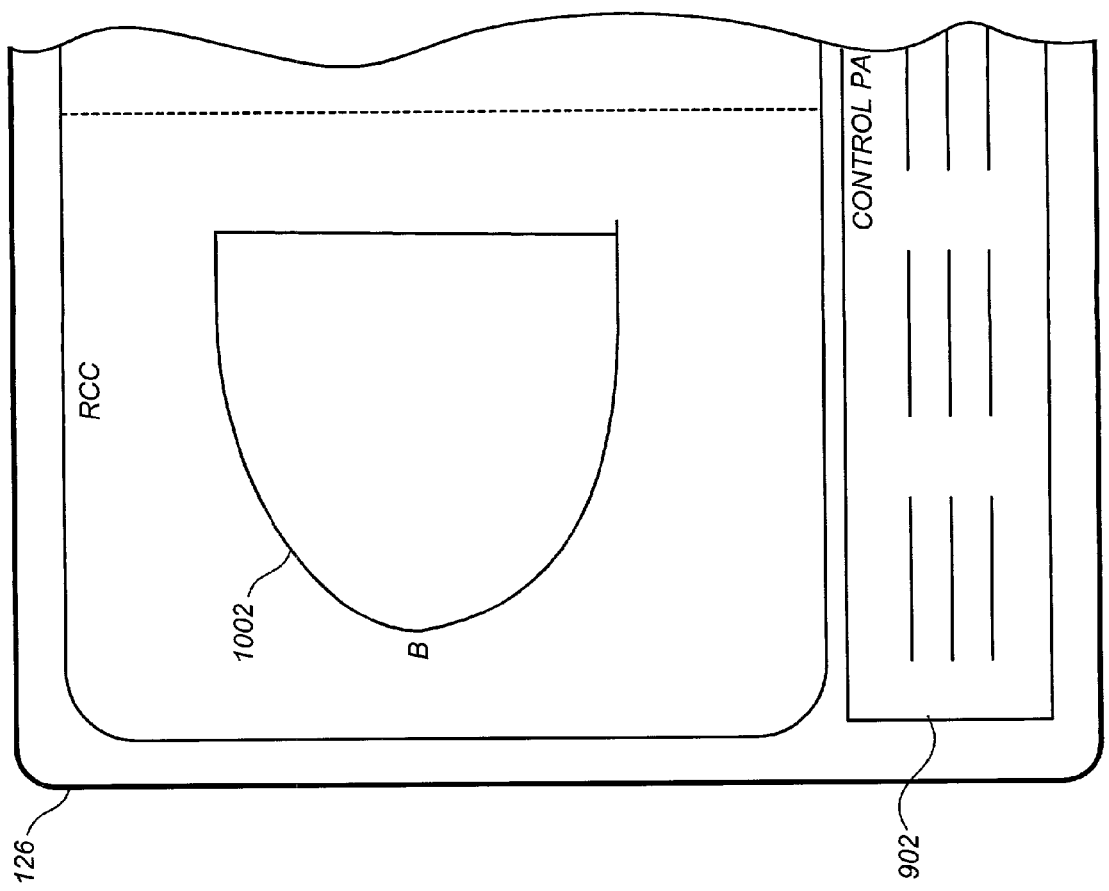
FIG. 10A illustrates an adjunct ultrasound display according to a preferred embodiment.

FIG. 10A illustrates a view of a single thick-slice volume "B" of the breast 314 in the form of a thick-slice image 1002. Preferably, the thick-slice image 1002 is identical or at least close in size to the x-ray mammogram of the breast to facilitate comparisons therebetween. In operation, the full-scale thick-slice image 1002 is caused to appear in place of the side-by-side thumbnail display of FIG. 9A by pressing an "enlarge" button on the control panel 902 and pressing the thumbnail image "B" on the touchscreen display.

Figure 10B:
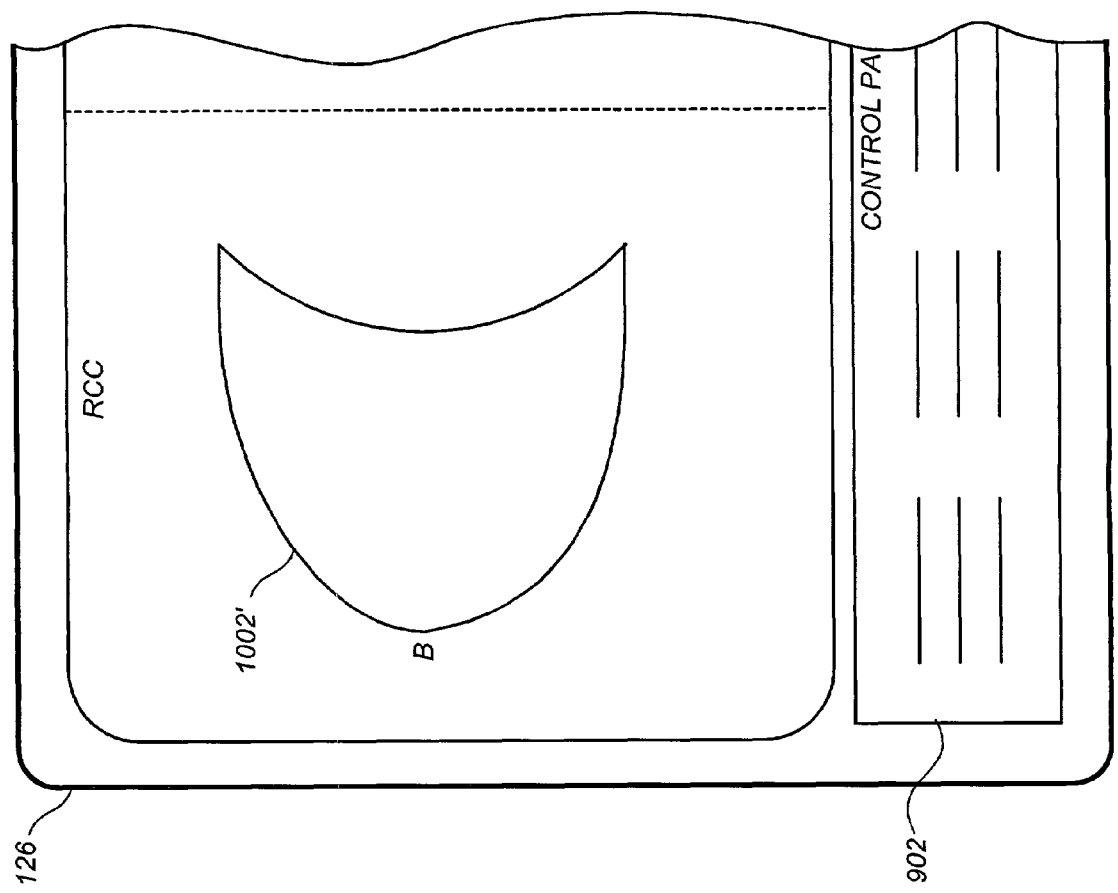
FIG. 10B illustrates an adjunct ultrasound display according to a preferred embodiment corresponding to an arcuate ultrasound scanning trajectory.

FIG. 10B illustrates an adjunct ultrasound display according to a preferred embodiment that is similar to FIG. 10A, except that the arcuate-trajectory scanning apparatus of FIG. 8D was used. As indicated in FIG. 10B, increased information near the medial and axillary regions of the breast is provided.

Figure 11:
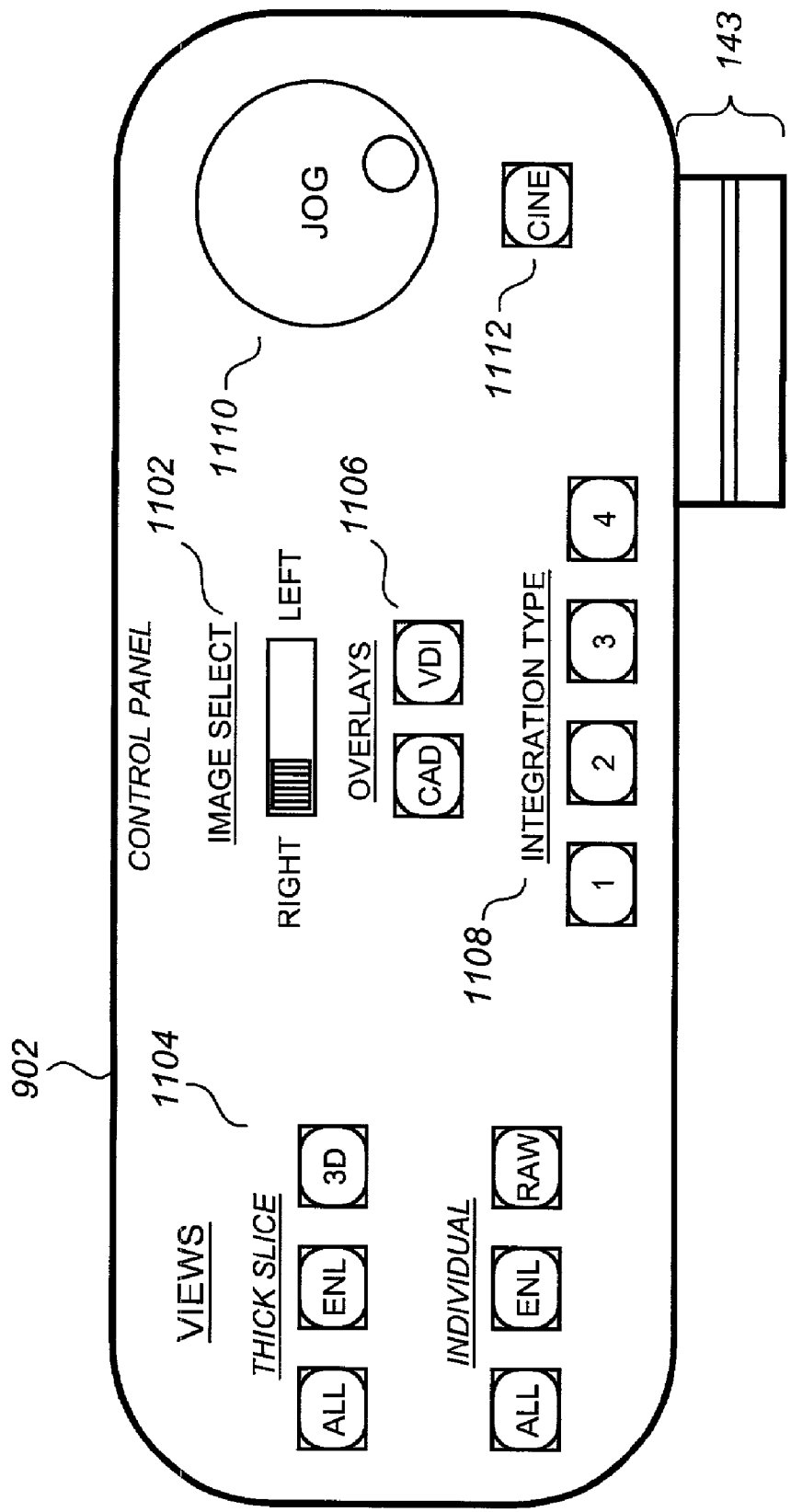
FIG. 11 illustrates a control panel of an adjunct ultrasound display according to a preferred embodiment.

FIG. 11 illustrates a close-up view of the control panel 902 of an adjunct ultrasound display according to a preferred embodiment. A two-position image select switch 1102 allows the radiologist to separately control the displays of the right and left breasts, which appear side-by-side on the adjunct display 126 as shown in FIG. 1 supra. A view control area 1104 allows the radiologist to select among a variety of views. If a particular view also requires an identification of a thumbnail image, the radiologist touches that thumbnail image on the touchscreen. By pressing the THICK SLICE-ALL button, the radiologist causes the side-by-side thumbnails of thick-slice images to appear as in FIG. 9, which is also the default view. The THICK SLICE-ENL button (enlarge) causes a full-scale thick-slice image to be displayed as in FIG. 10A. The THICK SLICE-3D button causes a three-dimensional perspective image of a particular thick-slice portion of the breast to be displayed.

As described supra, the thick-slice images represent integrations of individual component ultrasound slices. It is often the case that the radiologist may be interested in viewing each individual component ultrasound slice separately. The INDIVIDUAL-ALL button causes all component ultrasound slices of a given thick-slice image to be displayed side-by-side. The INDIVIDUAL-ENL (enlarge) button causes a selected component ultrasound slice to be enlarged to a full-scale image that is the same size (or almost the same size) as the x-ray mammogram image. It is to be appreciated that the size of the full-scale image, which is projected to full scale using known dimensions from the ultrasound scanning process, might vary slightly from the actual mammogram size. This is because the mammogram will be slightly larger than the breast due to some spreading of the x-ray beam on its way to the x-ray film or detector. For use in conjunction with this feature, a JOG control 1110 allows the radiologist to jog through all of the component ultrasound slices of the thick-slice image, and a CINE control 1112 allows the radiologist to alternatively view a cine-loop presentation of the component ultrasound slices.

As described supra, depending on the orientation from which the original ultrasound scans were taken, the individual component ultrasound slices that form a given thick-slice image may either be "raw" ultrasound data (if the original scans are taken in the same plane as the x-ray mammogram view plane), or may themselves be computational constructs from a three-dimensional volumetric representation of the breast (if the original scans are taken in a different plane than the x-ray mammogram view plane). In either case, the radiologist may wish to view the raw ultrasound slices obtained from the original ultrasound scan of the patient, which is done by pressing the INDIVIDUAL-RAW button. The JOG control 1110 is used to "travel" among the raw ultrasound slices, or alternatively the CINE feature may be used.

Control panel 902 further comprises overlay controls 1106 that permit the radiologist to overlay CAD results and/or VDI data onto the thick-slice image(s) or individual-slice image(s) being displayed, responsive to toggle buttons CAD and VDI, respectively. Control panel 902 further comprises an integration control 1108 that allows the radiologist to select from among several different integration methods for generating the thick-slice images from their component ultrasound slices. For example, button "1" may select a straight arithmetic averaging method, button "2" may select a geometric averaging method, button "3" may select a weighted arithmetic averaging method using a first set of weights, button "4" may select a weighted arithmetic averaging method using a second set of weights, and so on. Techniques for generating thick-slice images from component ultrasound slices according to the preferred embodiments include arithmetic averaging, geometric averaging, reciprocal averaging, exponential averaging, and other averaging methods, in each case including both weighted and unweighted averaging techniques. One particularly suitable technique is a weighted arithmetic averaging method. The bar code reader 143 from FIG. 1, supra, is also shown in FIG. 11.

Figure 12:
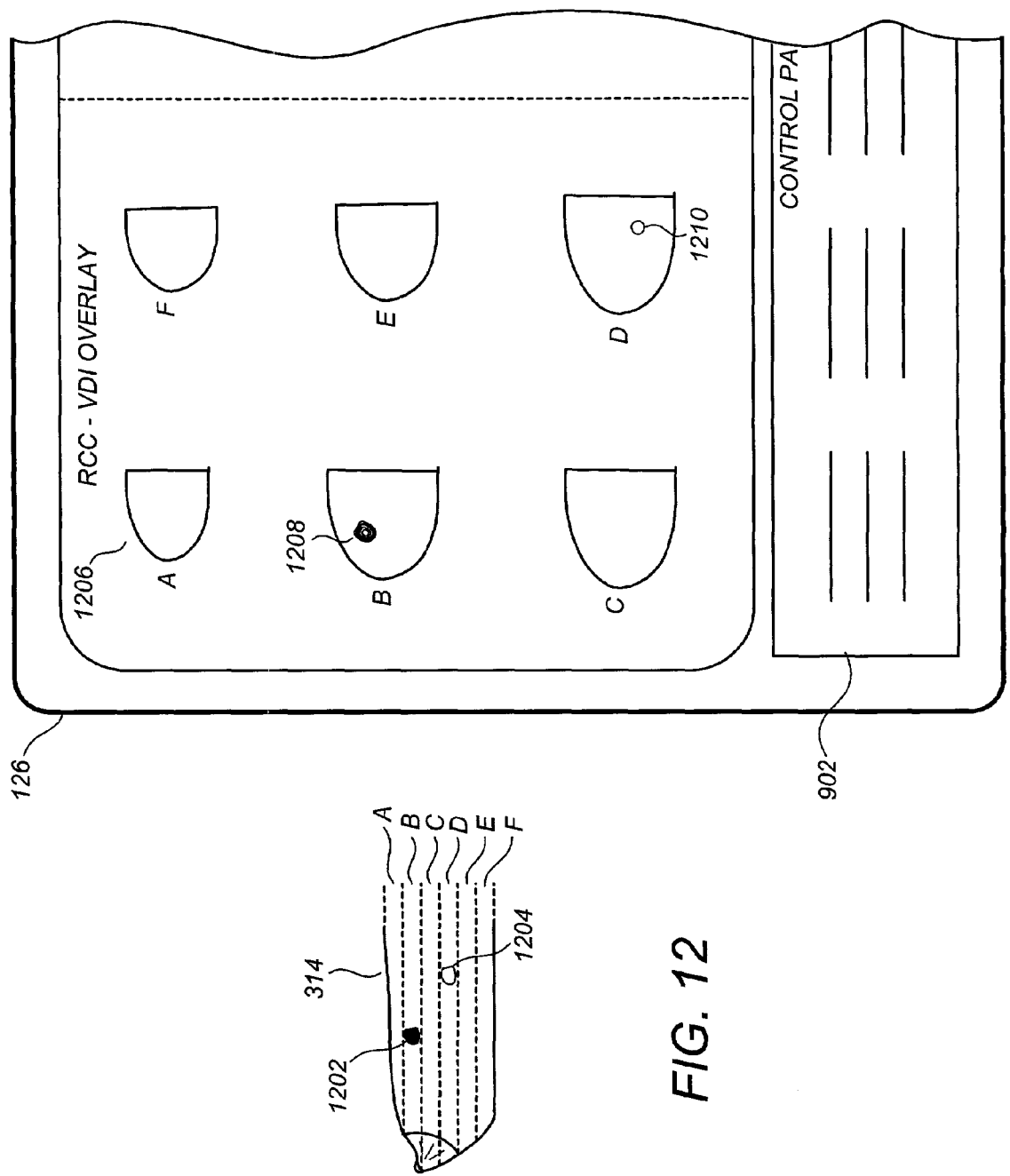
FIG. 12 illustrates an adjunct ultrasound display according to a preferred embodiment, along with an explanatory conceptual view of a breast with a cancerous tumor and a cyst.

FIG. 12 illustrates a conceptual view of an adjunct ultrasound display with a VDI overlay, along with a side view of a breast 314 corresponding thereto. In this example, the breast 314 contains a hard tumor 1202 in thick-slice region B and a liquid-filled cyst 1204 in thick-slice region D for purposes of illustrating an advantageous use of a VDI overlay according to a preferred embodiment. The hard tumor 1202 will usually resonate less than the surrounding tissue when the VDI audio frequency is injected, and will show up as reduced average Doppler velocity magnitude regions in the VDI overlay for the "B" slice, which is highlighted at location 1208 in FIG. 12. In contrast, the liquid-filled cyst 1204 will resonate roughly the same amount as the surrounding tissue and will tend to blend in the VDI overlay, as indicated by the weak dotted lines at location 1210 in FIG. 12. The ability to overlay VDI data onto the thick-slice images represents an important advantage afforded by an adjunctive ultrasound system in accordance with the preferred embodiments. Although shown in black-and-white in FIG. 12, the VDI overlays at locations 1208 and 1210 are preferably displayed according to a color map that maps different amounts of induced vibration into different colors, e.g., low amounts displayed in red, high amounts displayed in violet, etc. Preferably, the color map is generated individually for each set of VDI data and is normalized between the minimum and maximum VDI values for that data set.

Figure 13:
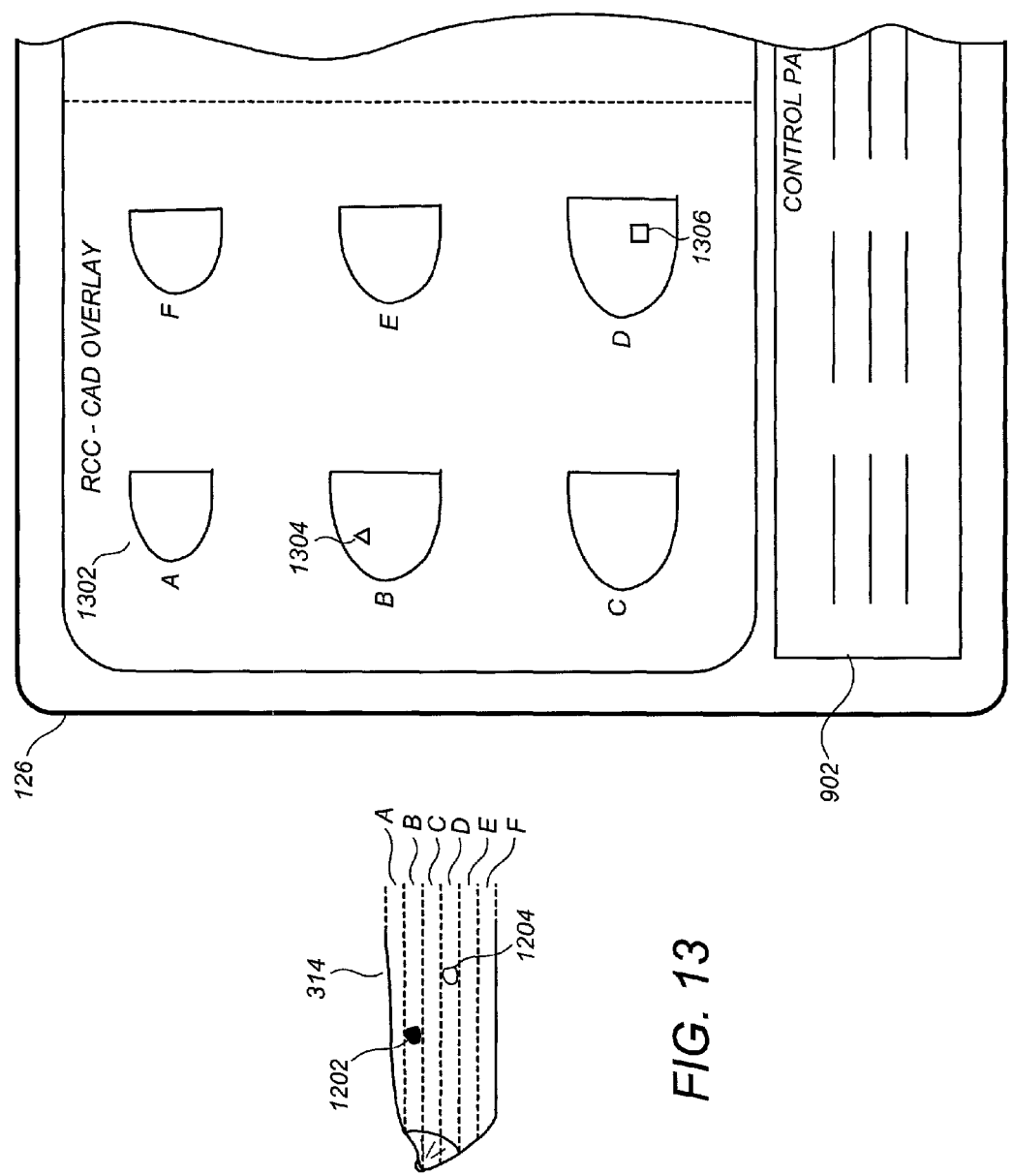
FIG. 13 illustrates an adjunct ultrasound display according to a preferred embodiment.

FIG. 13 illustrates a conceptual view of an adjunct ultrasound display with a CAD overlay corresponding to the breast presented in FIG. 12. By way of example, the problematic tumor 1202 has been singled out by a triangle 1304 to indicate a high degree of suspiciousness, while the cyst 1204 has been identified by a square 1306 to indicate a minimal degree of suspiciousness. Differently-sized icons may also be use to indicate different relative degrees of suspiciousness. Any of a variety of other CAD annotation schemes can be used, such as those described in U.S. Pat. No. 6,266,435 (Wang), which is incorporated by reference herein.

Figures 1, 14:
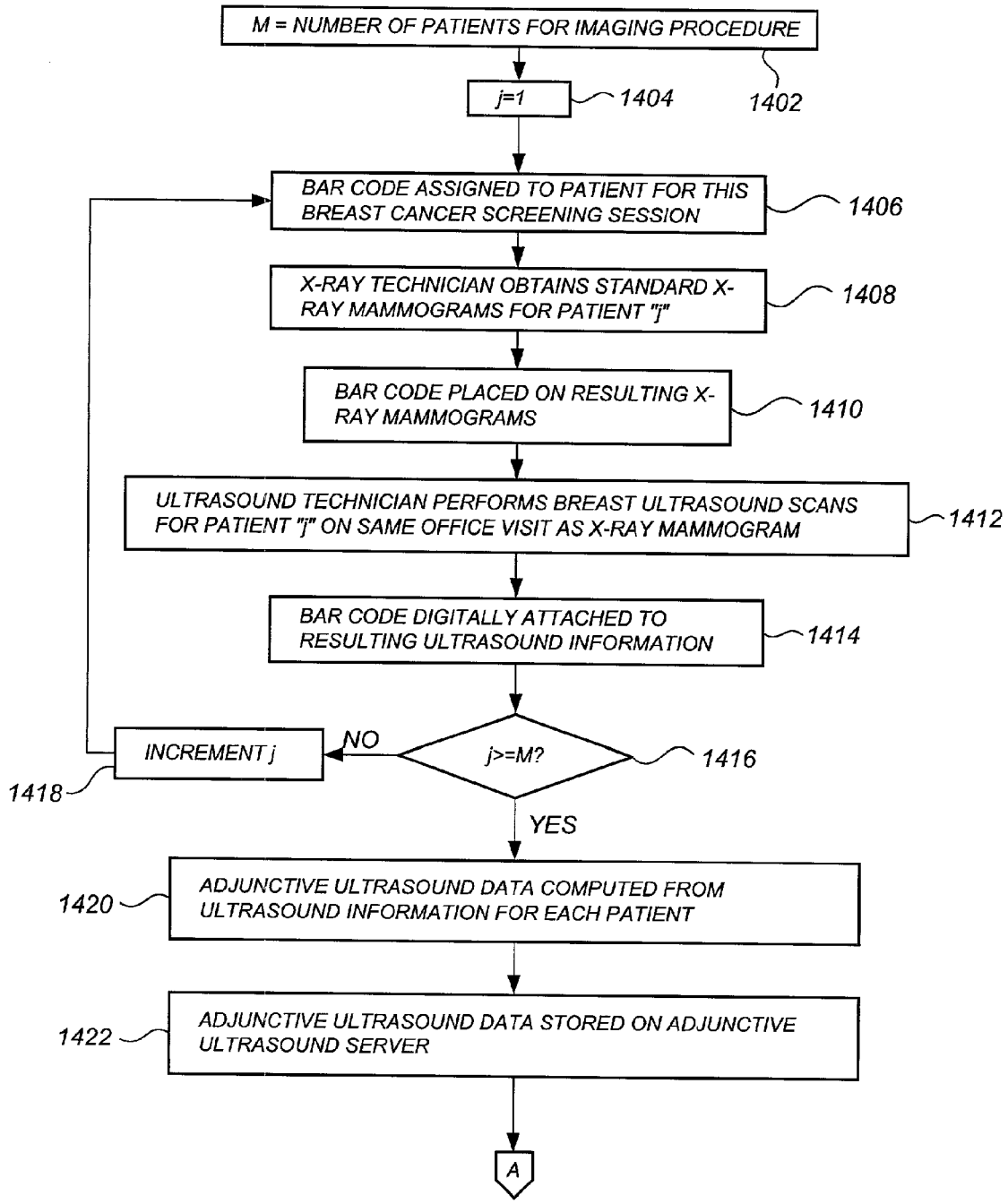
FIG. 14 illustrates steps for mass breast cancer screening using adjunctive ultrasound mammography according to a preferred embodiment.
Figures 2, 14:
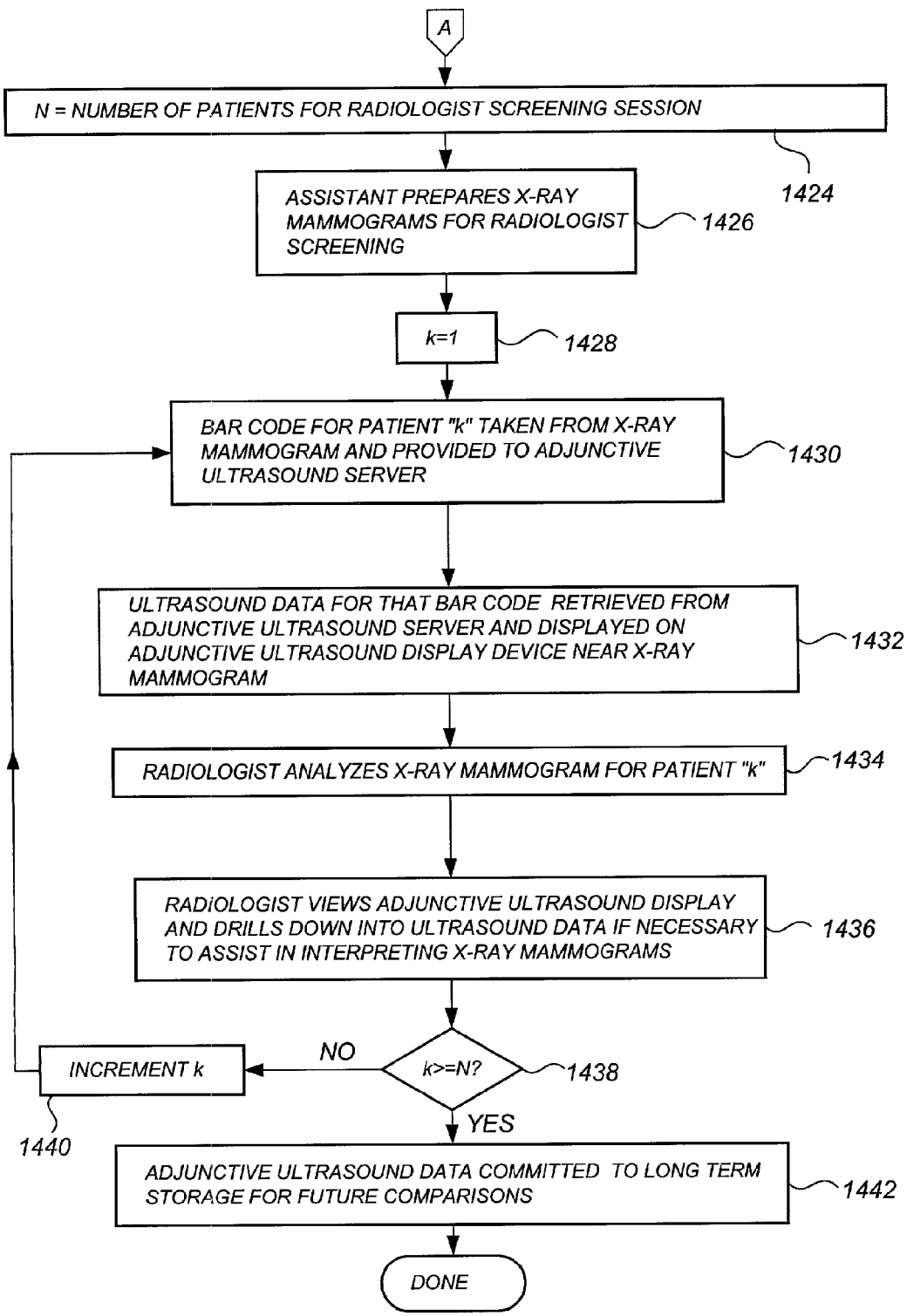

FIG. 14 illustrates steps for mass breast cancer screening using adjunctive ultrasound mammography according to a preferred embodiment. For the purposes of the flowchart of FIG. 14, "M" represents the number of patients to undergo ultrasound scanning (step 1402) with a counter variable "j" (step 1404), while "N" represents the number of x-ray mammograms to be screened in a single session by radiologist (step 1424) with a counter variable "k", it being understood that these two sets of events usually take place at substantially different intervals in time, e.g., 1-30 days apart. At step 1406, a bar code is assigned to the patient for the screening session. This is often done in large clinics by handing the patient a set of bar-coded stickers that are used to identify the patient in a plurality of tests on that visit such as blood tests, urine tests, etc. in addition to x-ray mammogram.

At step 1408, an x-ray technician obtains standard x-ray mammograms for the patient, and at step 1410 the x-ray technician places a bar code sticker on each x-ray mammogram film. As known in the art, if there is a palpable lesion in the breast, a small metallic marker or "BB" is taped to the breast at the tumor location to draw attention to this region. During the same visit, an ultrasound technician performs breast ultrasound scans on the patient, using a bar code scanner to scan in a bar code from one of the patient's stickers. This bar code is digitally attached to the resulting ultrasound information at step 1414, e.g. by insertion into a metadata field of each ultrasound information file. The same metallic marker or "BB" used for the x-ray mammogram may be used during the ultrasound scans to draw attention to palpable lesions. If not done earlier, after completing the scanning process for all "M" patients (steps 1416-1418), at step 1420 adjunctive ultrasound data (i.e. the set of data to be available for presentation to the radiologist) is computed from the raw ultrasound data for each patient. At step 1422, the adjunctive ultrasound data is stored onto an adjunctive ultrasound server, i.e., the server(s) with which the radiologist will interact during the en masse screening process.

At step 1426, an assistant prepares "N" x-ray mammograms for en masse radiologist screening. This step varies in complexity from simply mounting the mammograms onto one or more light boxes to loading and sequencing an x-ray mammography CAD station. When the radiologist turns their attention to the x-ray mammogram of a given patient "k," at step 1430 they scan the bar code contained on the x-ray mammogram using a bar code reader (not shown in FIG. 1). Alternatively, if a more sophisticated x-ray mammography screening apparatus is used such as a CAD workstation with an automated conveyor system, the assistant preparing the x-ray mammograms scans the bar code from each x-ray mammogram as it is being loaded into the conveyor system. This causes the desired adjunctive ultrasound data to displayed in synchronization with the x-ray mammograms. At step 1432, ultrasound data for that bar code is retrieved from the adjunctive ultrasound server and displayed on the adjunct display positioned near the x-ray mammogram. At step 1434, the radiologist screens the x-ray mammogram, and at step 1436 the radiologist views the adjunct display and drills down into the adjunctive ultrasound data as necessary to assist in interpreting the x-ray mammograms. After the screening process for all "N" x-ray mammograms (steps 1438-1440) is completed, the adjunctive ultrasound data is committed to long-term storage for future comparisons (step 1442). In one preferred embodiment, the radiologist may view one or more years of historical adjunctive ultrasound data for a given patient to see if any changes have taken place.

Figures 1, 15:
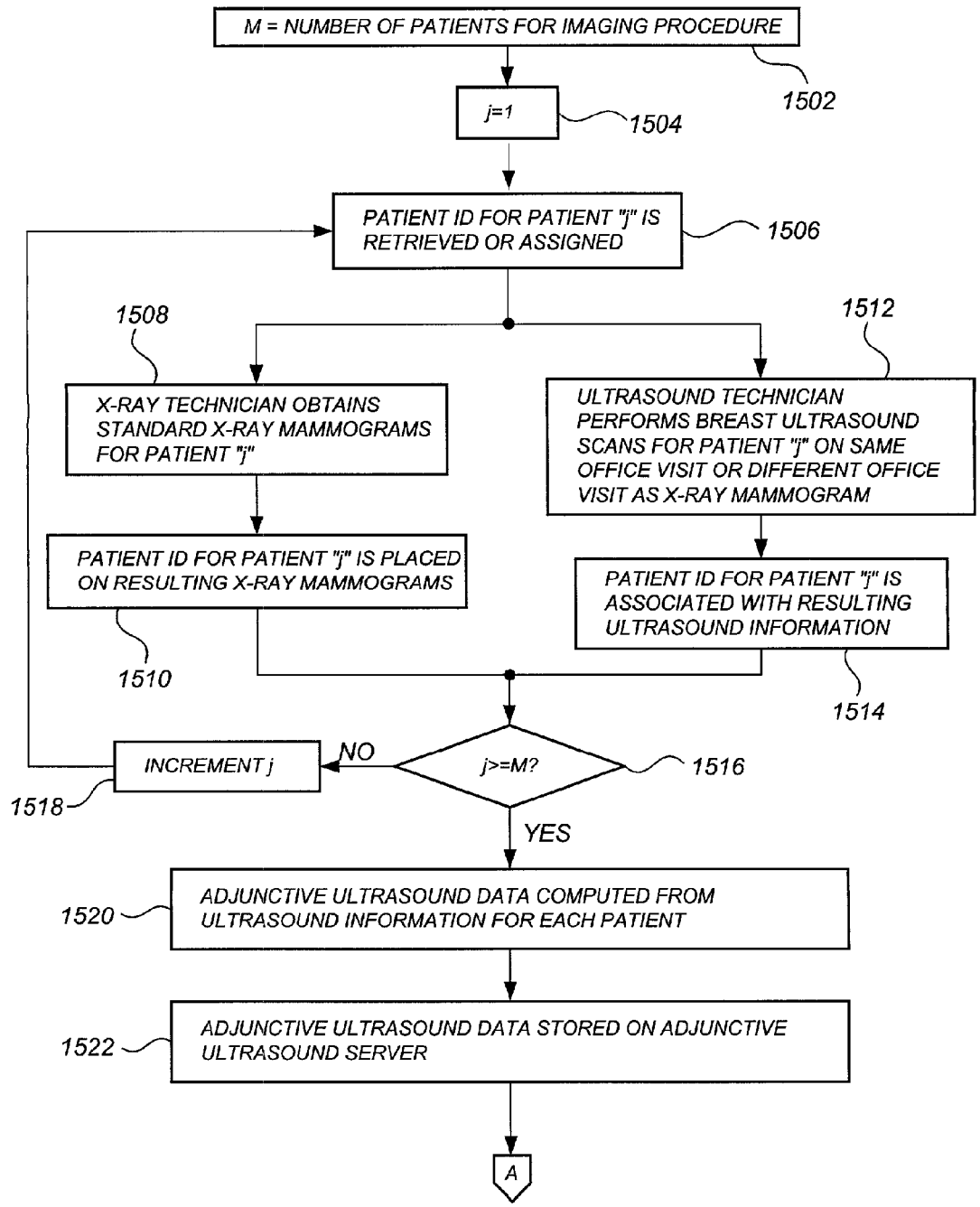
FIG. 15 illustrates steps for mass breast cancer screening using adjunctive ultrasound mammography according to a preferred embodiment.
Figures 2, 15:
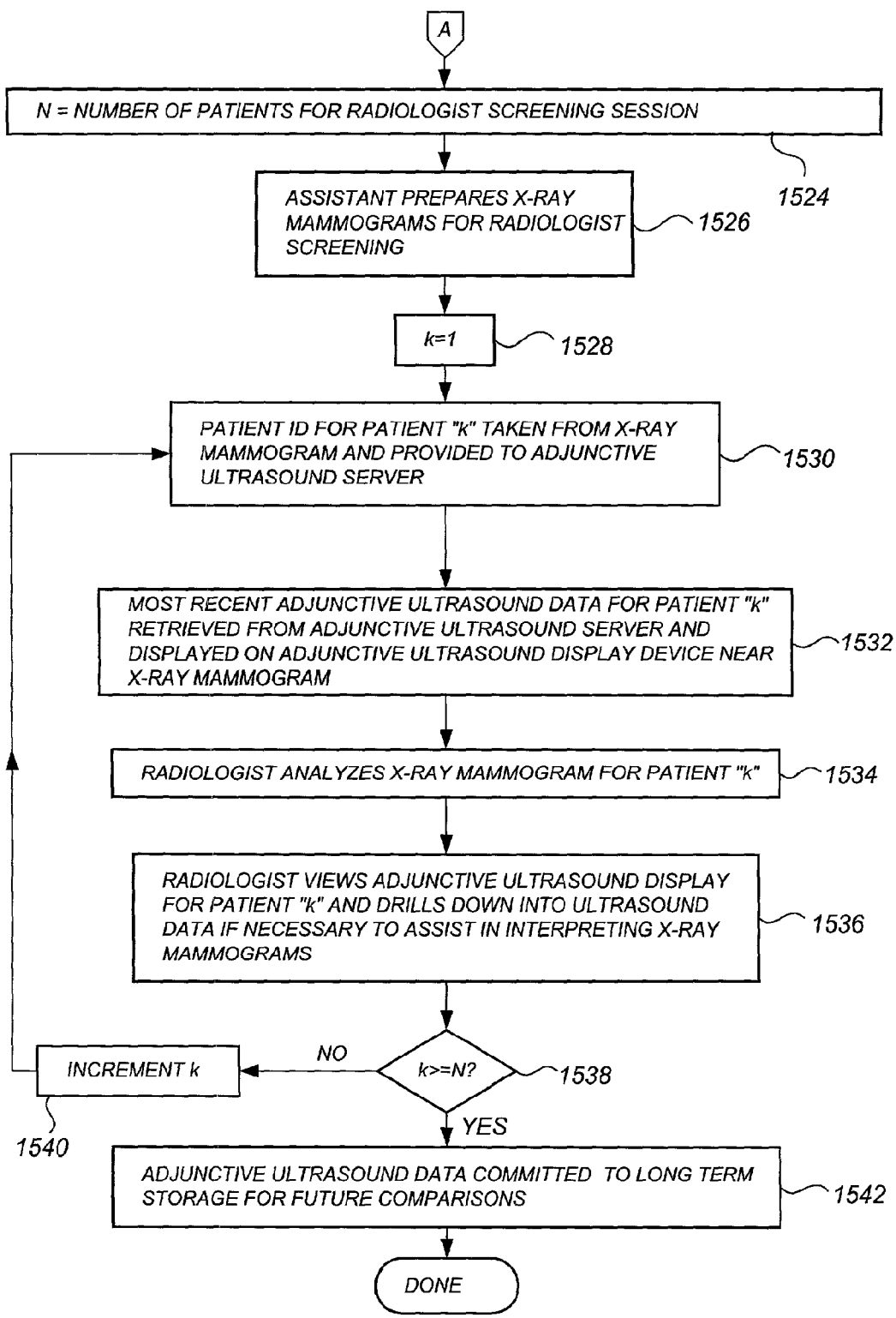

FIG. 15 illustrates steps for mass breast cancer screening using adjunctive ultrasound mammography according to a preferred embodiment. In the preferred embodiment of FIG. 15, it is not assumed that the patient undergoes x-ray mammography and ultrasonic mammography on the same visit, although same-day scenarios are accommodated. Steps 1502-1504, 1520-1526, and 1534-1542 proceed in a manner similar to steps 1402-1404, 1420-1426, and 1434-1442 of FIG. 14. However, at step 1506, a permanent patient ID (e.g., Social Security number, medical insurance number, hospital-assigned medical record number, etc.) is retrieved or assigned when the patient arrives at the clinic. At step 1508, an x-ray technician obtains standard x-ray mammograms for the patient, with the patient ID been placed directly on the x-ray mammogram film at step 1510. At step 1512, during that visit or another visit, an ultrasound technician performs breast ultrasound scans for the patient, and at step 1514 associates the patient ID with the resulting ultrasound information. At this time, a time stamp is automatically associated with that ultrasound information and patient ID. Later, during en masse x-ray mammogram screening, only the patient ID needs to be provided to the adjunctive ultrasound server (step 1530), and the most recent set of adjunctive ultrasound data is retrieved by the adjunctive ultrasound server for that patient ID (step 1532).

Figure 16:
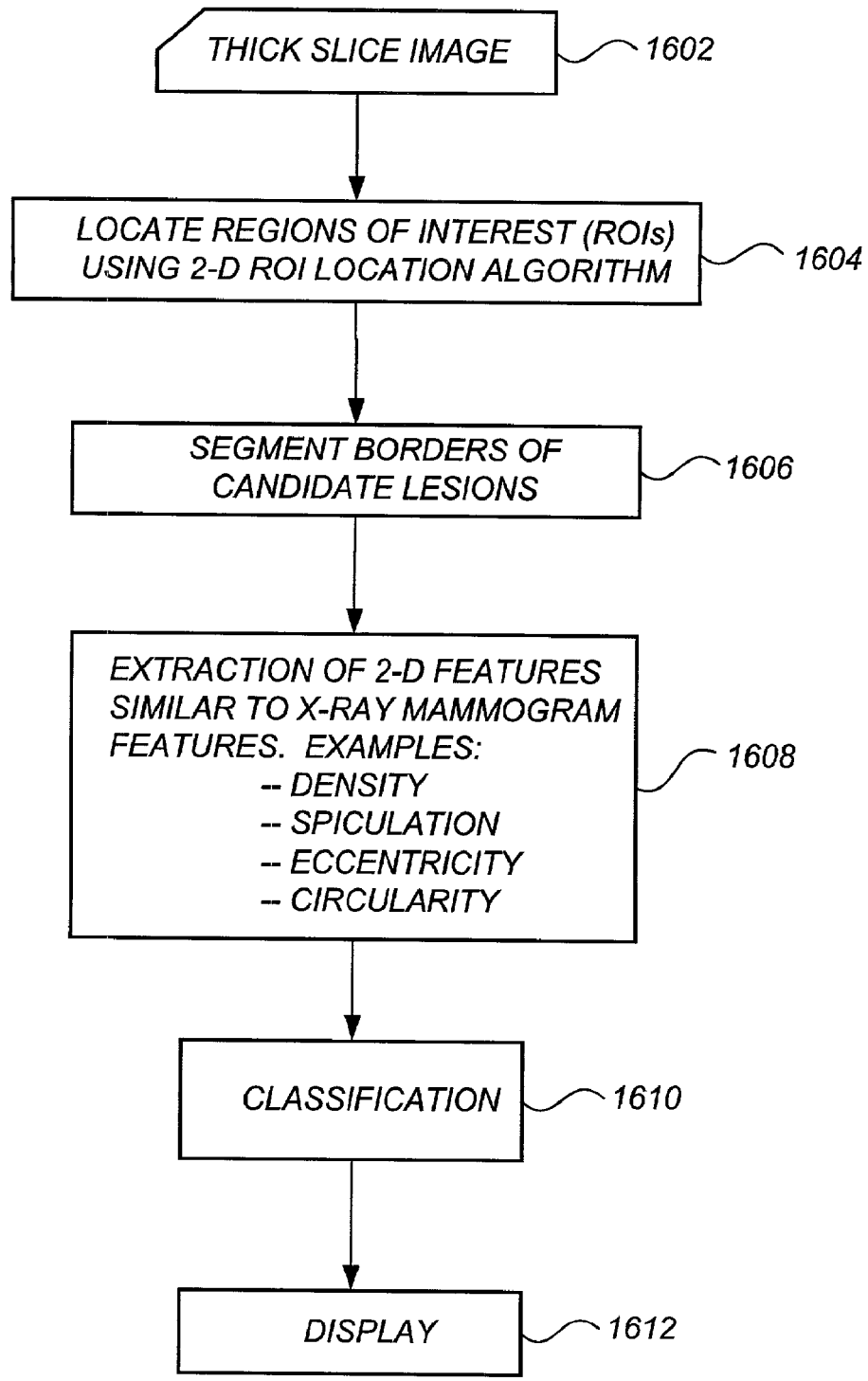
FIG. 16 illustrates steps for computer-aided diagnosis of adjunctive ultrasound data according to a preferred embodiment.

FIG. 16 illustrates steps for computer-aided diagnosis (CAD) of adjunctive ultrasound data according to a preferred embodiment. It has been found that the thick-slice ultrasound images described herein often possess substantially improved signal-to-noise ratios as compared to their component individual ultrasound slices, and are therefore more conducive to the use of two-dimensional CAD algorithms that have historically been used primarily for digitized x-ray mammograms. According to a preferred embodiment, on a two-dimensional thick-slice image provided at step 1602, regions of interest (ROIs) are located at step 1604 using a two-dimensional ROI location algorithm. Any of a variety of known two-dimensional ROI location algorithms can be used such as those described in: Singh, S. and Al-Mansoori. R., "Identification of Regions of Interest in Digital Mammograms," J. Intelligent Systems 10:2 (2000); U.S. Pat. No. 5,133,020; U.S. Pat. No. 5,491,627; U.S. Pat. No. 5,673,332; U.S. Pat. No. 5,790,690; U.S. Pat. No. 5,815,591; U.S. Pat. No. 6,035,056; U.S. Pat. No. 6,075,879; U.S. Pat. No. 6,198,838; U.S. Pat. No. 6,263,092; U.S. Pat. No. 6,278,793; U.S. Pat. No. 6,282,305; and U.S. Pat. No. 6,301,378, each of which is incorporated by reference herein. At step 1606, borders of candidate lesions are segmented at each ROI. Any of a variety of known two-dimensional segmentation algorithms can be used such as those described in: U.S. Pat. No. 5,671,294; U.S. Pat. No. 6,091,841; and Giger et. al., "Computer-Aided Diagnosis in Mammography," *Handbook of Medical Imaging*, Volume 2: *Medical Image Processing and Analysis*, Sonka and Fitzpatrick, eds., SPIE Press (2000) at Chapter 15 (pp. 915-1004), each of which is incorporated by reference herein.

At step 1608, two-dimensional features commonly associated with x-ray mammogram CAD algorithms are extracted. Such features include, for example, spiculation metrics, density/contrast metrics, eccentricity metrics, circularity metrics, border roughness metrics, location metrics (e.g., distance to chest wall, proximity to axilla, proximity to subareolar areas, etc.), edge shadow metrics, border metrics, texture metrics, size metrics, shape metrics, internal echo metrics, and tenting metrics. However, the scope of the preferred embodiments extends to a variety of other known two-dimensional features as well, such as those described in U.S. Pat. No. 5,815,591; and Giger et. al., "Computer-Aided Diagnosis in Mammography," supra at pp. 933-958. At step 1610, one or more classifier algorithms operate on the set of two-dimensional features extracted in step 1608. Any of a variety of classification methods known in the art may be used in accordance with the preferred embodiments, including linear classifier algorithms, quadratic classifier algorithms, K-nearest-neighbor classifier algorithms, decision tree classifier algorithms, and neural network classifier algorithms, as well as those described in the references cited above. At step 1612, based on one or more scores computed during the classification step, CAD outputs are displayed to draw the attention of the radiologist to certain locations in the thick-slice image and/or to provide other useful information.

It has been found that problematic breast cancer tumors exhibit certain acoustic behaviors that can be used to differentiate them from non-problematic lesions in some cases, such acoustic behaviors only being detectable using sonomammography, such acoustic behaviors being particularly apparent in the thick-slice images described herein. According to a preferred embodiment, features associated with these acoustic behaviors are extracted from the thick-slice images and classified in combination with the conventional features described supra to further improve both specificity and sensitivity in breast cancer screening.

Figure 17A:
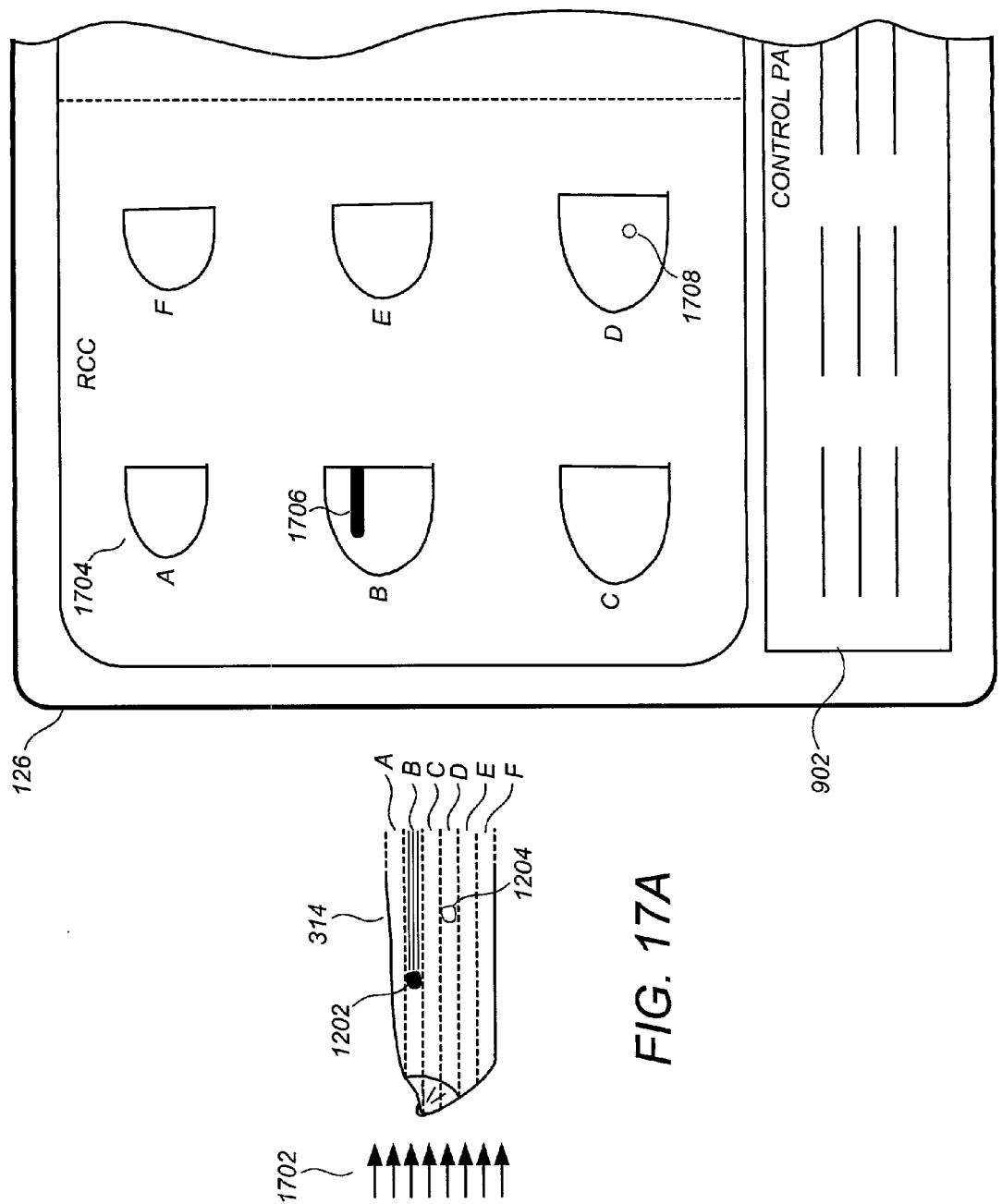
FIGS. 17A and 17B illustrate an adjunct ultrasound display according to a preferred embodiment in which a lesion casts lateral shadows across a thick-slice image, along with explanatory conceptual views of interrogating ultrasonic waves impinging upon the breast.

FIG. 17A illustrates a conceptual view of an adjunct ultrasound display comprising a plurality of thumbnail thick-slice images 1704, along with a side view of a corresponding breast 314. As in FIG. 12 supra, the breast 314 again contains a hard tumor 1202 in thick-slice region B and a liquid-filled cyst 1204 in thick-slice region D. In the example of FIG. 17A, it is presumed that the interrogating acoustic pulses 1702 are parallel to the CC plane and come from the front of the breast. The problematic hard tumor 1202 casts an acoustic shadow in the direction of the interrogating acoustic pulses 1702. However, because it is filled with a substantially acoustically transparent liquid, the liquid-filled cyst 1204 does not cast such a shadow. Indeed, the liquid-filled cyst often causes amplified readings at an edge where the acoustic interrogation signals exit the cyst, an effect known as posterior enhancement. Using the thick-slice image displays according to the preferred embodiments, the radiologist can readily see a shadow 1706 cast across thick-slice image B, while no such shadow is cast across thick-slice image D.

Figure 17B:
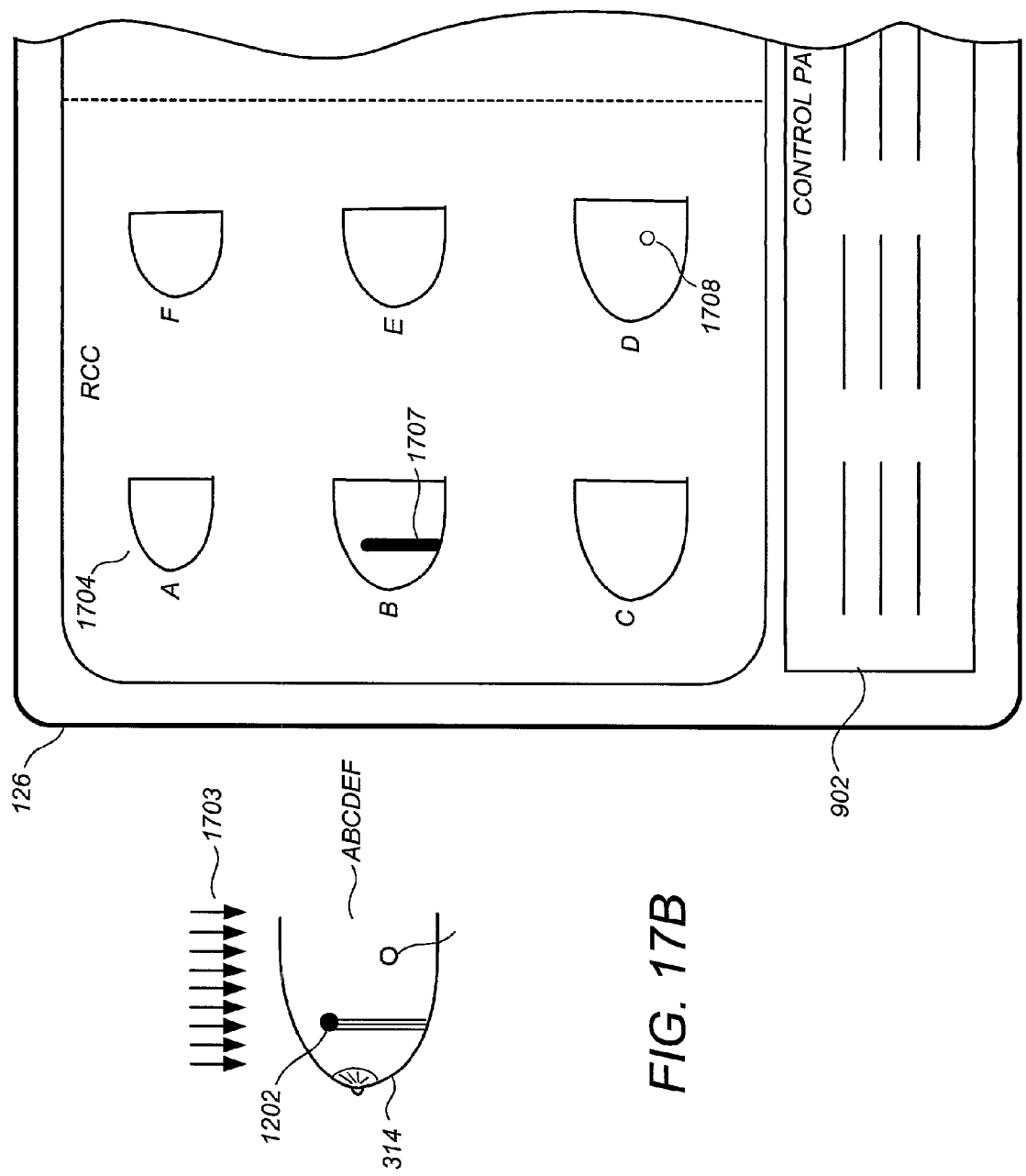

FIG. 17B illustrates a similar conceptual view of an adjunct ultrasound display comprising a plurality of thumbnail thick-slice images 1704, except that a top view of the corresponding breast 314 is shown. Interrogating pulses 1703 are introduced from the side of the compressed breast, which is often desirable to avoid nipple shadow effects. As indicated in FIG. 17B, a lateral shadow 1707 is cast across thick-slice image B perpendicular to the shadow of FIG. 17A. Again, however, no such shadow is cast across thick-slice image D and indeed there is a posterior enhancement effect. In view of the present disclosure, a person skilled in the art would readily be able to construct a CAD algorithm capable of extracting a lateral shadow feature exemplified in FIGS. 17A-17B, computing a lateral shadow metric corresponding thereto, and using such a metric in a classifier algorithm to assist in classifying the suspect lesion.

Figure 18:
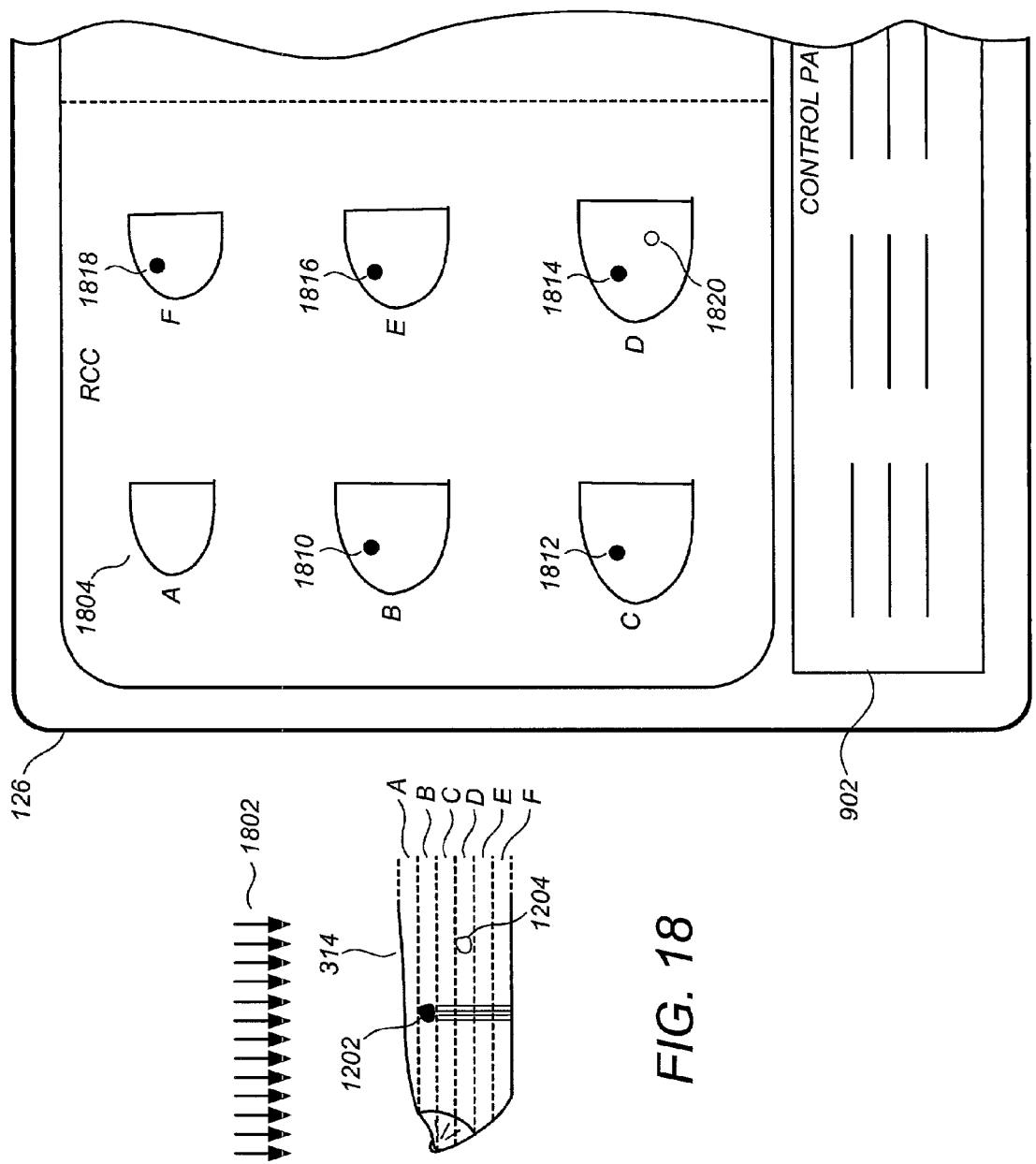
FIG. 18 illustrates an adjunct ultrasound display according to a preferred embodiment in which a lesion casts a vertical shadow across other thick-slice images, along with an explanatory conceptual view of a breast with a suspect lesion.

FIG. 18 illustrates a conceptual view of an adjunct ultrasound display and breast 314 similar to that of FIG. 17B; interrogating acoustic pulses 1802 are introduced in planes perpendicular to the CC plain during the initial ultrasound scanning process. In this case, an acoustic shadow is cast across all lower slices C-F by the hard tumor 1202, while the cyst 1204 again produces no acoustic shadow (and indeed there is a posterior enhancement effect). Again by viewing the array of thick-slice images, with particular attention to the locations 1810-1818 shown in FIG. 18, the radiologist can readily see that some object lying in the B thick-slice region at location 1810 is acoustically opaque enough to cast a shadow down through the other slices. Moreover, in view of the present disclosure, a person skilled in the art would readily be able to construct a CAD algorithm capable of extracting this vertical shadow feature and use it to assist in classifying the suspect lesion.

Figure 19:
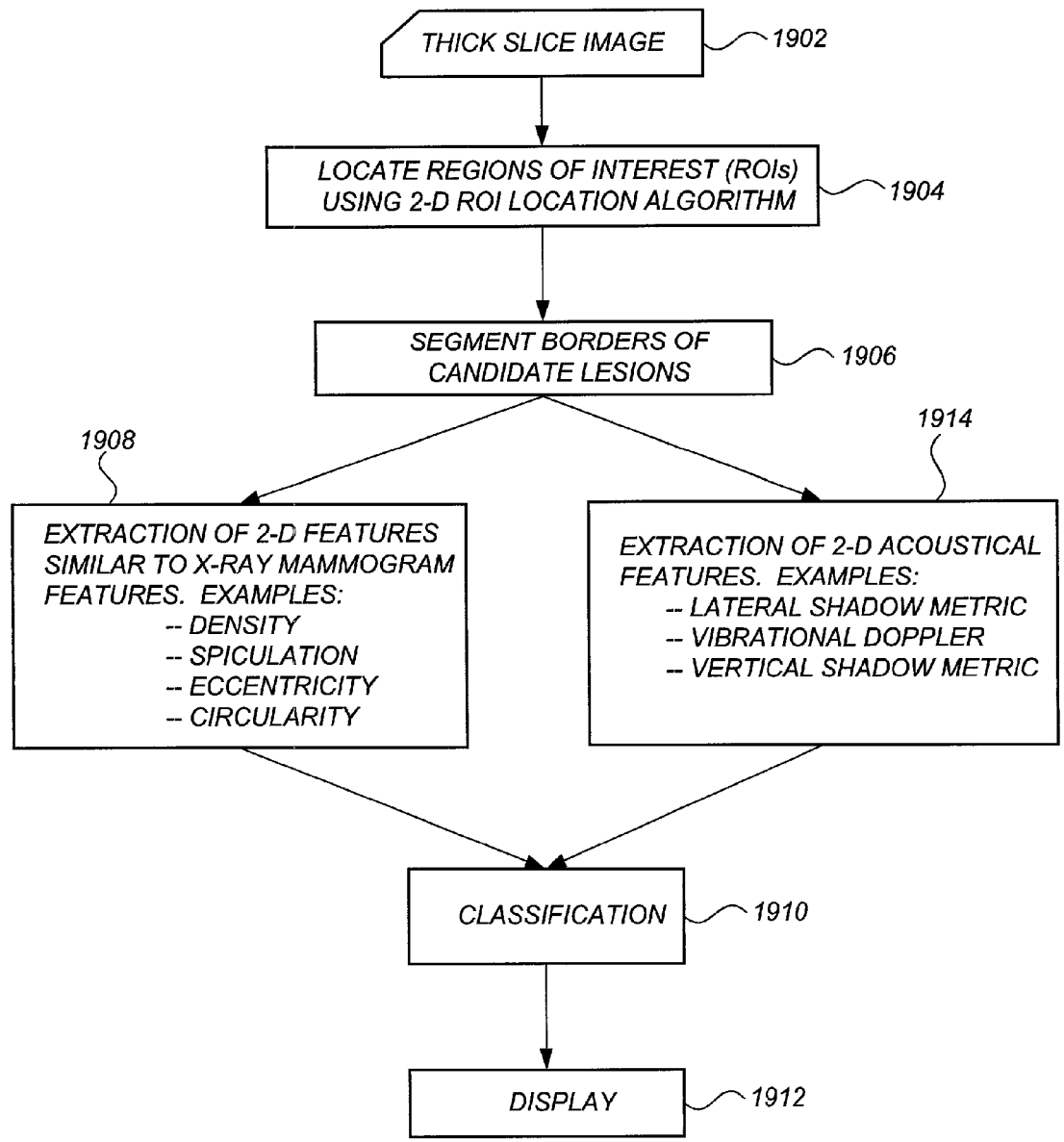
FIG. 19 illustrates steps for computer-aided diagnosis of adjunctive ultrasound data according to a preferred embodiment.

FIG. 19 illustrates steps for computer-aided diagnosis (CAD) of adjunctive ultrasound data according to a preferred embodiment. Thick-slice image acquisition (step 1902), ROI location (step 1904), and segmentation (step 1906), and extraction of conventional two-dimensional features (step 1908) proceed in a manner similar to steps 1602-1608 of FIG. 16, respectively. However, at step 1914, an additional step is carried out of extracting two-dimensional acoustical features including, for example, a lateral shadow metric, a vertical shadow metric, a VDI metric, and a posterior enhancement metric.

At step 1910, the results of both the steps 1908 and 1914 are processed by one or more classifier algorithms, and at step 1912, based on one or more scores computed during the classification step, CAD outputs are displayed. Notably, feature extraction results for a given thick-slice image may depend on the characteristics of other thick-slice images, as in the case of the vertical shadow metric described supra in FIG. 18.

Although two-dimensional CAD algorithms performed on the two-dimensional thick-slice images yield useful results, further useful results can be obtained by using the fact that thick-slice regions of the breast are indeed three dimensional in nature. Accordingly, useful three-dimensional thick-slice information can be obtained from a three-dimensional volumetric representation of the breast and used in conjunction with the two-dimensional information to even further increase specificity and sensitivity of the breast cancer screening process.

Figure 20A:
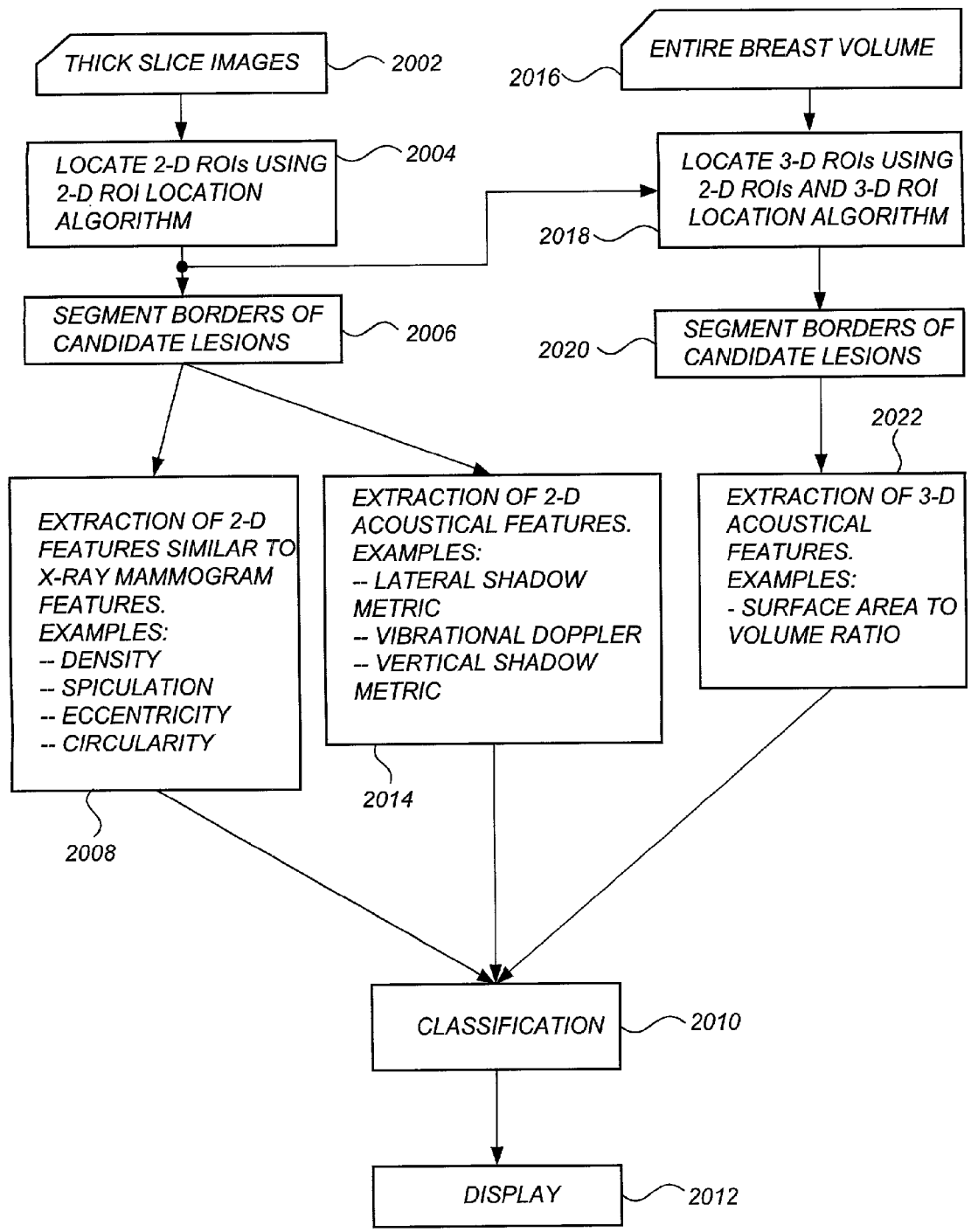
FIG. 20A illustrates steps for computer-aided diagnosis of adjunctive ultrasound data according to a preferred embodiment.

FIG. 20A illustrates steps for computer-aided diagnosis (CAD) of adjunctive ultrasound data according to a preferred embodiment. Thick-slice image acquisition (step 2002), ROI location (step 2004), segmentation (step 2006), extraction of conventional two-dimensional features (step 2008), and extraction of two-dimensional acoustical features (step 2014) proceed in a manner similar to steps 1902-1908 and 1914 of FIG. 19, respectively. Additionally, however, three-dimensional features are located and extracted from the three-dimensional volumetric representation of the breast volume in a manner that takes advantage of knowledge of the two-dimensional ROIs located in the thick-slice images at step 2004. At step 2106, the three-dimensional volumetric representation of the breast already exists by virtue of its computation from the initial raw ultrasound scans as part of the individual ultrasound slice generation process. At step 2018, ROIs are located in the thick-slice volume according to a method that takes advantage of the known two-dimensional ROI locations computed for the thick-slice images. For a given thick-slice image, there is a corresponding thick-slice volume contained in the three-dimensional volumetric representation of the breast. According to a preferred embodiment, the two-dimensional ROIs (x, z) found in that slick-slice image may be used as starting points in locating three-dimensional ROI locations (x, y, z) within that thick-slice volume. This can save computing time by reducing the ROI search to a one-dimensional search in the "y" direction for each (x, z) starting point.

At step 2020, the lesion borders are segmented at each ROI using a 3-dimensional segmentation algorithm. Any of a variety of three-dimensional segmentation algorithms can be used, including local thresholding algorithms, 3-D volume growing algorithms, or other algorithms as described, for example, in U.S. Pat. No. 6,317,617, which is incorporated by reference herein. At step 2022 three-dimensional acoustical features indicative of lesion suspiciousness are extracted for each candidate lesion. In one preferred embodiment, the three-dimensional features comprise one or more of the following features: a surface roughness metric for the candidate lesions, such as a surface area-to-volume ratio (higher ratios being associated with increased suspiciousness); a lesion compression metric that compares lesion depth in the direction of compression versus lesion height/width/area in a plane perpendicular to the direction of compression (if the lesion easily "squishes" in the direction of compression it is less suspicious); and volumetric echo uniformity metrics (a more uniform echo throughout the volume indicates less suspiciousness). Other three-dimensional features that can be used include three-dimensional spiculation metrics, three-dimensional density metrics, sphericity metrics, VDI metrics, shadow metrics, and other three-dimensional features described in the above references.

At step 2010, the results of all of the steps 2008, 2014, and 2022 are processed by one or more classifier algorithms. Extensions of known classification algorithms to data sets comprising combinations of two- and three-dimensional features could be carried out by a person skilled in the art without undue experimentation in view of the present disclosure. At step 2012, based on one or more scores computed during the classification step, CAD outputs are displayed.

Figure 20B:
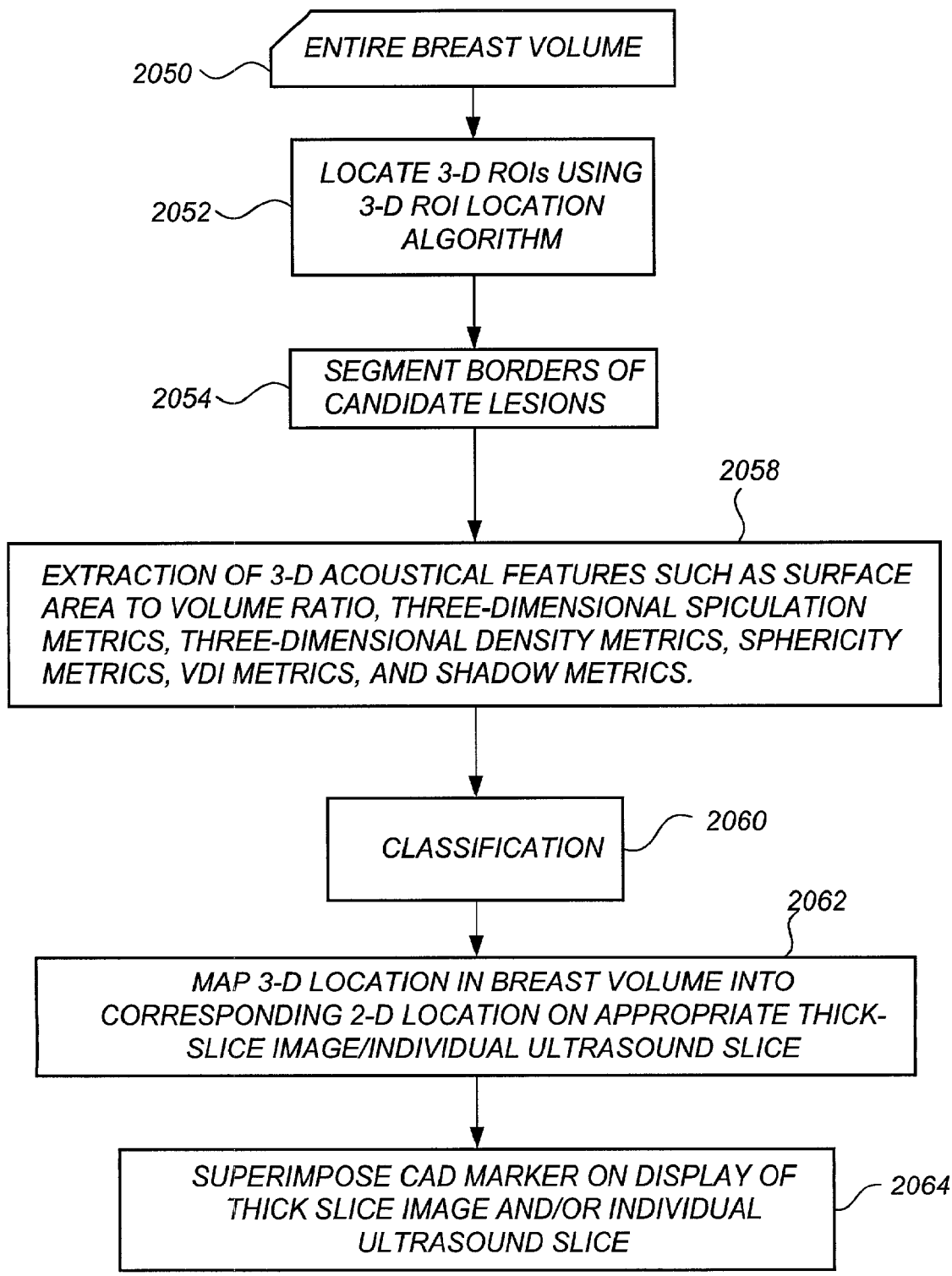
FIG. 20B illustrates steps for computer-aided diagnosis of adjunctive ultrasound data according to a preferred embodiment.

FIG. 20B illustrates steps for computer-aided diagnosis (CAD) of adjunctive ultrasound data according to a preferred embodiment, in which substantially all CAD processing is formed on the entire three-dimensional breast volume without regard to the thick-slice volumes. At step 2050 the entire breast volume exists by virtue of the three-dimensional volumetric representation of the breast computed from the initial raw ultrasound scans. At step 2052 ROI locations in the breast volume are determined according to a three-dimensional ROI detection algorithm. In one preferred embodiment, the three-dimensional ROI detection algorithm is similar to that used in step 2018 of FIG. 20A, except that it is applied to the whole breast volume at once rather than to separate thick-slice volumes. In another preferred embodiment, an ROI detection algorithm based on a three-dimensional Difference-of-Gaussians ("D.O.G.") operator is used, comprising an extension into three dimensions of the two-dimensional D.O.G. operator described, for example, at page 264 of Russ, *The Image Processing Handbook*, 3rd Edition, CRC Press/IEEE Press (1998).

At step 2054 the borders of candidate lesions are segmented at each ROI location using a three-dimensional segmentation algorithm. In one preferred embodiment, the three-dimensional segmentation algorithm is similar to that used in step 2020 of FIG. 20A. In another preferred embodiment, a three-dimensional region-growing algorithm is used similar to that described, for example, in the *Handbook of Medical Imaging*, Volume 2, supra at pp. 98-101. At step 2058, one or more three-dimensional features are extracted. The three-dimensional features may include three-dimensional spiculation metrics, three-dimensional density metrics, sphericity metrics, VDI metrics, shadow metrics, edge shadow metrics, border metrics, texture metrics, contrast metrics, size metrics, shape metrics, internal echo metrics, surface area-to-volume metrics, and other three-dimensional metrics.

At step 2060, any of a variety of known three-dimensional classifier algorithms is applied to the three-dimensional features to determine one or more metrics of suspiciousness therefrom. At step 2062, the locations of lesions found to require user attention are mapped from the breast volume into their corresponding thick-slice image. At step 2064, a marker for each such is placed on the relevant two-dimensional thick-slice image and/or the relevant individual ultrasound slice(s) on the user display.

Figure 21:
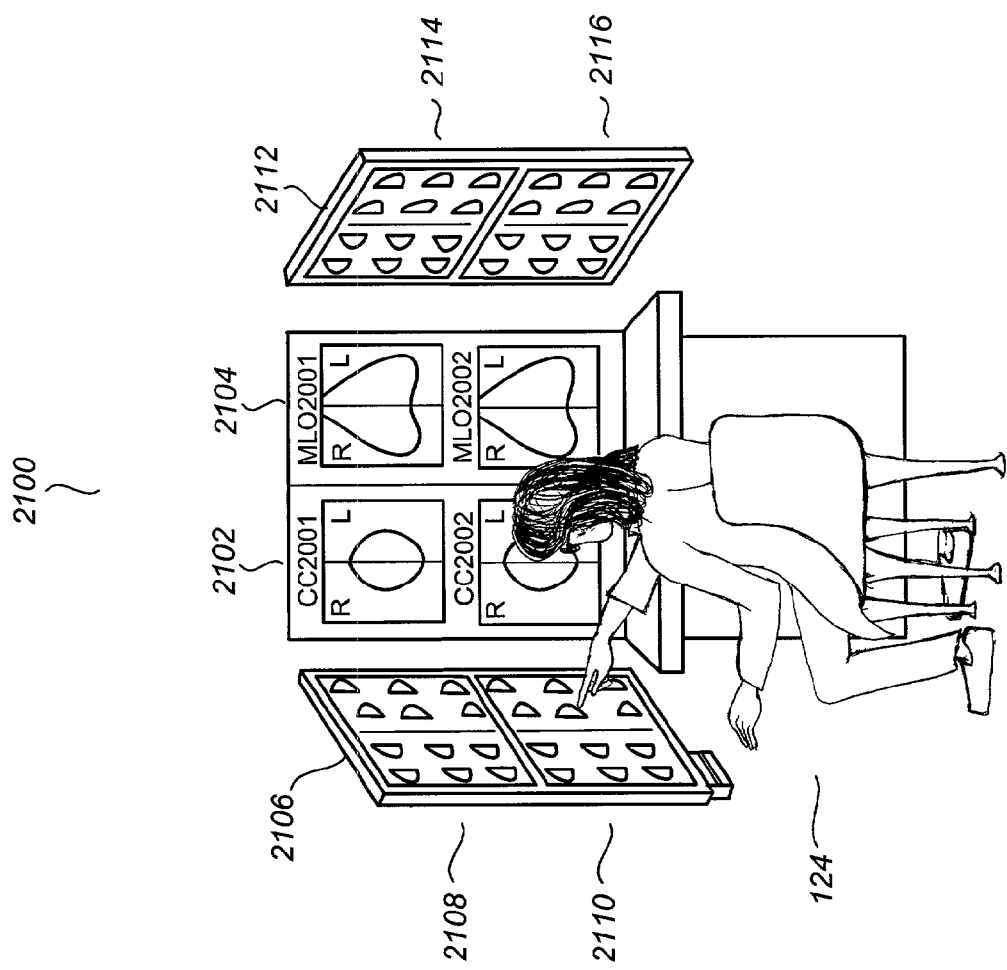
FIGS. 21-24 illustrates x-ray mammogram viewing stations with adjunctive ultrasound displays according to the preferred embodiments.

FIG. 21 illustrates an x-ray mammogram viewing station with adjunctive ultrasound displays according to a preferred embodiment in which the radiologist 124 is permitted to view the current x-ray mammogram against last year's results (or results from another previous time). An x-ray mammogram viewing station shows past and current CC x-ray mammogram views 2102, and adjacent thereto on the adjunct display 2106 is shown the corresponding past CC thick slices 2108 and current CC thick slices 2110. Likewise, the x-ray mammogram viewing station shows past and current MLO x-ray mammogram views 2104, and adjacent thereto on the adjunct display 2112 is shown the corresponding past MLO thick slices 2114 and current MLO thick slices 2116. Preferably, any given CC or MLO thick slice from any time period is positioned not more than 30 inches from its corresponding x-ray mammogram view from that time period or any other time period. Although data for only two years (or time periods) is shown in the example of FIG. 21, it is to be appreciated that the simultaneous display of any number of years (or time periods) of thick-slice images near their associated x-ray mammograms is within the scope of the preferred embodiments.

Figure 22:
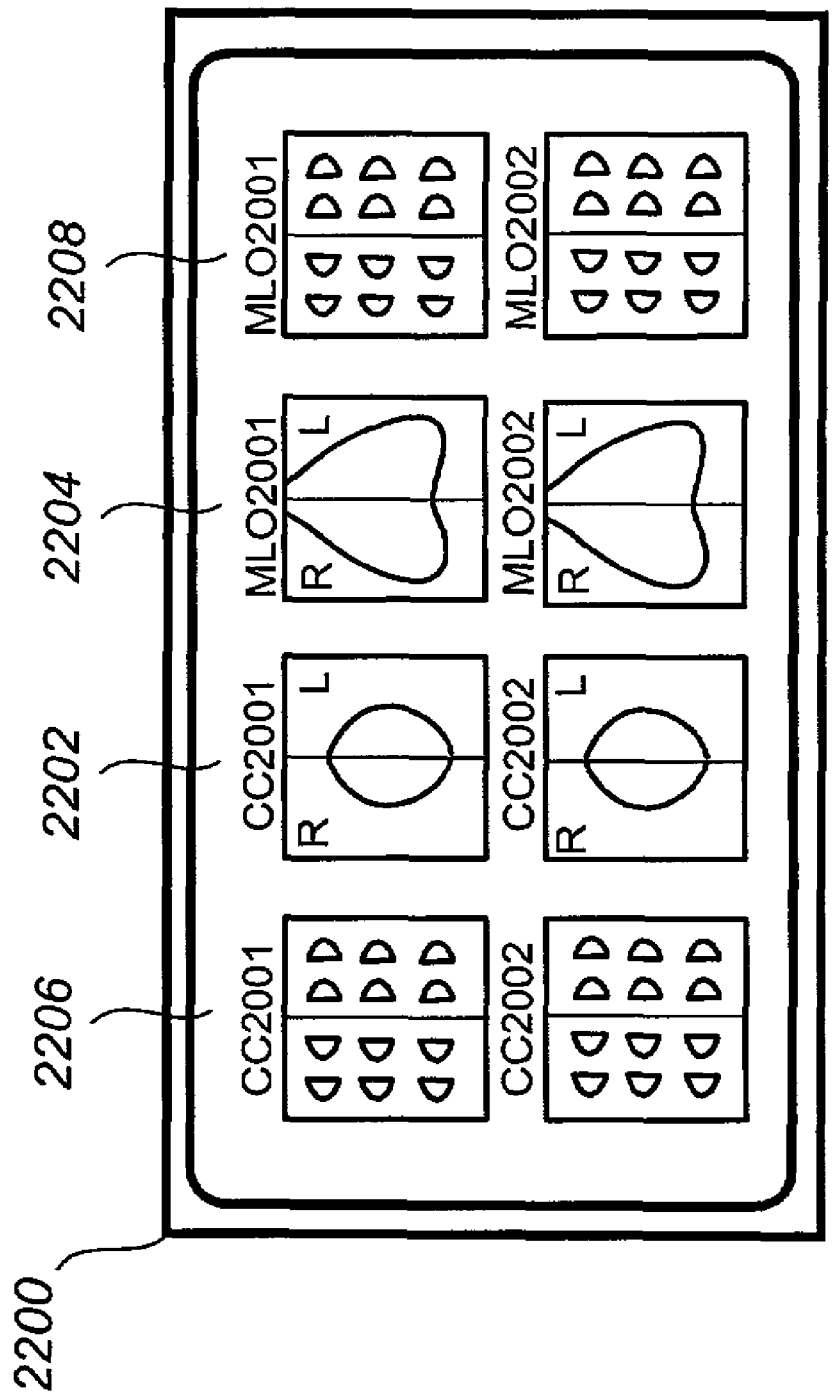

FIG. 22 illustrates an x-ray mammogram viewing monitor 2200 with adjunctive ultrasound displays according to another preferred embodiment, wherein all data including the x-ray mammograms are digital in form, and wherein the adjunctive ultrasound data is displayed near the x-ray mammogram data on a common monitor. Past and present CC thick slices 2206 are displayed near past and present CC x-ray mammogram views 2202, and past and present MLO thick slices 2208 are displayed near past and present MLO x-ray mammogram views 2204. The monitor 2200 may be, for example, a large-screen high-definition display such as an HDTV display, a high-definition projection monitor, or the like that is large enough to display the image data with sufficient resolution for breast cancer screening purposes.

Figure 23:
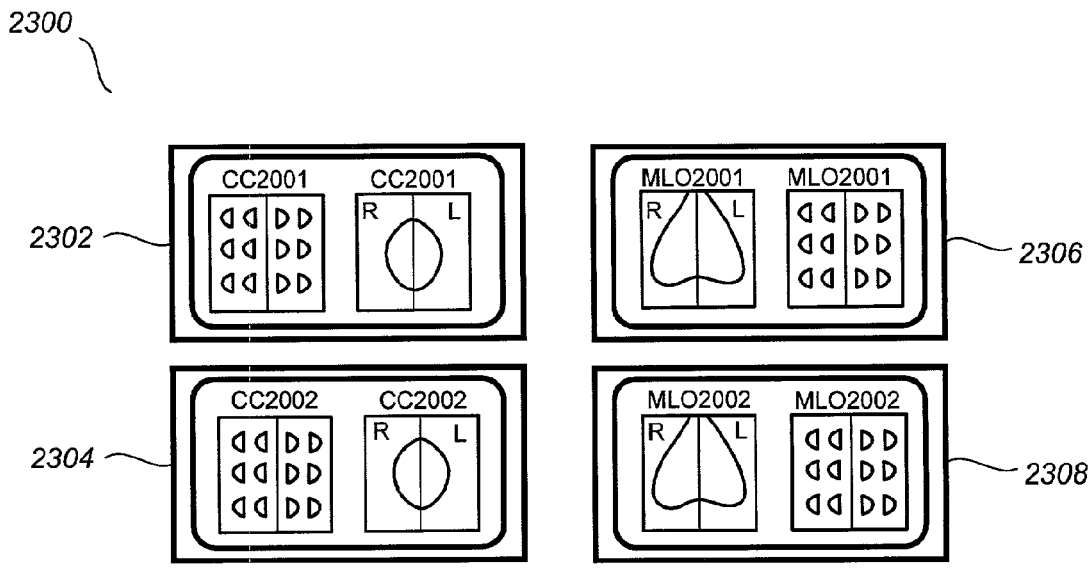
Figure 24:
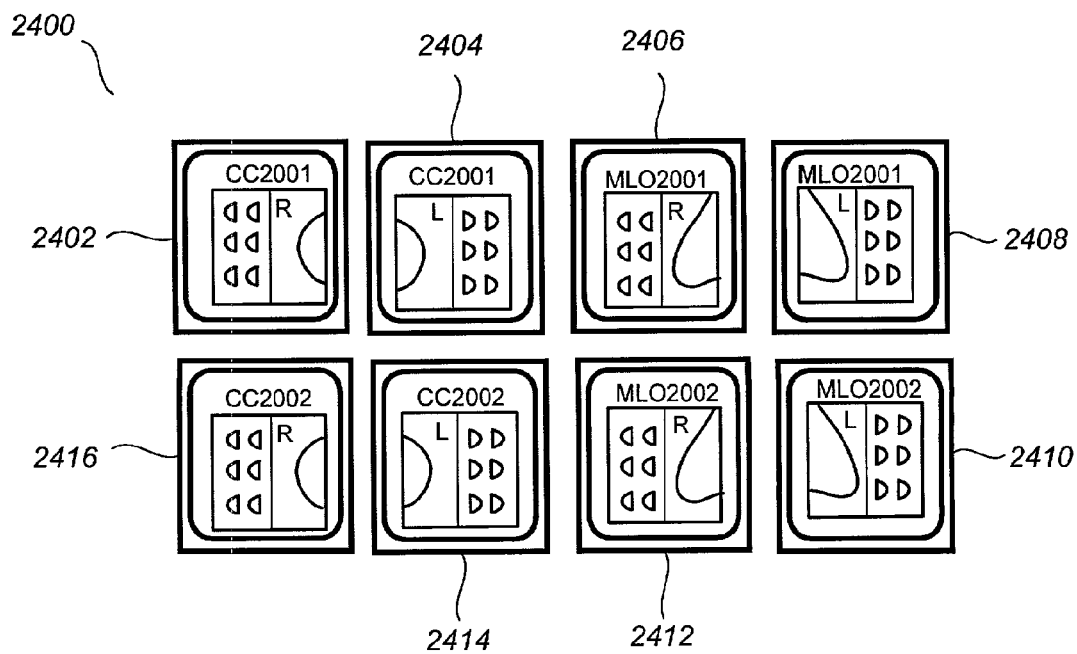

FIGS. 23-24 illustrate x-ray mammogram viewing monitors with adjunctive ultrasound displays according to other preferred embodiments, wherein different combinations of x-ray mammogram and adjunctive ultrasound data are displayed on different monitors placed close to each other. It is to be appreciated that the examples of FIGS. 22-24 are by no means limiting, and that many other combinations of monitor content and positioning are within the scope of the preferred embodiments.

Figure 25A:
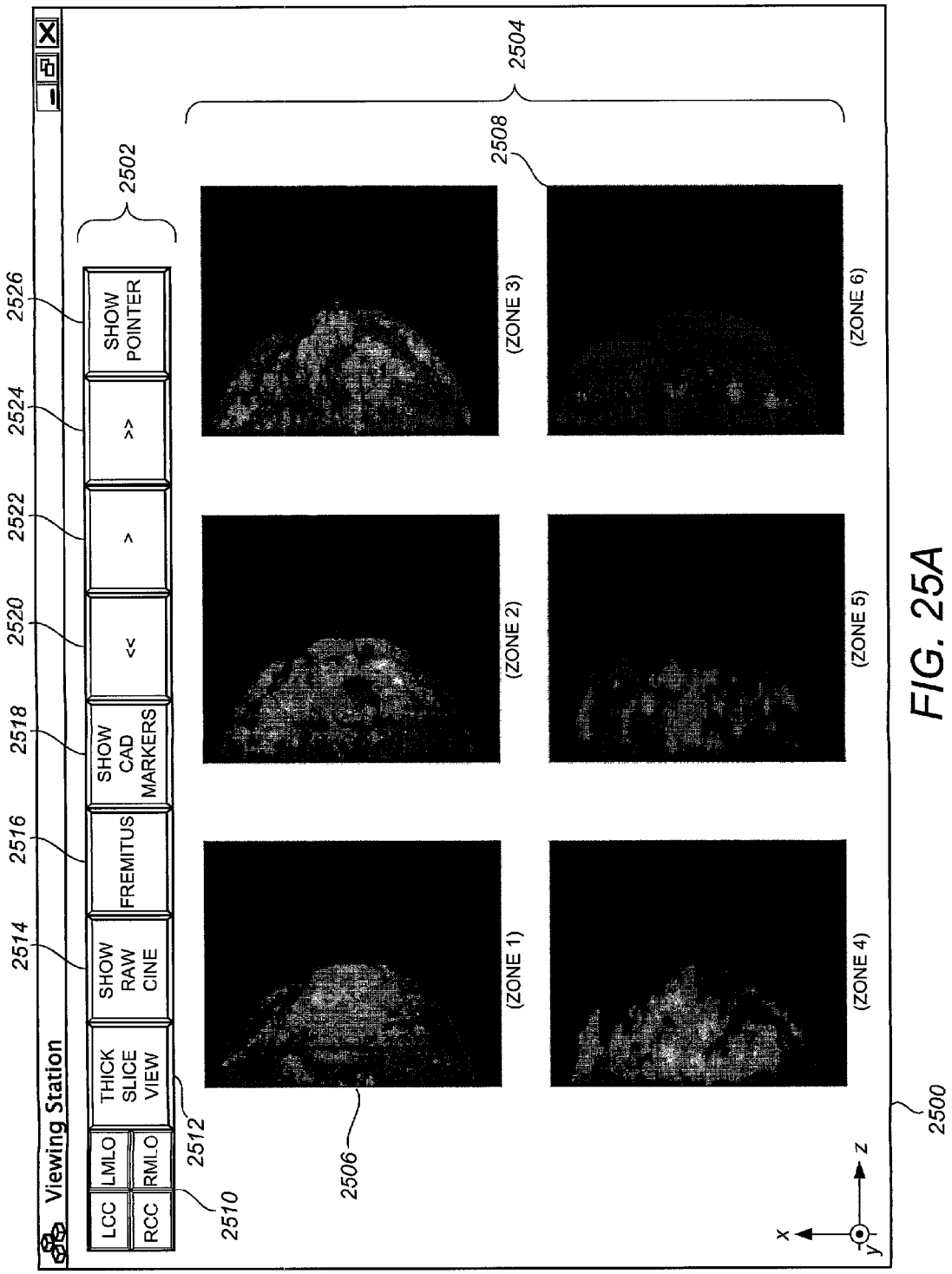
FIG. 25A illustrates an adjunct ultrasound display according to a preferred embodiment showing thumbnail thick slice views.

FIG. 25A illustrates an adjunct ultrasound display 2500 according to a preferred embodiment, which may be used alternatively or in conjunction with the adjunct ultrasound displays described supra. The adjunct ultrasound display 2500 may be implemented, for example, on a Microsoft Windows® 2000 operating system platform using Microsoft Visual C++. Adjunct ultrasound display 2500 is designed to interactively and intuitively display image information relating to a breast ultrasound scan. All computationally intensive computing algorithms (CAD, fremitus, etc.) are presumed to have already taken place in non-real time prior to invocation of the viewing program, although to scope of the preferred embodiments is not so limited. The precomputed images are stored, for example, in BMP format on a FAT32 or NFS file system and are associated by filename, with a first portion of the filename containing patient and scan data information and a second portion of the filename identifying the type of ultrasound image stored.

Adjunct ultrasound display 2500 generally has the look and feel of a conventional Windows® application. The user can supply inputs using a conventional personal computer keyboard and mouse (not shown). Context-sensitive soft buttons 2502 are provided that are selectable in a point-and-click fashion, and include a breast view selection button 2510, a thick slice view button 2512, a raw cine view button 2514, a fremitus button 2516, a CAD button 2518, a cine reverse button 2520, a cine play/pause button 2522, a cine forward button 2524, and a pointer show/hide button 2526. For clarity of description, a set of reference axes is displayed in the lower left hand corner of FIGS. 25A-25F, which may not appear on the actual output screen. For the purposes of describing the particular images of FIGS. 25A-25F, the "x" direction represents the lateral (left-right) direction across the chest, the "y" direction represents the vertical (head-toe) direction, and the "z" direction represents the anterior-posterior direction (pointing outward from the chest wall).

In a first view, adjunct ultrasound display 2500 shows thick-slice thumbnails 2504 as illustrated in FIG. 25A. A first thick-slice thumbnail image 2506 represents the uppermost thick-slice region of the breast (see region "A" of FIG. 9A) that is denoted zone 1, the thick-slice thumbnails proceeding in order through a final thick-slice thumbnail image 2508 representing the lowermost thick-slice region (see region "F" of FIG. 9A). Depending on the number of thick-slice regions in the breast, the thick-slice thumbnail images 2504 can actually be quite large, approaching several inches in size. Indeed, in one preferred embodiment in which there is a large enough display monitor, the thumbnail images can actually be full-scale, although this preferred embodiment would be more expensive than if smaller thumbnails thick-slice images are displayed.

Figure 25B:
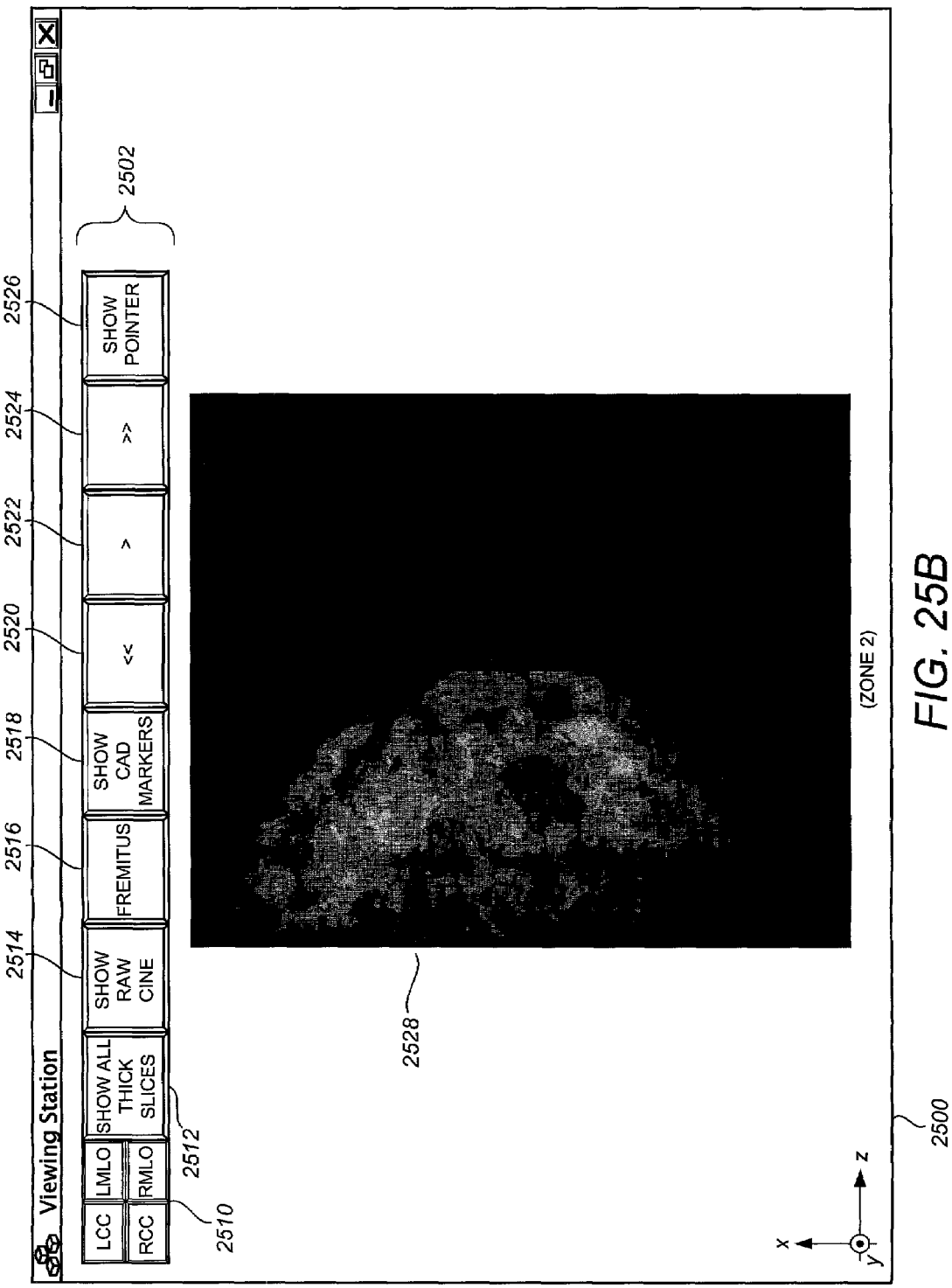
FIG. 25B illustrates an adjunct ultrasound display according to a preferred embodiment showing a single thick slice image.

The soft buttons 2502 are context sensitive, displaying options appropriate to the present state of the adjunct ultrasound display 2500. Generally speaking, the user has the option of pressing one or more of the soft buttons 2502, and/or one or more of the onscreen images being displayed and/or a particular location thereon, to proceed to the desired display of interest. The breast view selection button 2510, which is actually four smaller buttons, enters the user into one of the LCC, RCC, LMLO, or RMLO view. It is to be appreciated that while FIGS. 25A-25F show data for the LCC or RCC view, equivalent display options for the LMLO/RMLO view are also provided and are within the scope of the preferred embodiments. When the view of FIG. 25A is shown, the thick slice view button 2512 reads "THICK SLICE VIEW" and, if the user clicks on one of the thick-slice images, a single full-scale thick-slice image 2528 of FIG. 25B appears. When the view of FIG. 25B is showing, the thick slice view button 2512 then reads SHOW ALL THICK SLICES and, if pressed, returns the display to the thick-slice thumbnail display of FIG. 25A. Also when the view of FIG. 25A is shown, if the cine play/pause button 2522 is pressed, a cine presentation of individual ultrasound slices parallel to the CC plane (x-z plane) is presented, one such individual ultrasound slice 2530 being shown in FIG. 25C, the cine presentation beginning at the uppermost slice of the breast volume and proceeding to the lowermost slice.

Figure 25C:
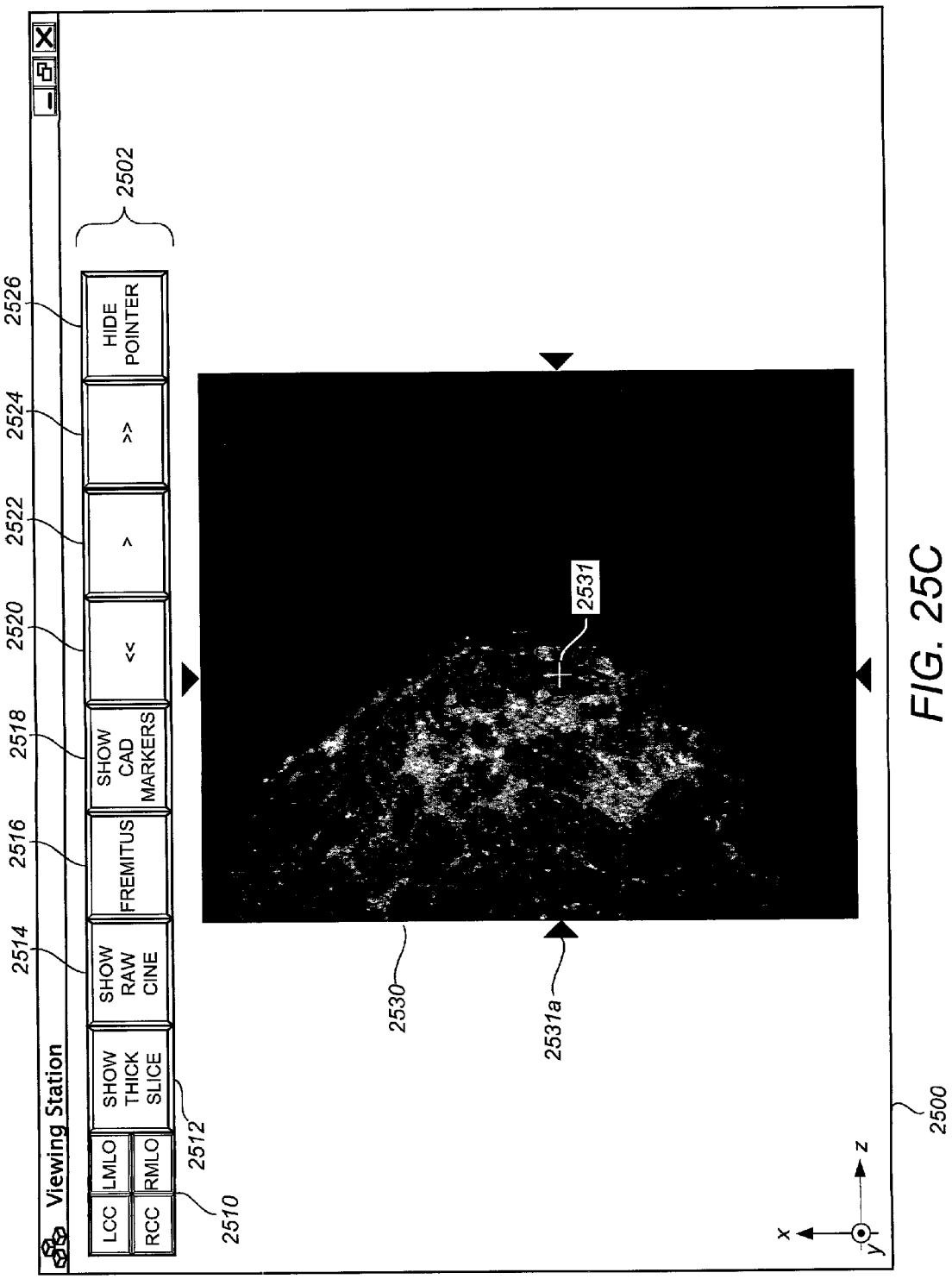
FIG. 25C illustrates an adjunct ultrasound display according to a preferred embodiment showing a paused cine presentation of individual ultrasound slices corresponding to the thick slice image of FIG. 25B.

When the view of FIG. 25B is showing and the cine play/pause button 2522 is pressed, a cine presentation of individual ultrasound slices corresponding to the thick-slice image being displayed (zone 2 for the particular example of FIG. 25B) is also presented as in FIG. 25C, except that the cine presentation begins at the uppermost slice of the zone 2 thick-slice volume and proceeds to the lowermost slice of that thick-slice volume. With reference to FIG. 25C, the user uses the cine control buttons 2520-2524 to control the playback. While in forward play mode, the play/pause button 2522 indicates a PAUSE icon (not shown), and while in pause mode as indicated in FIG. 25C, the play/pause button 2522 indicates a forward play (">") symbol.

The view of FIG. 25C is a paused cine view of individual ultrasound slices that are computed from a 3-D volumetric representation of the breast from raw ultrasound slices. The raw ultrasound slices are themselves taken in planes parallel to the y-z plane as the ultrasound probe is swept across the breast in a lateral (right-to-left) direction, which corresponds to the "x" direction in the image of FIG. 25C.

Figure 25D:
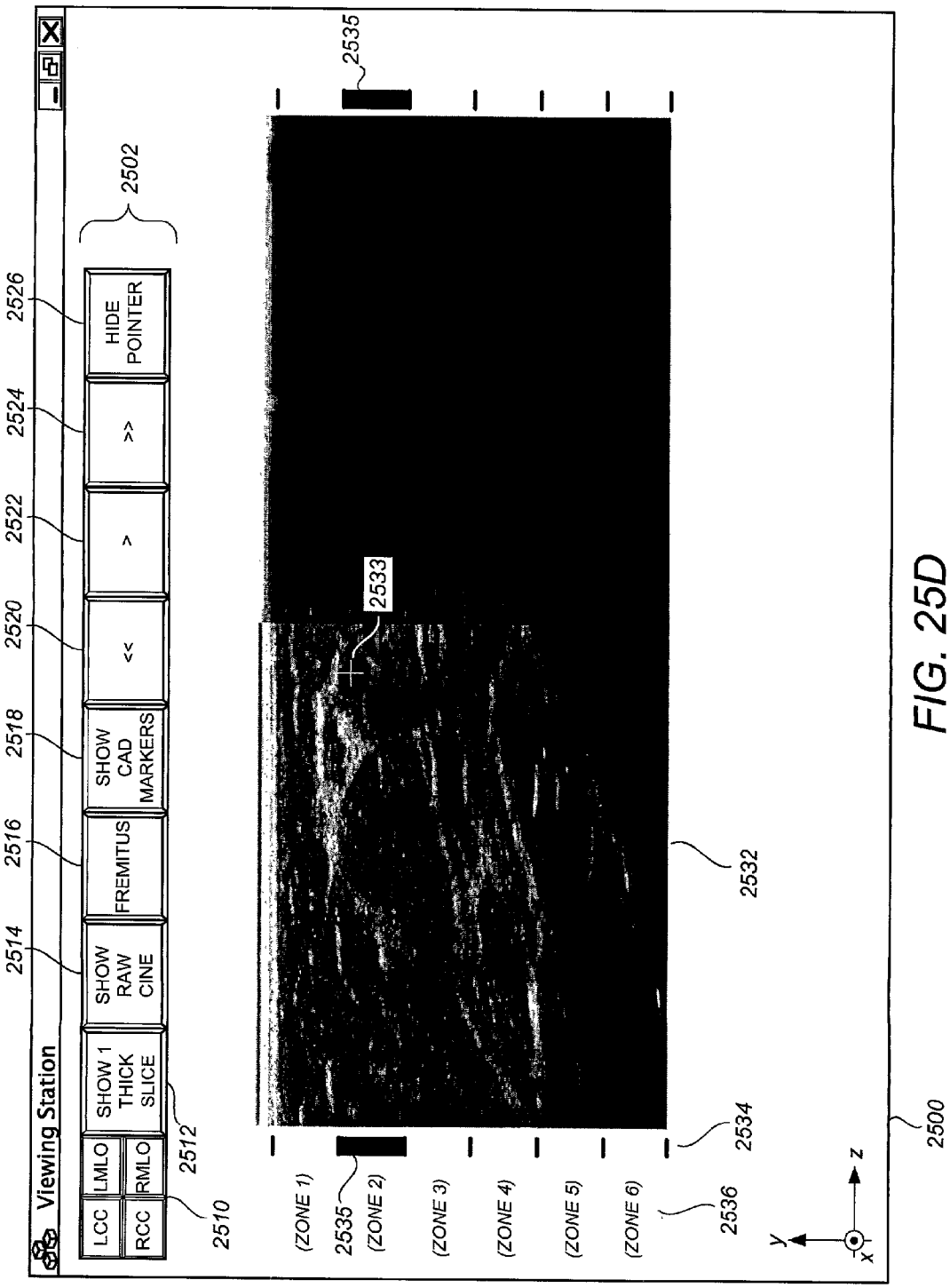
FIG. 25D illustrates an adjunct ultrasound display according to a preferred embodiment showing a paused cine presentation of raw B-mode ultrasound slices corresponding to the ultrasound data of FIGS. 25A-25C.

FIG. 25D illustrates a raw B-mode frame 2532. This view can be invoked in several ways. The raw B-mode frame 2532 represents one frame of a cine presentation of raw B-mode frames that can be controlled by the cine control buttons 2520-2524 when the view of FIG. 25D is being displayed. If the view of FIG. 25A or FIG. 25B is showing and the user selects the raw cine view button 2514, the view of FIG. 25D will be entered and will proceed to display a cine presentation of all raw B-mode frames as gathered during the raw ultrasound scanning process. If the view of FIG. 25C is showing and the user clicks anywhere on the image, the view of FIG. 25D appears for a plane corresponding to the "x" location of the cursor when clicked. As with the other images shown in FIGS. 25A-25F, the raw B-mode image 2532 is a "stitched" image comprising two halves corresponding to different passes of the ultrasound probe over the breast. In alternative preferred embodiments in which a wider probe is used, the need for multiple probe passes and image stitching would not be necessary. Zone markers 2534 are provided on the display of FIG. 25D that demarcate the different thick-slice volumes (zones) 1-6 of the breast, as well as a zone indicator 2535 that indicates the zone that was being displayed if the prior view was of FIG. 25B or FIG. 25C.

According to a preferred embodiment, a convenient location-mapping feature is provided to assist the user in switching back and forth between the views of FIGS. 25C and 25D. Starting, for example, in the view of FIG. 25D, which shows a given raw B-mode frame 2532 taken at a particular lateral location "x1", the user can click the cursor on a given point (y1, z1) on that image. Responsive to that click, the view of FIG. 25C is presented showing the individual ultrasound slice that corresponds to the vertical "y1" position. Furthermore, a pointer 2531 appears on the image of FIG. 25C at (x1, z1). This is especially useful in correlating breast locations where the z-axis scales of FIGS. 25C-25D are not the same. Likewise, starting, for example, on the view of FIG. 25C, which shows a given individual ultrasound slice 2530 computed for a particular vertical location "y1", the user can click the cursor on a given point (x1, z1) in that image. Responsive to that click, the view of FIG. 25D is presented showing the raw B-mode ultrasound frame that corresponds to the lateral position "x1" of that point, and a pointer 2533 appears on the image of FIG. 25D at (y1, z1). The pointer can be removed from the current view by selecting the HIDE POINTER button 2526.

Figure 25E:
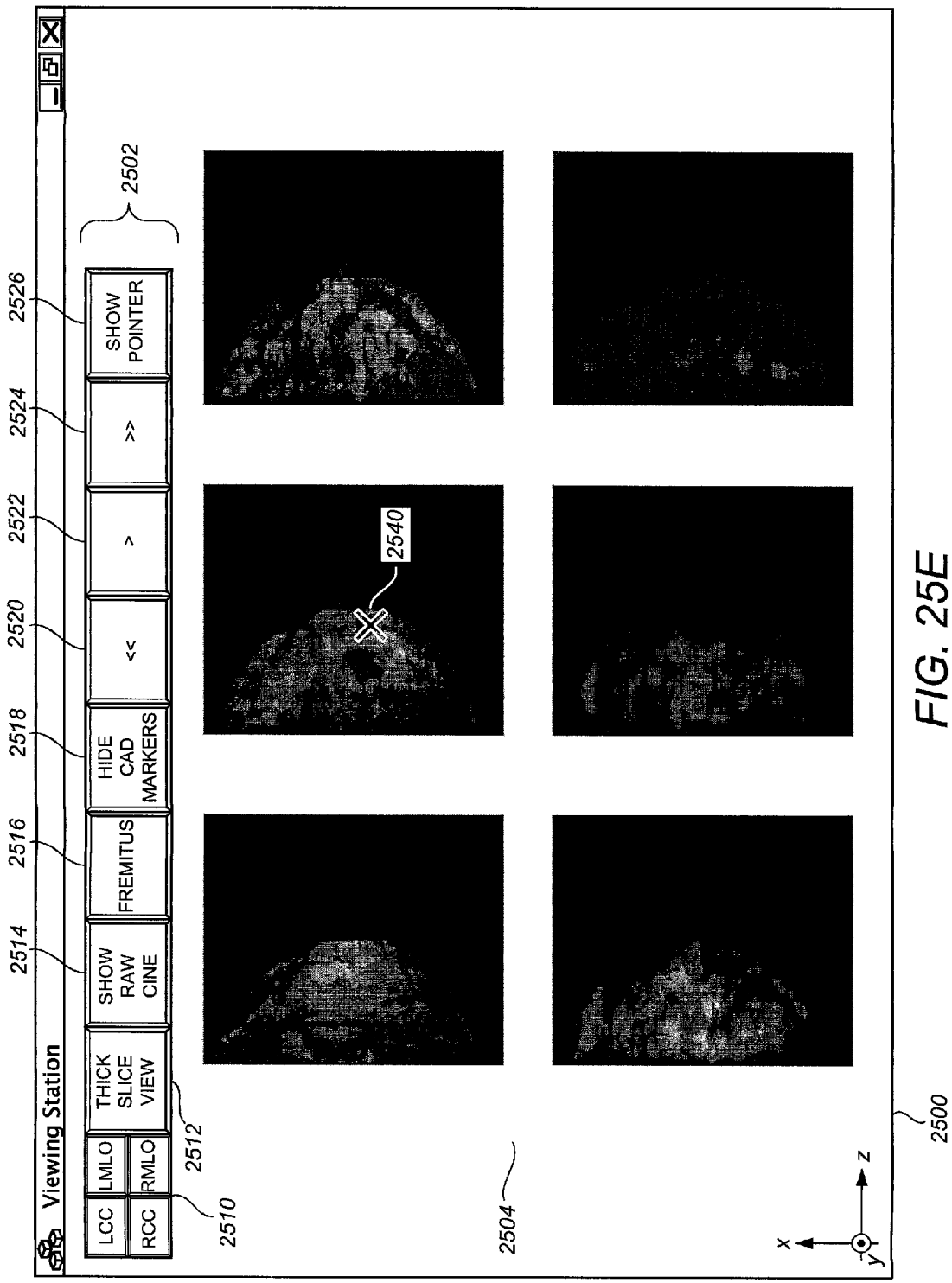
FIG. 25E illustrates an adjunct ultrasound display according to a preferred embodiment showing thumbnail thick slice views with superimposed CAD markers.

The display of FIG. 25D also corresponds to a single frame of a cine loop presentation of the raw B-mode data that was acquired. Accordingly, the display of FIG. 25D is responsive to activation of any of the cine controls 2520-2524 and will proceed to display the raw B-mode ultrasound frames of the initial scans taken parallel to the y-z plane as the probe was translated in the x direction. If the user presses the thick slice view button 2512 when the view of FIG. 25D is displayed, the display will revert to the thick-slice display of FIG. 25B for the zone indicated by the zone markers 2535. FIG. 25E illustrates the adjunct ultrasound display 2500 showing the thumbnail thick slice views 2504 with a superimposed CAD marker 2540. This view is enabled by pressing the CAD button 2518 when the display of FIG. 25A is active. After being pressed to make the CAD markers appear, the CAD button 2518 reads HIDE CAD MARKERS, and the CAD markers are removed if the CAD button 2518 is pressed again.

Figure 25F:
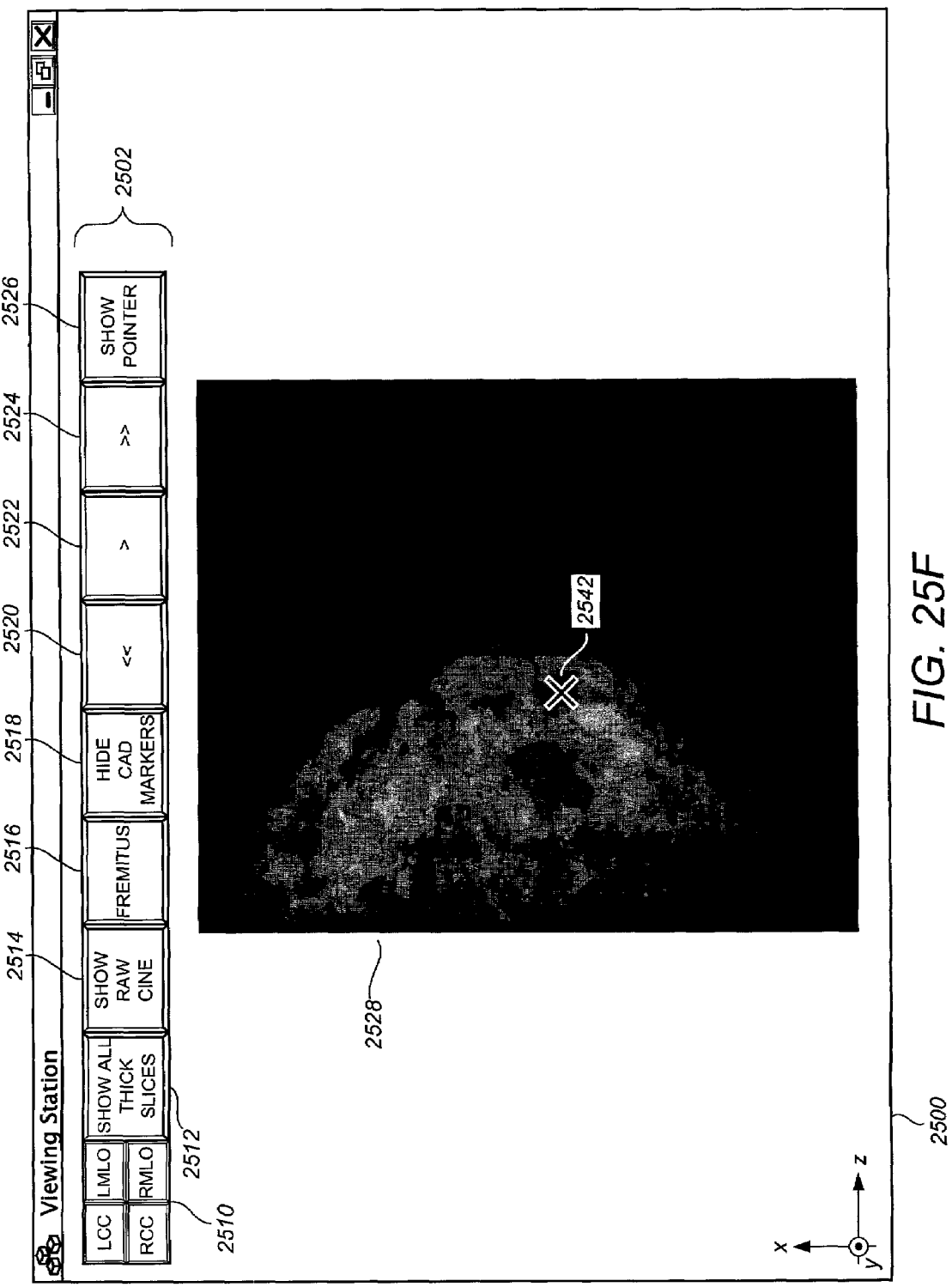
FIG. 25F illustrates an adjunct ultrasound display according to a preferred embodiment showing a single thick slice image with superimposed CAD markers.

FIG. 25F illustrates the adjunct ultrasound display 2500 showing the single thick slice view 2528 with a superimposed CAD marker 2542, which is enabled by pressing CAD button 2518 when the display of FIG. 25B is active. In one preferred embodiment, a star or cross-hair symbol is used to denote a suspicious mass, while triangles are drawn around suspected microcalcifications.

Although described in the preferred embodiments supra in terms of a computer display for viewing the adjunctive ultrasound data, it is to be appreciated that any of a wide variety of output modalities may be used without departing from the scope of the preferred embodiments, including paper printouts, film printouts, and holographic displays. For these output modalities, a manual indexing system can be used to order the images, with the thumbnail thick-slice image views serving as a "table of contents" for the book of images. All of the thick-slice images preferably should be provided in full scale, preferably with the CAD results superimposed thereon, with ordered subsets (e.g., every $k^{th}$ member) of the raw B-mode images and the component ultrasound slices also being provided. In view of the large amount of digital data associated with each adjunctive ultrasound scan session for each patient, which can extend into the gigabyte range if uncompressed, it may be desirable to archive the data in such a hardcopy format. Alternatively or in conjunction therewith, the digital data can be compressed and digitally archived. One particularly desirable compression algorithm is the JPG (Joint Photographic Experts Group) algorithm, which has been found to work very efficiently with ultrasound images. Using a JPG algorithm, a data compression ratio of 20:1 (as compared to an original uncompressed BMP format) or better can be achieved with negligible loss of information.

As known in the art, many conventional ultrasound machines measure acoustic reflectivity of internal tissues at a higher bitwise precision (e.g., 14 bits per pixel) than is displayed on the output display monitor (e.g., 8 bits per pixel). In the examples herein, 14 bits are assumed for the higher precision gray scale value and 8 bits are assumed for the lower precision gray scale value, it being understood that these are nonlimiting examples. After the higher-precision measurements are acquired, conventional ultrasound machines perform a lossy gray scale compression algorithm that maps the higher precision 14-bit pixel values into the lower-precision 8-bit pixel values. Generally speaking, conventional ultrasound systems comprise high-speed internal hardware that performs the gray scale compression in real time prior to display, printout, storage, or other processing of the ultrasound image data by "downstream" systems. One reason the gray scale compression algorithm is performed at "upstream" points in the data flow process is to achieve better cost efficiency, it being more cost intensive to carry along an entire 14 bits of precision in the data stream that cannot be appreciated on an 8 bit display.

The simplest gray scale compression algorithm, of course, is a linear mapping that simply chops off the 6 least significant bits of a 14-bit pixel value to achieve an 8-bit pixel value. Instead, however, most conventional ultrasound systems perform a nonlinear mapping designed to enhance image contrast on the output display while also reducing image precision from 14 bits to 8 bits. Unfortunately, in the output images resulting from these conventional nonlinear mappings, it is often difficult to perceive microcalcifications, which are very small (e.g., 0.1 mm-0.3 mm diameter), very hard, and very acoustically reflective objects known to be a local by-product of some breast tumors, and which would be desirable to detect in ultrasound images.

Figure 26:
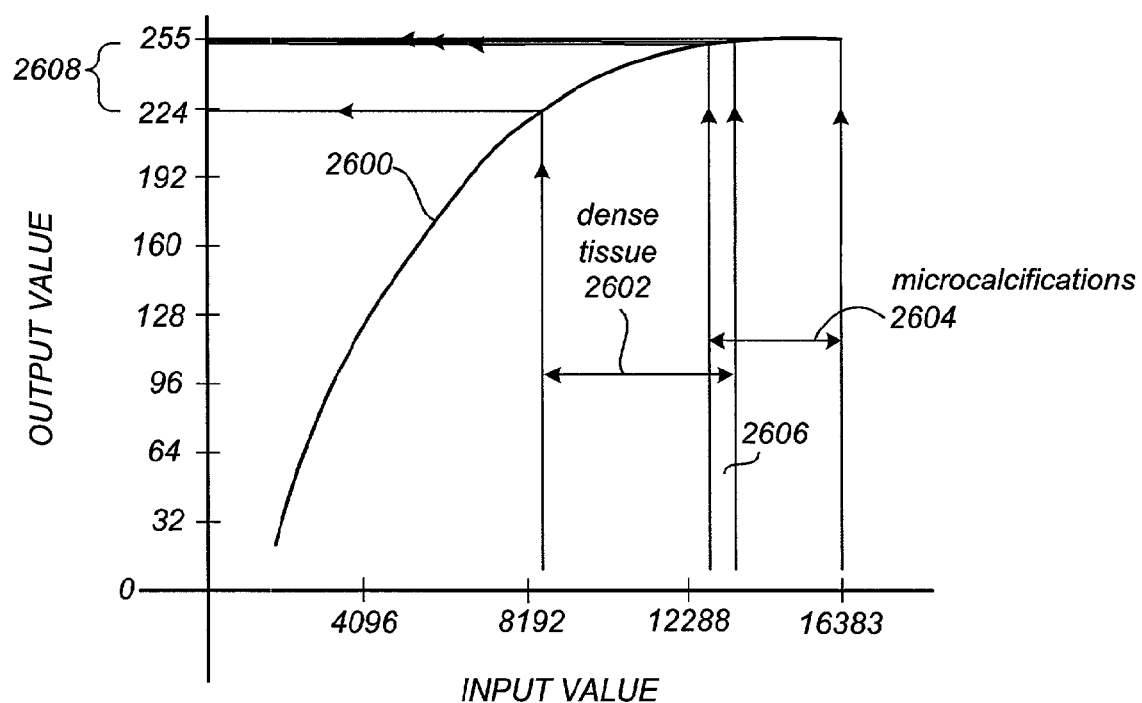
FIG. 26 illustrates a plot of a conventional contrast enhancing remapping curve.

FIG. 26 illustrates a conceptual plot of a conventional remapping curve 2600 according to a conventional gray scale compression algorithm. Each 14-bit pixel value is remapped through the remapping curve 2600 into an 8-bit pixel value by high-speed upstream hardware components of the ultrasound system prior to display, printout, storage, or other downstream data processing. The remapping curve 2600 is commonly a quasi-logarithmic curve designed to maximize the contrast effect between denser areas and less dense areas of the breast. As indicated in FIG. 26, dense breast tissue usually has high acoustic reflectivities falling in the range 2602 of FIG. 26, while typical microcalcifications usually have even higher acoustic reflectivities falling in the range 2604 of FIG. 26, there being some degree of overlap 2606 between the two ranges. Unfortunately, as indicated in FIG. 26, the microcalcifications and the dense breast tissues tend to map into a very high saturation range 2608 of output levels on the display monitor. Accordingly, in view of their small size, these microcalcifications are often not clearly visible on the output display, especially when surrounded by dense breast tissue.

According to a preferred embodiment, a computer-assisted microcalcification-highlighting algorithm is performed whose output is optionally displayed by the user in an overlay fashion on the thick-slice images and/or individual ultrasound slices. In this preferred embodiment, it is presumed that the scanning ultrasound system has already performed the 14-to-8 bit compression during the scanning process using the conventional remapping curve 2600 of FIG. 26. First, the 8-bit image is thresholded on a pixel-by-pixel basis using a predetermined threshold value $T_{mc}$, the threshold value $T_{mc}$ being selected to separate the microcalcifications from the dense breast tissue and other breast tissue, in a statistically reliable manner. In one preferred embodiment, the threshold value $T_{mc}$ is selected to lie in the middle of the overlap region 2606 shown in FIG. 26, which can be empirically determined from a population of sample images. For those pixels lying above the threshold $T_{mc}$, simple region-growing algorithms are performed in which neighboring above-threshold pixels are clustered together. Any cluster having an average diameter greater than a predetermined size threshold related to microcalcification size is discarded. In one preferred embodiment, this predetermined size threshold is about 1 mm. The remaining clusters constitute the locations that will be highlighted on the microcalcification-enhanced overlay display. When this feature is invoked by the user, these clusters are displayed in a highly noticeable color, e.g. a bright pink or blue, on an otherwise black-and-white display of the thick-slice image or individual ultrasound slice.

According to another preferred embodiment, referring back to the overall adjunctive ultrasound system of FIG. 1, the scanning ultrasound system 118 is configured to simply pass along the entire 14-bit pixel values to the adjunctive ultrasound server 106 without compressing the data to 8 bits. Substantially all processing is performed on 14-bit data instead of 8 bit data. In this case, the threshold $T_{mc}$ can be set to a very high value near the maximum 14-bit value for more statistically reliable separation of microcalcifications from dense breast tissue. The adjunctive ultrasound display, of course, will usually have only 8 bits of dynamic range. The user may elect, either directly through keyboard inputs or indirectly through brightness/contrast controls, the type of 14-to-8 bit compression to be used prior to display. Again, it is to be appreciated that each of these choices is within the scope of the preferred embodiments.

FIGS. 27-31 illustrate conceptual diagrams of thick-slice regions as superimposed onto a breast 2702 for the purpose of further describing the nature of the thick-slice regions and images according to the preferred embodiments. In the examples of FIGS. 27-31, the thick-slice regions are parallel to the standard MLO x-ray mammogram view plane, i.e., the y-z plane in FIG. 27, it being understood that similar descriptions apply to CC thick-slice regions, i.e., the x-z plane in FIG. 27, or to other standard or custom x-ray mammogram view planes. In the embodiment of FIG. 27, thick-slice regions 2704 are non-overlapping and have a uniform thickness T. Preferably, the thickness T lies between 0.5 cm to 1.2 cm for capturing suspicious masses within that size range. For a typical case in which there are perhaps 400 individual ultrasound slices taken for the entire breast volume, each of the eight (8) thick-slice images are generated by mathematically combining (e.g., arithmetically averaging) about 50 individual ultrasound slices.

An intrinsic benefit of thick-slice generation according to the preferred embodiments is an inherent spatial filtering effect that removes noise while preserving structures dimensioned on the order of the slice thickness T or larger. As indicated in FIG. 28, the thickness T of the thick-slice regions can be reduced to increase sensitivity to smaller lesions. As indicated in FIG. 29, the thickness T of the thick-slice regions can be increased to further reduce noise effects and to capture only the larger lesions. Thus, the slice thickness T also serves as a spatial filtering parameter in addition to dictating the number of thick slices requiring display. While the above stated slice thickness range of 5 mm-12 mm is generally preferred, it has been found that useful results can be obtained with slice thicknesses ranging from 2 mm-20 mm.

Whereas the thick-slice regions of FIGS. 27-29 are non-overlapping in space, FIG. 30 illustrates overlapping thick-slice regions 3004. In this embodiment, each thick-slice region is quite thick (e.g., T=20 mm), but there is a spatial overlap among adjacent slices (e.g., V=40% overlap on each side) so that a sufficient number of images are available for viewing by the radiologist. Accordingly, the overlapping thick-slice embodiment of FIG. 30 offers the advantages of very thick thick-slice regions, while avoiding the limited visual data problems associated with very thick thick-slice regions when they are non-overlapping, as in FIG. 29.

Figure 31:
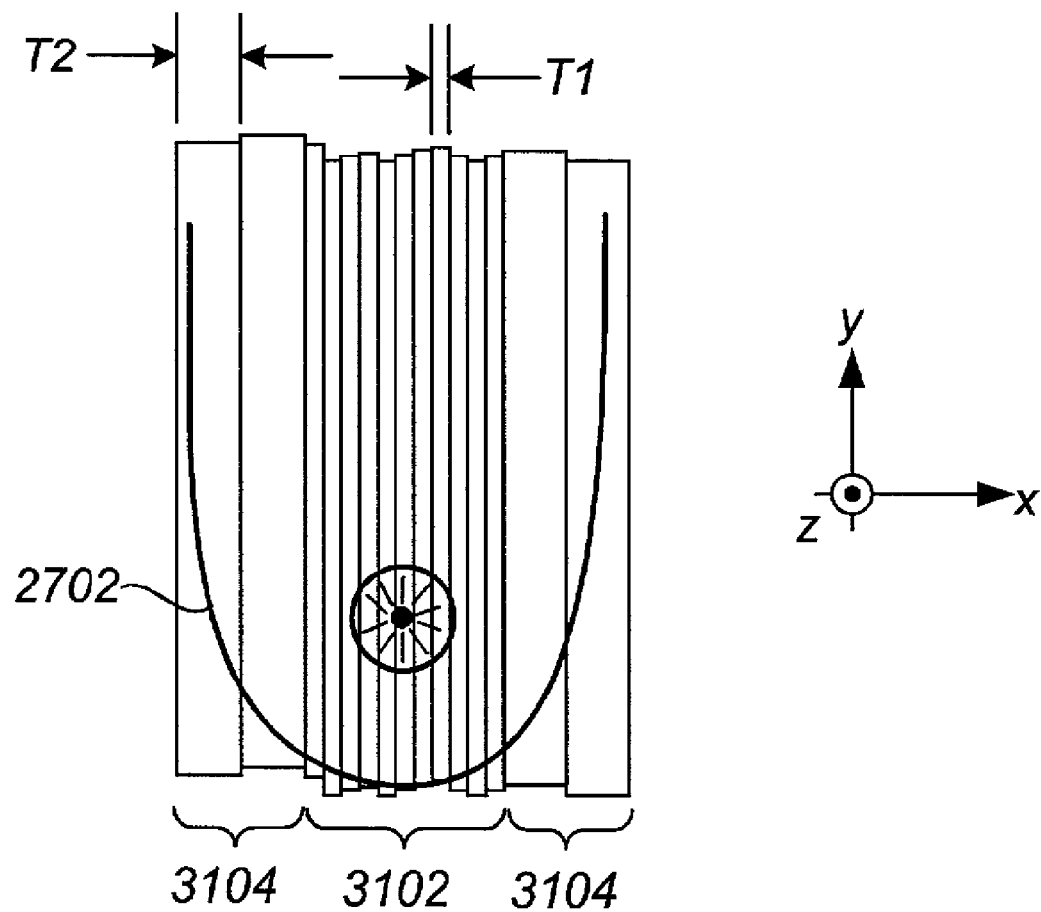

FIG. 31 illustrates a conceptual diagram of thick-slice regions as superimposed onto a breast 2702, wherein a first set of thick-slice regions 3102 near the center plane of the breast have a first thickness T1, and wherein second set of thick-slice regions 3104 near the outer planes of the breast have a second thickness T2>T1. In this preferred embodiment, the thinner inner thick-slice regions 3102 provide for increased spatial sensitivity in the inner planes of the breast, where cancerous lesions are more likely to occur. The thicker outer thick-slice regions 3104 provide the ability to reduce the number images that need to be viewed by the radiologist on the adjunctive ultrasound output display, the reduced sensitivity being acceptable because cancerous lesions are less common near the outer planes of the breast. Also within the scope of the preferred embodiments are thick-slice regions of more than two different thicknesses, and thick-slice regions that both (i) spatially overlap each other, and (ii) are of two or more different thicknesses.

Figure 32:
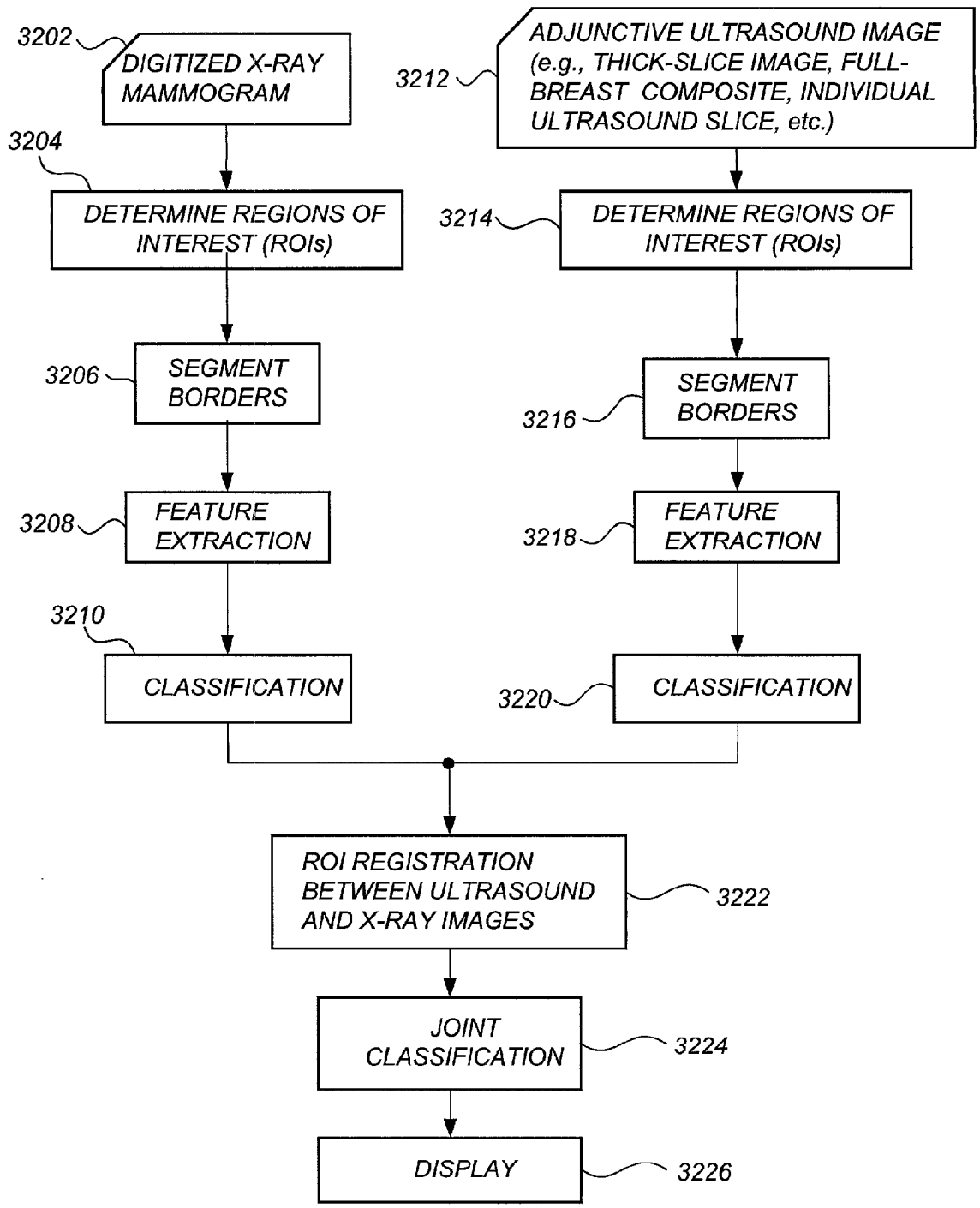
FIG. 32 illustrates steps for joint computer-aided diagnosis of digitized x-ray mammogram data and adjunctive ultrasound data according to a preferred embodiment.

FIG. 32 illustrates steps for joint computer-aided diagnosis of digitized x-ray mammogram data and adjunctive ultrasound data according to a preferred embodiment. Using known methods such as those described in U.S. Pat. No. 5,133,020, supra, x-ray CAD algorithms are performed including the steps of acquiring a digitized x-ray mammogram (step 3202), determining regions of interest (ROIs) (step 3204), segmenting (step 3206), extracting features indicative of lesion suspiciousness (step 3208), and classification (step 3210). A scalar or vector index of suspiciousness ("score") results from the x-ray CAD algorithm for each ROI. In a separate process, CAD algorithms are performed on adjunctive ultrasound image data (e.g., thick-slice image, full-breast composite, individual ultrasound slice, etc.) including the steps of acquiring the adjunctive ultrasound image data (step 3212), determining ROIs (step 3214), segmenting (step 3216), extracting features indicative of lesion suspiciousness (step 3218), and classification (step 3220). The steps 3212-3220 are carried out, for example, according to the adjunctive ultrasound CAD algorithms described supra with respect to FIGS. 19 and 20. The adjunctive ultrasound CAD algorithm also yields a scalar or vector "score" corresponding to lesion suspiciousness for each ROI.

At step 3222, regions of interest (ROIs) in the x-ray mammogram and adjunctive ultrasound images are registered with each other. Preferably, the x-ray and ultrasound ROIs are registered without the need for traditional registration of the entire x-ray and ultrasound images, which can be complex and time-consuming. Rather, a simple but statistically reliable lesion-centric registration process using nipple distance information, or using a combination of nipple distance information and nipple angle information, is used to match corresponding regions of interest in the x-ray mammogram view and the adjunctive ultrasound views, as is described further infra with respect to FIGS. 33-36.

At step 3224, each ROI is jointly classified using the scores from both the x-ray CAD process and the adjunctive ultrasound CAD process. By way of example, if the x-ray CAD algorithm and the adjunctive ultrasound CAD algorithm each yield a score that is a single, scalar metric of lesion suspiciousness (e.g., $S_x$ and $S_u$, respectively), these metrics can be added at step 3224 to yield an overall joint score $S_{joint} = S_x + S_u$ for that ROI. If a given ROI in the x-ray mammogram does not map into a corresponding ROI in the adjunctive ultrasound view, the value $S_u$ is set to zero by default, and the joint score $S_{joint}$ for that ROI is simply equal to $S_x$. Likewise, if a given ROI in the adjunctive ultrasound view does not map into a corresponding ROI in the x-ray mammogram, the value $S_x$ is set to zero by default, and the joint score $S_{joint}$ for that ROI is simply equal to $S_u$. In another preferred embodiment, the joint score can be a weighted combination of the individual scores, e.g., $S_{joint} = aS_x + bS_u$. At step 3226, the x-ray mammogram and/or the adjunctive ultrasound images are displayed in a manner that communicates lesion suspiciousness according to the joint score $S_{joint}$. It is to be appreciated that the examples given here are by way of illustration only, and that many different methods for combining the scalar or vector scores from the x-ray and ultrasound CAD algorithms is within the scope of the preferred embodiments.

Figure 33:
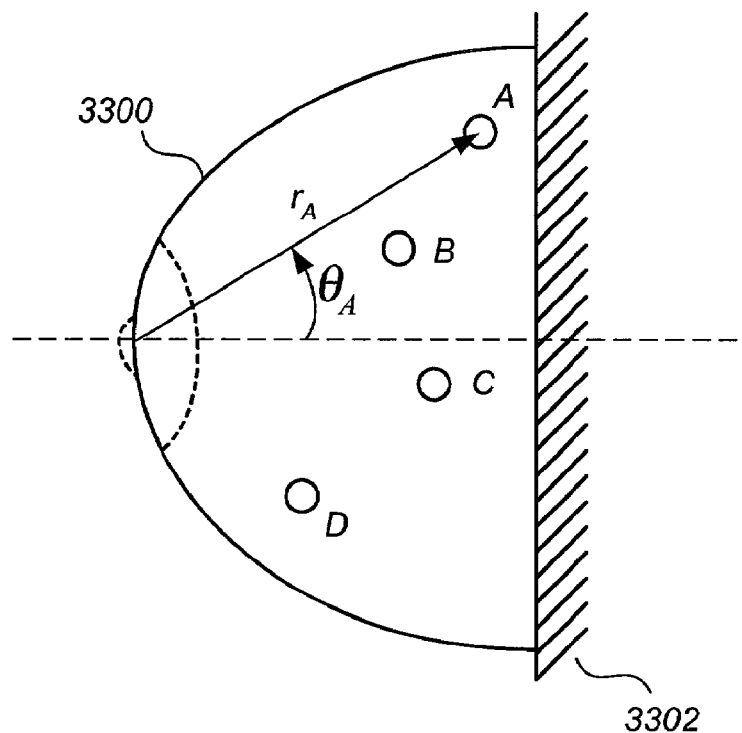
FIG. 33 illustrates a conceptual diagram of a digitized x-ray mammogram and regions of interest therein.

FIG. 33 illustrates a conceptual diagram of a digitized x-ray mammogram 3300 and regions of interest (ROIs) A, B, C, and D therein. Each ROI is a fixed distance $r_A$, $r_B$, $r_C$, and $r_D$, respectively, from the nipple as can be determined using known methods. Also, each ROI is at an angle $\theta_A$, $\theta_B$, $\theta_C$, and $\theta_D$ with respect to an axis perpendicular to the chest wall and passing through the nipple, as can be determined using known methods.

Figure 34:
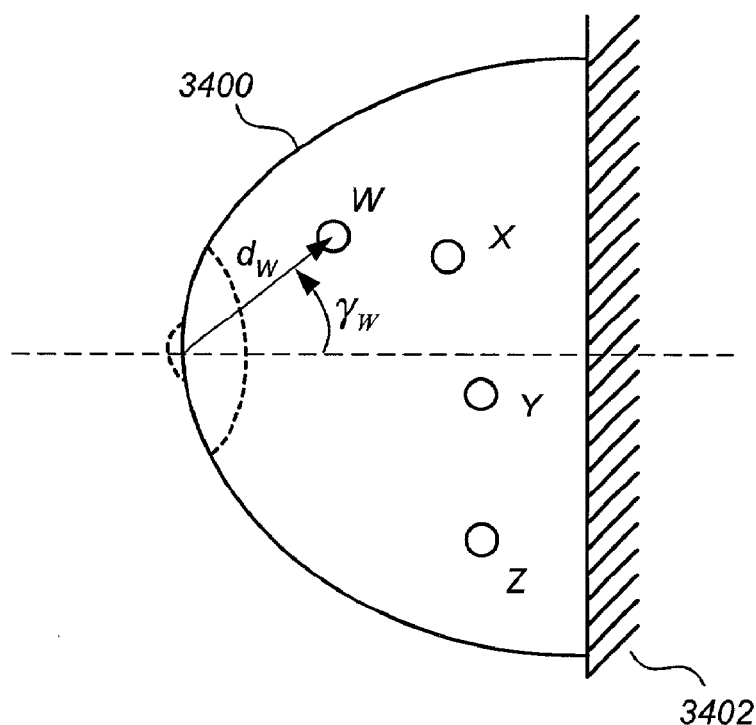
FIG. 34 illustrates a conceptual diagram of an adjunctive ultrasound view and regions of interest therein.

FIG. 34 illustrates a conceptual diagram of an adjunctive ultrasound view 3400 and regions of interest (ROIs) W, X, Y, and Z contained therein. Each ROI is a fixed distance $d_W$, $d_X$, $d_Y$, and $d_Z$, respectively, from the nipple as can be determined using known methods. Also, each ROI is at an angle $\gamma_W$, $\gamma_X$, $\gamma_Y$, and $\gamma_Z$ with respect to an axis perpendicular to the chest wall and passing through the nipple, as can be determined using known methods. More generally, the angles $\gamma_W$, $\gamma_X$, $\gamma_Y$, and $\gamma_Z$ can be measured from any fixed axis through the nipple, provided it is the same fixed axis that the angles $\theta_A$, $\theta_B$, $\theta_C$, and $\theta_D$ from the x-ray mammogram of FIG. 33 are measured from.

The goal of x-ray CAD/ultrasound CAD ROI registration according to the preferred embodiments is to find out (i)

which of the ROIs in the adjunctive ultrasound view 3400, if any, represent the same physical locus in the breast as the ROIs of the x-ray mammogram 3300, and (ii) which of the ROIs in the x-ray mammogram 3300, if any, represent the same physical locus in the breast as the ROIs of the adjunctive ultrasound view 3400. Traditionally, this would involve a complex image registration process where the entire images mathematically mapped onto each other, often requiring additional information that is extrinsic to the medical images themselves, such as position sensing readouts. However, it has been found that a much simpler method for registering ROIs between x-ray and adjunctive ultrasound views based on nipple distance, and optionally nipple angle, yields sufficiently reliable results.

Figure 35:
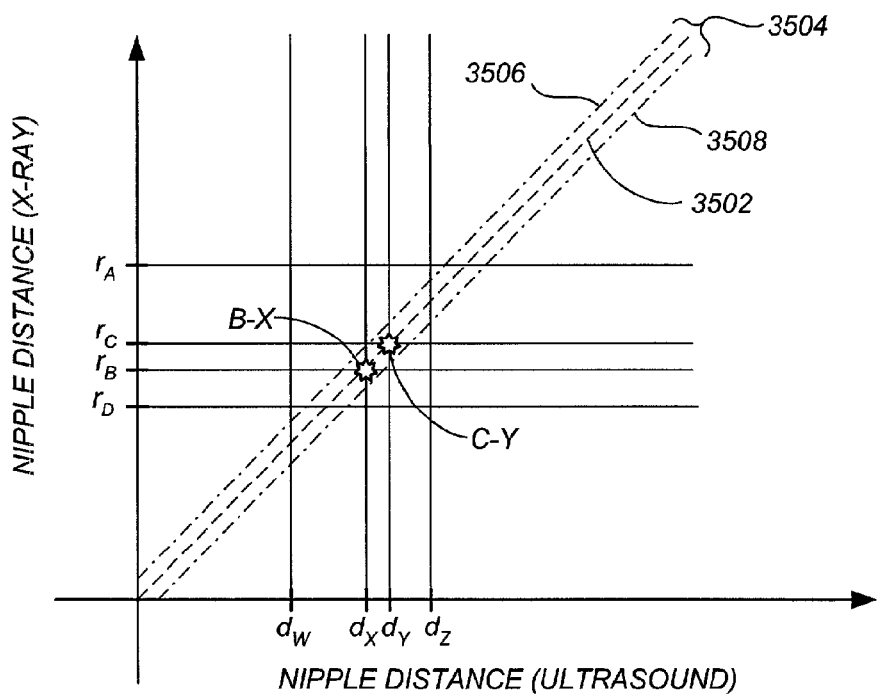
FIG. 35 illustrates a plot of nipple distance in an x-ray mammogram view versus nipple distance in an adjunctive ultrasound view for registering regions of interest between the x-ray mammogram view and the adjunctive ultrasound view.

FIG. 35 illustrates a plot of nipple distance in the x-ray mammogram view versus nipple distance in the adjunctive ultrasound view for registering ROIs therebetween. For each ROI A, B, C, and D in the x-ray mammogram view of FIG. 33, the nipple distance metric $r_A$, $r_B$, $r_C$, and $r_D$, respectively, is computed using known methods. Horizontal lines are drawn at ordinates corresponding to $r_A$, $r_B$, $r_C$, and $r_D$. For each ROI W, X, Y, and Z in the adjunctive ultrasound view of FIG. 34, the nipple distance metric $d_W$, $d_X$, $d_Y$, and $d_Z$, respectively, is computed using known methods. Vertical lines are drawn at the abscissas corresponding to $d_W$, $d_X$, $d_Y$, and $d_Z$. According to a preferred embodiment, if any horizontal line intersects with any vertical line within a predetermined tolerance of a 45-degree line 3502, then the x-ray ROI for that horizontal line is identified as being "registered" with the ultrasound ROI for that vertical line.

In the example of FIGS. 33-35, it is seen that the ROI "B" from the x-ray mammogram registers to the ROI "X" from the adjunctive ultrasound view, and that the ROI "C" from the x-ray mammogram registers to the ROI "Y" from the adjunctive ultrasound view. The particular locations of the upper and lower boundaries 3506 and 3508 around the 45-degree line 3502 that define a correlation region 3504 can be determined from a training process that would be readily apparent to a person skilled in the art in view of the present disclosure. Importantly, for the preferred embodiment in which nipple distance is the sole correlating factor, it is not required that the x-ray and adjunctive ultrasound images be taken from the same view (e.g., CC or MLO). Rather, it is only required that the scales of the respective medical images are known, so that actual nipple distances can be measured. It is to be appreciated that, while described in terms of a graphical process in FIG. 35, a computer program implementing this algorithm will, of course, achieve its results in purely numerical fashion without requiring the actual plotting of data on a two-dimensional plane. More particularly, the computer program would register any two ROIs whose difference falls within a predetermined absolute or relative tolerance.

Figure 36:
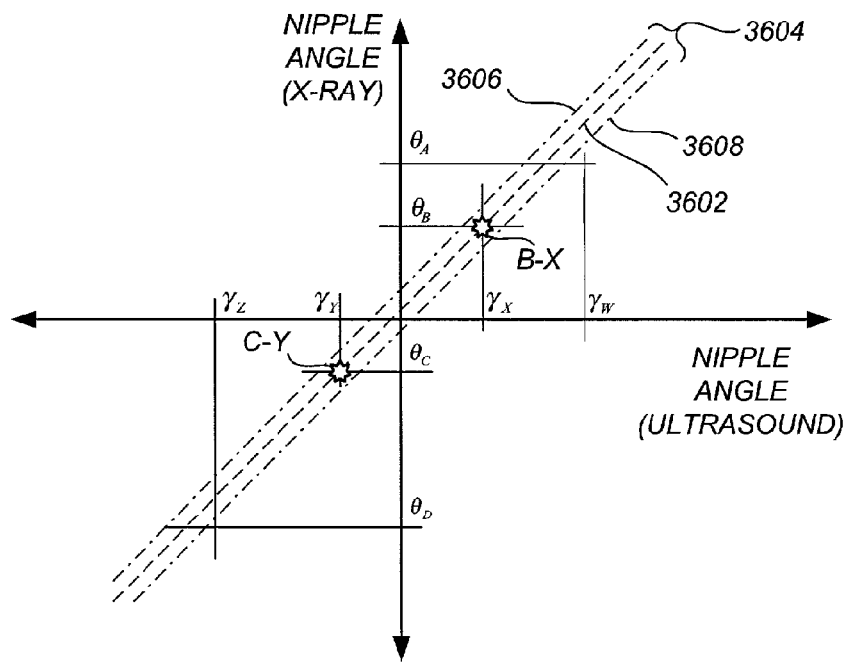
FIG. 36 illustrates a plot of nipple angle in an x-ray mammogram view versus nipple angle in an adjunctive ultrasound view for registering regions of interest between the x-ray mammogram view and the adjunctive ultrasound view.

FIG. 36 illustrates a plot of nipple angle in an x-ray mammogram view versus nipple angle in an adjunctive ultrasound view for registering regions of interest therebetween with additional precision. For the purposes of FIG. 36, it is presumed that the x-ray and adjunctive ultrasound images are taken from the same standard view (e.g., CC or MLO) or otherwise from the same angle relative to the patient. For each pair of ROIs that are determined to be registered by nipple distance metric supra, the nipple angles in both the x-ray mammogram and ultrasound view are determined using known methods. In the present example in which ROI B correlates to ROI X and ROI C correlates to ROI Y according to the nipple distance metric, the nipple angles $\theta_B$ and $\theta_C$ are determined and horizontal lines drawn at corresponding ordinates in FIG. 36, and the nipple angles $\gamma_X$ and $\gamma_Y$ are determined and vertical lines drawn at corresponding abscissas in FIG. 36. According to a preferred embodiment, the ROI pair B-X only continues to be identified as "registered" if the horizontal line for $\theta_B$ intersects with the vertical line for $\gamma_X$ within a predetermined tolerance of a 45-degree line 3602, and likewise for ROI pair C-Y. The particular locations of the upper and lower boundaries 3606 and 3608 around the 45-degree line 3602 that define a correlation region 3604 can be determined from a training process that would be readily apparent to a person skilled in the art in view of the present disclosure. As with the nipple distance criterion, it is to be appreciated that a computer program would carry out the above steps in a purely numerical fashion without regard to visual graphical plots.

In another preferred embodiment, the above lesion-centric registration process also uses lesion size as a factor in matching corresponding regions of interest in the x-ray mammogram view and the adjunctive ultrasound views. In still another preferred embodiment, the above lesion-centric registration process also uses lesion distance from the chest wall as a factor in matching corresponding regions of interest in the x-ray mammogram view and the adjunctive ultrasound views. For a given lesion, the chest wall distance corresponds, for example, to a horizontal distance between that lesion and the chest wall 3302/3402 of FIGS. 33/34, respectively. Thus, for example, an ROI pair that would be identified as "registered" between the x-ray mammogram view and the adjunctive ultrasound views based on nipple distance and nipple angle would continue to be identified as "registered" only if they are of substantially similar size and have a substantially identical distance from the chest wall.

Thus, according to the preferred embodiments of FIGS. 32-36, the advantages of using a combination of both x-ray CAD data and ultrasound CAD data are provided, without requiring extrinsic information to correlate the two imaging modalities with each other. From a practical viewpoint, this provides a key advantage in integrating ultrasound mammography into the current mass breast cancer screening environment, because the current x-ray mammogram infrastructure can remain substantially undisturbed. If desired by the HMO or health care institution, the adjunctive ultrasound data can be obtained in an entirely separate clinical process, and yet the adjunctive ultrasound CAD results can still be advantageously and automatically combined with x-ray mammogram CAD results for increased specificity and sensitivity.

Also within the scope of the preferred embodiments is a computer program product for instructing one or more processors to carry out one or more of the methods of the preferred embodiments, such computer program product being amenable to ready implementation by a person skilled in the art in view of the present disclosure. In one preferred embodiment, the computer program product is executed primarily by the ultrasound server 106 of FIG. 1, with the other system devices of FIG. 1 performing simple input/output, display, and storage functions. In other preferred embodiments, the computer program product is distributed across the different systems of FIG. 1, with different algorithmic portions being carried out by different systems or subsystems. Ultrasound server 106 comprises a computer system that includes a cabinet, a display monitor, a keyboard, and a mouse, the mouse having one or more buttons for interacting with a graphical user interface. The cabinet typically houses a CD-ROM, zip, and/or floppy disc drive, system memory and a hard drive which can be utilized to store and retrieve software programs incorporating computer code that implements the preferred embodiments, data for use with the invention, and the like. An external hard drive is also shown in FIG. 1. Although CD- ROM, zip, and floppy discs represent common computer readable storage mediums, other computer readable storage media including tape, flash memory, system memory, and hard drives can be used. Additionally, a data signal embodied in a carrier wave, such as in a network including the Internet or an intranet, can form the computer readable storage medium.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although described supra in terms of adjunctive ultrasound screening, in view of the present disclosure one skilled in the art would readily be able to apply the thick-slice display apparatus of the preferred embodiments in the context of computerized tomography (CT) and/or magnetic resonance imaging (MRI) environments. In each case, individual image slices generated from CT scans or MRI scans of the breast are compounded so as to form thick-slice images of slab-like portions of the breast along planes parallel to a standardized x-ray mammogram view plane, and the thick-slice images are displayed to the radiologist in close proximity to an x-ray mammogram of the breast to assist in interpreting that x-ray mammogram. Preferably, a single composite view of the whole breast is shown together with the thick-slice image views, these views having their gray-scale polarities toggled and/or remapped such that they are reminiscent of x-ray mammogram views taken from the standardized direction. By way of further example, real-time implementations of the preferred embodiments may be readily extended to operate with an ultrasound-guided, computer-controlled biopsy apparatus. A surgeon can instantiate an automatic biopsy extraction procedure by graphically selecting the precise three-dimensional location (x, y, z) of a target lesion on the real-time adjunct ultrasound display as the breast is held steady by the compression device. A biopsy needle is automatically manipulated by a motorized mechanism that translates the biopsy needle in two dimensions to the desired (x, y) location, and then guides the physician in inserting the needle or automatically inserts the needle in the "z" direction to enter the tumor, all the while being controlled by a feedback control system to keep the needle on-target. In this example, the "z" direction can be parallel to the compression plates, or alternatively can be perpendicular the compression plates where adequate holes or gaps in one of the compression plates are provided to allow the needle to pass therethrough. In other preferred embodiments, apparatuses similar to those described in one or more of the following references can be used, which are incorporated by reference herein: U.S. Pat. No. 5,078,142; U.S. Pat. No. 5,660,185; U.S. Pat. No. 5,833,627; and U.S. Pat. No. 6,102,866. Therefore, reference to the details of the preferred embodiments are not intended to limit their scope, which is limited only by the scope of the claims set forth below.

(A) C D Lehman et al; AJR 1999; 173: 1651-1655; "Effect of Age and Breast Density on Screening Mammograms with False-Positive Findings".

(B) L Jalali; Adv. For Adm. in Radiology and Rad. Oncology; March 1999: 68-70; "Sound Combination—Ultrasound paired with mammography can improve cancer detection for dense-breasted women".

(C) R D Rosenberg et al; Radiology 1998; 209:511-518; "Effects of Age, Breast Density, Ethnicity, and Estrogen Replacement Therapy on Screening Mammographic Sensitivity and Cancer Stage at Diagnosis: Review of 183, 134 Screening Mammograms in Albuquerque, N. Mex.".

(D) T Kolb et al; Radiology 1998; 207:191-199; "Occult Cancer in Women with Dense Breasts: Detection with Screening US—Diagnostic Yield and Tumor Characteristics".

(E) W Buchberger et al; AJR 1999; 173:921-927; Incidental Findings on Sonography of the Breast".

(F) W A Berg et al; Radiology 2000; 214:59-66; "Multicentric and Multifocal Cancer: Whole-Breast US in Prospective Evaluation".

(G) R S Butler et al; AJR 1999; 172:325-330; "Sonographic Evaluation of Infiltrating Lobular Carcinoma".

(H) C Merritt; A talk presented at the Institute of Medicine Workshop for the Early Detection of Breast Cancer; Feb. 9-10, 2002.

(I) L Liberman et al; Radiology 1998; 208:717-723; "US-guided Core Breast Biopsy: Use and Cost-effectiveness".

The invention claimed is:

1. A system for ultrasound examination of a patient's breast, comprising:
   a scanning apparatus including
      (i) an ultrasonically transparent compressive member configured to selectively compress the patient's breast along a compression direction,
      (ii) an ultrasound transducer, and
      (iii) an actuation assembly coupled to the ultrasound transducer and configured to translate the ultrasound transducer in a scanning direction across the compressive member as the ultrasound transducer scans the compressed breast through the compressive member,
   the ultrasound transducer being long in a direction transverse to the scanning direction, said scanning apparatus acquiring image data representing a plurality of thin-slice images,
      said thin-slice images conforming to respective planes that are generally along the compression direction, and
      each of said thin-slice images representing a thin slice of the patient's breast;
   a processor configured to process said image data representing said thin-slice images into image data representing a plurality of thick-slice images that are fewer in number than said thin slices,
      said thick-slice images conforming to respective planes that are transverse to the compression direction, and
      each of said thick-slice images representing a thick slice of the patient's breast that is thicker than a slice represented by one of said thin-slice images; and
   a computerized display that displays a plurality of said thick-slice images to thereby represent for viewing medical information regarding the patient's breast in fewer displayed images than if said thin-slice images were displayed.

2. The system of claim 1, said thick-slice images including a nearest thick-slice image representative of a thick slice of the patient's breast nearest to said compressive member and a farthest thick-slice image representative of a thick slice of the patient's breast farthest from said compressive member, said image data acquired by the scanning apparatus being representative of an entire volume of the patient's breast extending from said nearest thick slice to said farthest thick slice and including said nearest and farthest thick slices, wherein each of said thick-slice images represents a thick slice of the patient's breast having a thickness between about 2 mm and 20 mm.

3. The system of claim 2, wherein said computerized display displays all of said thick-slice images representative of the entire volume of the patient's breast in a simultaneous, side-by-side manner.

4. The system of claim 3, wherein said computerized display displays between about 4 to 16 thick-slice images in said simultaneous, side-by-side manner representative of an equal number of thick slices collectively occupying said entire breast volume.

5. The system of claim 4, wherein said thick slices represented by said 4 to 16 thick-slice images are non-overlapping in space within said breast volume.

6. The system of claim 2, wherein each of said thick-slice images represents a thick slice of the patient's breast having a thickness of about 12 mm.

7. The system of claim 2, wherein each of said thick-slice images represents a thick slice of the patient's breast having a thickness of about 7 mm.

8. The system of claim 2, wherein each of said thick-slice images represents a thick slice of the patient's breast having a thickness of about 2 mm.

9. The system of claim 2, wherein said ultrasound transducer is sufficiently long in said direction transverse to the scanning direction such that, for a conventional range of breast sizes, the entire breast volume is scanned in a single translation of the ultrasound transducer from a first side to an opposite side of the compressive member.

10. The system of claim 9, wherein said ultrasound transducer is longer than 7.5 cm in said direction transverse to the scanning direction.

11. The system of claim 10, wherein said ultrasound transducer is about 15 cm in said direction transverse to the scanning direction.

12. The system of claim 9, wherein said scanning apparatus is configured such that said ultrasound transducer acquires one ultrasound frame for every 0.15 mm-0.75 mm of distance translated in said scanning direction, and wherein said ultrasound transducer is operated at a frequency of at least 7.5 MHz.

13. The system of claim 2, wherein said compressive member compresses the patient's breast during said scanning as in taking a standard x-ray mammogram view, and wherein said farthest thick slice of the patient's breast is nearest to a rigid plate opposite said compressive member relative to the patient's breast, said compressive member compressing the patient's breast toward said rigid plate.

14. The system of claim 1, wherein said compressive member comprises a taut, partially conformable sheet of a flexible material.

15. The system of claim 14, wherein said sheet of a flexible material comprises a polyester film.

16. The system of claim 14, wherein the thin slices conform to planes transverse to the patient's chest wall and the thick slices conform to planes transverse to those of the thin slices.

17. A method of ultrasound examination of a patient's breast and computer-implemented processing and displaying breast ultrasound data, comprising:
selectively generating three-dimensional image data describing a plurality of thin-slice ultrasound images by ultrasonic imaging of a patient's breast as compressed by a compressive member in a direction of compression, said thin-slice images conforming to respective planes that are generally along the compression direction, and each of said thin-slice images representing a thin slice of the patient's breast;
computer-processing said image data representing said thin-slice images into image data representing a plurality of thick-slice images that are fewer in number than said thin slices,
said thick-slice images conforming to respective planes transverse to the compression direction, and
each of said thick-slice images representing a thick slice of the patient's breast that is thicker than a slice represented by one of said thin-slice images; and
displaying on a computerized display a plurality of said thick-slice images to thereby present for viewing medical information regarding the patient's breast in fewer displayed images than if said thin-slice images were displayed.

18. The method of claim 17, said thick-slice images including a nearest thick-slice image representative of a thick slice of the patient's breast nearest to said compressive member and a farthest thick-slice image representative of a thick slice of the patient's breast farthest from said compressive member, said image data being representative of an entire volume of the patient's breast extending from said nearest thick slice to said farthest thick slice and including said nearest and farthest thick slices, wherein each of said thick-slice images represents a thick slice of the patient's breast having a thickness between about 2 mm and 20 mm.

19. The method of claim 17, wherein said thick-slice images representing thick slices of the breast collectively occupy the entire patient's breast and are displayed on said computerized display in a simultaneous, side-by-side manner.

20. The method of claim 17, wherein there are between about 4 to 16 thick-slice images displayed in said simultaneous, side-by-side manner representative of an equal number of thick slices collectively occupying the entire breast.

21. The method of claim 20, wherein said thick slices represented by said 4 to 16 thick-slice images are non-overlapping in space within the breast.

22. The method of claim 17, wherein each of said thick-slice images represents a thick slice of the patient's breast having a thickness of about 12 mm.

23. The method of claim 17, wherein each of said thick-slice images represents a thick slice of the patient's breast having a thickness of about 7 mm.

24. The method of claim 17, wherein each of said thick-slice images represents a thick slice of the patient's breast having a thickness of about 2 mm.

25. The method of claim 17, wherein each of said thick-slice images represents a thick slice of the patient's breast oriented at an angle corresponding to a standard x-ray mammogram view.

26. The method of claim 17, wherein said ultrasonic imaging comprises scanning the patient's breast with an ultrasonic transducer automatically driven across the patient's breast.

27. A non-transitory computer readable medium tangibly embodying one or more sequences of instructions wherein execution of the one or more sequences of instructions by one or more processors causes the one or more processors to perform the steps of:
selectively generating image data representing image data of a plurality of thin-slice ultrasound images acquired by ultrasonically imaging a patient's breast as compressed by a compressive member in a direction of compression, said thin-slice images conforming to respective planes that are generally along the compression direction, and each of said thin-slice images representing a thin slice of the patient's breast;
computer-processing said image data representing said thin-slice images into image data representing a plurality of thick-slice images,
said thick slice imaged being fewer in number than said thin slices,
said thick-slice images conforming to respective planes transverse to the compression direction, and
each of said thick-slice images representing a thick slice of the patient's breast that is thicker than a slice represented by one of said thin-slice images; and
causing to be displayed on a computerized display a plurality of said thick-slice images to thereby present for viewing medical information regarding the patient's breast in fewer displayed images than if said thin-slice images were displayed.

28. The computer readable medium of claim 27, said thick-slice images including a nearest thick-slice image representative of a thick slice of the patient's breast nearest to said compressive member and a farthest thick-slice image representative of a thick slice of the patient's breast farthest from said compressive member, said image data being representative of an entire volume of the patient's breast extending from said nearest thick slice to said farthest thick slice and including said nearest and farthest thick slices, wherein each of said thick-slice images represents a thick slice of the patient's breast having a thickness between about 2 mm and 20 mm.

29. The computer readable medium of claim 28, wherein said thick-slice images represent thick slices of the breast collectively occupying said entire volume of the patient's breast, and wherein all of said thick-slice images are displayed on said computerized display in a simultaneous, side-by-side manner.

30. The computer readable medium of claim 29, wherein there are between about 4 to 16 thick-slice images displayed in said simultaneous, side-by-side manner representative of an equal number of thick slices collectively occupying said entire breast volume.

31. The computer readable medium of claim 30, wherein said thick slices represented by said 4 to 16 thick-slice images are non-overlapping in space within said breast volume.

32. The computer readable medium of claim 28, wherein each of said thick-slice images represents a thick slice of the patient's breast having a thickness of about 12 mm.

33. The computer readable medium of claim 28, wherein each of said thick-slice images represents a thick slice of the patient's breast having a thickness of about 7 mm.

34. The computer readable medium of claim 28, wherein each of said thick-slice images represents a thick slice of the patient's breast having a thickness of about 2 mm.

35. The computer readable medium of claim 28, wherein each of said thick-slice images represents a thick slice of the patient's breast oriented at an angle corresponding to a standard x-ray mammogram view.

36. The computer readable medium of claim 28, said one or more sequences of instructions further causing the one or more processors to perform, in said ultrasonically imaging, the steps of:
causing an actuation assembly coupled to an ultrasound transducer of a scanning apparatus containing said compressive member to translate the ultrasound transducer in a scanning direction across the compressive member in contact therewith; and
causing the ultrasound transducer to scan the compressed breast through the compressive member while being so translated in said scanning direction.

37. The computer readable medium of claim 36, the ultrasound transducer being sufficiently long in a direction transverse to the scanning direction such that, for a conventional range of breast sizes, the entire breast volume is scanned in a single translation of the ultrasound transducer from a first end to an opposite end of the compressive member, wherein said ultrasound transducer is caused to acquire one ultrasound frame for every 0.15 mm-0.75 mm of distance translated in said scanning direction, and wherein said ultrasound transducer is caused to operate at a frequency of at least 7.5 MHz.

* * * * *